(12) United States Patent
Weigele et al.

(10) Patent No.: US 6,576,766 B1
(45) Date of Patent: Jun. 10, 2003

(54) SIGNAL TRANSDUCTION INHIBITORS, COMPOSITIONS CONTAINING THEM

(75) Inventors: Manfred Weigele, Cambridge, MA (US); Regine Bohacek, Boston, MA (US); Virginia A. Jacobsen, Boston, MA (US); Karina Macek, Winchester, MA (US); Michael G. Yang, Wilmington, DE (US); Noriyuki H. Kawahata, Medford, MA (US); Rajeswari Sundaramoorthi, Watertown, MA (US); Yihan Wang, Belmont, MA (US); Craig S. Takeuchi, San Diego, CA (US); George P. Luke, Branford, CT (US); Chester A. Metcalf, III, Boston, MA (US); William C. Shakespeare, Framingham, MA (US); Tomi K. Sawyer, Southborough, MA (US)

(73) Assignee: Ariad Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/554,230

(22) PCT Filed: Nov. 12, 1998

(86) PCT No.: PCT/US98/24168
§ 371 (c)(1),
(2), (4) Date: Aug. 17, 2000

(87) PCT Pub. No.: WO99/02442
PCT Pub. Date: May 20, 1999

(51) Int. Cl.$^7$ .................. C07D 307/89; C07D 209/14; C07D 327/06; C07F 9/38
(52) U.S. Cl. .................. 548/414; 549/10; 549/299; 558/159; 558/170; 562/14; 562/15; 562/451
(58) Field of Search .................. 548/414; 549/10, 549/299; 558/159, 170; 562/14, 15, 451

(56) References Cited

U.S. PATENT DOCUMENTS 5,183,815 A 2/1993 Saari et al. .................. 514/172

FOREIGN PATENT DOCUMENTS

| EP | 0832875 | 4/1998 |
|----|---------|--------|
| WO | WO 97/12903 | 4/1997 |
| WO | WO 97/31016 | 8/1997 |
| WO | WO 98/40093 | 9/1998 |
| WO | WO 99/47529 | 9/1999 |

OTHER PUBLICATIONS

Stankovic et al., "The role 4–phosphonodifluoromrthyl– and 4–phosphono–phenylalanine in the selectivity and cellular uptake of SH2 domain ligands." —(1997) Bioorganic & Medicinal Chemistry Letters, 7(14): 1909–1914.

Plummer, M. "Design, synthesis, and cocrystal structure of a nonpeptide Src SH2 domain ligand." —(1997) Journal of Medicinal Chemistry, 40(23): 3719–3725.

Lunney, E. "Structure–based design of a novel series of nonpeptide ligands that bind to the pp60src SH2 domain." —(1997) Journal of the American Chemical Society, 119(51): 12471–12476.

Primary Examiner—Fiona T. Powers
(74) Attorney, Agent, or Firm—David L. Berstein

(57) ABSTRACT

This invention concerns compounds for inhibiting intracellular signal transduction, especially intracellular signal transduction mediate by one or more molecular interactions involving a phosphotyrosine-containing protein. This invention also relates to pharmaceutic compositions containing the compounds and prophylactic and therapeutic methods involving pharmaceutical and veterinary administration of the compounds. The compounds are of formula (1) as defined herein.

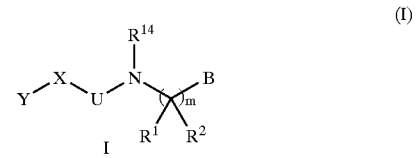

73 Claims, No Drawings

SIGNAL TRANSDUCTION INHIBITORS, COMPOSITIONS CONTAINING THEM

This application is a 371 of PCT/US98/24168 filed Nov. 21, 1998.

FIELD OF THE INVENTION

This invention concerns a new class of compounds which have a broad range of useful biological and pharmacological activities. In particular, these compounds are useful for inhibiting intracellular signal transduction, especially intracellular signal transduction mediated by one or more molecular interactions involving a phosphotyrosine-containing protein. This invention also relates to pharmaceutical compositions containing the compounds and prophylactic and therapeutic methods involving pharmaceutical and veterinary administration of the compounds.

BACKGROUND OF THE INVENTION

Cellular signal transduction, i.e., the series of events leading from extracellular events to intracellular sequelae, is an aspect of cellular function in both normal and disease states. Numerous proteins that function as signal transducing molecules have been identified, including receptor and non-receptor tyrosine kinases, phosphatases and other molecules with enzymatic or regulatory activities. These molecules generally demonstrate the capacity to associate specifically with other proteins to form a signaling complex that can alter cell activity.

Signaling proteins often contain domain(s) of conserved sequence which constitute catalytic domains such as kinase or phosphatase domains, or serve as non-catalytic modules that direct protein:protein or other inter- or intramolecular interactions during signal transduction. Such domains include among others, Src homology 2 ("SH2") and phosphotyrosine interaction ("PI") domains. SH2 and PI domains recognize, i.e., bind to, proteins containing characteristic peptide sequences which include one or more phosphorylated tyrosine ("pTyr") residues. Significant information related to such domains, proteins containing them, the production of proteins containing such domains (including protein fragments and fusion proteins), the characteristic peptide sequences which they recognize and the biological and/or clinical role played by the interactions of such proteins has been described in the scientific literature. See e.g. U.S. Pat. No. 5,667,980, PCT/US97/02635 ("Cell-Based Assay") and WO 97/39326 ("In Vitro Fluorescence Polarization Assay") and references cited therein for additional background information on SH2 and PI domains, inhibition of intermolecular interactions mediated by such domains, assays and related topics.

The protein domains of the tyrosine kinase, Src, gave rise to the "Src homology" ("SH") nomenclature and illustrate this class of proteins. At least nine members of the Src family of tyrosine kinases have been identified to date in vertebrates including Src (alternatively known as c-src and pp60c-src), Fyn, Yes, Lyn, Hck, Fgr, Blk and Yrk. Sequence analysis of the Src tyrosine kinases reveals that each family member contains an N-terminal membrane anchor, a poorly conserved "unique" region of 40–70 amino acids, a Src homology 3 (SH3) domain of about sixty amino acids capable of protein-protein interactions with proline-rich sequences and a Src homology 2 (SH2) domain comprising about 100 amino acid residues which mediates binding of the Src family member of phosphotyrosine-(pTyr) containing peptides and proteins (reviewed in Superti-Furga, FEBS Lett. 369:62–66 (1995). Several cognate phosphoproteins known to bind the Src SH2 domain include middle T antigen, PDGF receptor, EGF receptor, and focal adhesion kinase (FAK). See Courtneidge et al, J. Virol. 65:3301–3308 (1991); Moi et al. EMBO J. 12:2257–2264 (1993); Luttrell et al. Proc. Natl. Acad. Sci. USA 91:83–87 (1994); and Xing et al, Mol. Biol. Cell 5:413–421 (1994). For additional information on other SH2 domains (including, e.g., ZAP-70, Syk, Shc, Tsk, Btk, VAV, Grb2, Crk, STATs) and PI domain-containing proteins, see WO 97/39326 and references cited therein.

The molecular structure of several SH2 domains has been solved and, in particular, the molecular structure of certain SH2 domains in complex with a phosphotyrosine-containing peptide or peptide analog has been elucidated. See Waksman et al, Cell 72:779–790 (1993); Xu et al. Biochemistry 34:2107–2121 (1995); Hatada et al., Nature 377(6544), 32–38 (1995). Whereas the general consensus sequence of Src family SH2-binding peptides, for example, comprises a pTyr-X-X-(Leu/Ile) motif, SH2 domain binding specificity is thought to be influenced significantly by the specific amino acids located carboxy-terminal to the pTyr residue. For example, the pp60c-src, Fyn, Lck and Fgr SH2 domains prefer the sequence pTyr-Glu-Glu-Ile. See Songyang et al, Cell 72:767–778 (1993). Crystallographic data concerning pp60c-src SH2 in complex with synthetic peptides has revealed, in particular, two important binding determinants for binding to phosphotyrosine-containing proteins or peptides: the phosphotyrosine binding site which is electropositive in nature such that phosphotyrosine binding is stabilized and the lipophilic binding site which stabilizes binding of pTyr+3 residues within the phosphotyrosine-containing peptides via hydrophobic contacts. Reviewed by Brown and Cooper, Biochim. Biophys. Acta 1287 (2–3) :121–149 (1996).

Structural studies of phosphotyrosine-containing peptides complexed with isolated SH2 domains has provided information regarding the molecular interactions of peptide ligands with the SH2 domain peptidyl binding site. Recent attempts have been made to extrapolate these data to design novel peptide ligands and peptidomimetic agonists of SH2-mediated signaling. For example, Plummer et al reported that incorporation of C-terminal D-amino acid residues to tripeptide SH2 domain ligands increases affinity relative to their L-amino acid-containing counterparts. See Plummer et al, Drug Design Discovery 13:75–81 (1996). Burke et al reported that hexapeptides containing difluoro-(phosphonomethyl)phenylalanine bound SH2 domains with high relative affinity compared to analogous pTyr peptides and were resistant to naturally-occurring cellular phosphatases. Studies of the pTyr residue of peptide agonists of the Src SH2 domain have shown that that phosphate ester is important for molecular recognition, and that significant loss in binding occurs when it is replaced with sulfate, carboxylate, nitro, hydroxy or amino groups. See Gilmer et al, J Biol Chem 269:31711–31719 (1994).

Many signaling pathways which play critical roles in disease processes are mediated by the binding of a phosphotyrosine-containing protein or protein domain with an SH2 or other protein receptor for a tyrosine-phosphorylated domain. Pharmaceutical agents which interfere with signaling mediated by such molecules, e.g., which interfere with the formation or stability of such signaling complexes, may be used for precise intervention in these complex biological processes in order to treat or prevent the diseases or pathological effects mediated by such signaling. Such interference may be achieved through a variety of mechanisms, including competitive inhibition of a phosphotyrosine containing ligand with its receptor (e.g., with an SH2-containing protein), inhibition of phosphorylation of the tyrosine residue of such a ligand, inhibition of activation of a kinase which catalyzes the phosphorylation of a ligand in a signaling pathway, etc.

Compounds that can enter cells and block a signal transduction pathway of interest, such as an SH2-mediated pathway, would be of great interest as reagents for biological research and for pharmaceutical and veterinary uses.

SUMMARY OF THE INVENTION

This invention concerns compounds of Formula I, or pharmaceutically acceptable derivatives thereof:

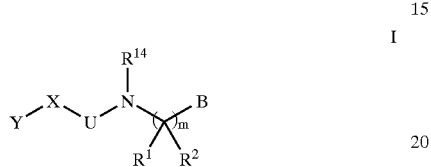

I in which
Y is

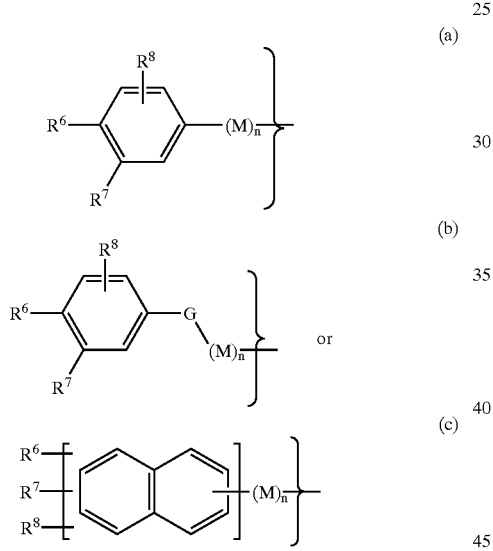

G is —O—, —S— or —N—;
$R^6$ comprises —APO$_3$RR', —OPO$_3$RR', —ASO$_3$R, —OSO$_3$R, —ACO$_2$R, —A-tetrazole, —ASO$_2$NRR', —ACOCF$_3$, —(C=O)J, —C(R)(J)(K) or —C(Z)(J)(K);
where each occurrence of A is independently a covalent bond, —G—M— or —(M)$_m$—;
each occurrence of M is an independently selected, substituted or unsubstituted, methylene moiety, and any M-M' moiety may be electronically saturated or unsaturated and/or may be part of a 3–8-membered ring. Illustrative "M" moieties include —CH$_2$—, —CHF—, —CF$_2$—, —CHOH—, —CH(Me)—, etc.
Each n is independently 0, 1, 2, 3, 4 or 5 (in many embodiments n is 0, 1 or 2); each m is independently 0, 1 or 2;
J and K are independently selected from the group consisting of —APO$_3$RR', —OPO$_3$RR', —ASO$_3$R, —OSO$_3$R, —ACO$_2$R, —A-tetrazole, —ASO$_2$NRR', —(M)$_n$NRR' and —(M)$_n$OR;

Z is a halogen (i.e., F, Cl, Br or I);
$R^7$ and $R^8$ are independently R, —CN, —NO$_2$, Z, J, —A(M)$_n$aliphatic, —G(M)$_n$aliphatic, —(M)$_n$COR (including e.g., —(M)$_n$COCF$_3$), —(M)$_n$OR, —(M)$_n$COOR, —A—(M)$_n$NRR', —G—(M)$_q$NRR', —(M)$_n$CHO, —A(M)$_n$N(R)(CO)R', —A(M)$_n$N(R)(CO)GR', —G(M)$_q$N(R)(CO)R', —G—(M)$_q$N(R)(CO)G'R', —A—(M)$_n$—CO—NRR', or —G—(M)$_n$—CO—NRR', where the aliphatic groups may be substituted or unsubstituted; or
$R^8$ is a covalent bond to an $R^4$ substituent of X forming an aliphatic, aryl or heterocyclic ring of 4 to 8 atoms (including, for example a 5-membered nitrogen-containing ring of an indole moiety);
Each occurrence of R (unnumbered) represents hydrogen or an aliphatic, heteroaliphatic, aryl, heteroaryl, (aryl)aliphatic-, or (heteroaryl)aliphatic moiety, each of which (other than hydrogen) may be substituted or unsubstituted, e.g., with any of the various substituents listed, illustrated or otherwise disclosed herein. While each occurrence of "R" within a given compound is thus independently selected, where multiple R groups are depicted in the same figure or moiety, the various R groups are generally marked R, R', R" and so on, as a reminder that they may be the same or different. (The same is true in the case of numbered "R" groups and other variables such as "m", "n", "M", etc. where apostrophes are used for the same purpose. Note also that the n M groups in a "M$_n$" moiety may be the same or different from one another.)
q is an integer from 1 to 8, and in many embodiments is 1, 2 or 3;
$R^1$ is hydrogen, aliphatic, —(M)$_n$-cycloaliphatic, —(M)$_n$-aryl, or —(M)$_n$-heterocyclic, each of which, other than H, may be substituted or unsubstituted (including, e.g. with moieties such as —(M)$_n$CO$_2$R, —(M)$_n$C(O)NRR', —(M)$_n$Z, —(M)$_n$CN, —(M)$_n$tetrazole, etc.);
$R^2$ is hydrogen or substituted or unsubstituted aliphatic, which is optionally covalently linked with $R^1$ to form a ring;
or $R^1$ or $R^2$ are covalently linked to B or to a substituent of B to form a 4–10-membered ring (which may be saturated or unsaturated);
X is:

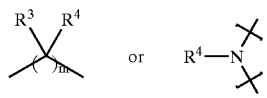

$R^3$ is hydrogen, R(CO)NR'—, RR'N(CO)NR"—, R'SO$_2$NR—, —R'CSNR—, RR"NCSNR"—, RR"NSO$_2$NR"—, R'OCONR—, RR'N—, or

$R^4$ is hydrogen, aliphatic (which may be branched, unbranched or cyclic), cycloaliphatic-(M)$_n$—, aryl-(M)$_n$—, heterocyclic-(M)$_n$—, RSO$_2$(M$_n$)—, (CO$_2$R)(M)$_n$— or (RR'N—CO)(M)$_n$, where the aliphatic, cycloaliphatic, aryl and heterocyclic groups are substituted or unsubstituted;

B is

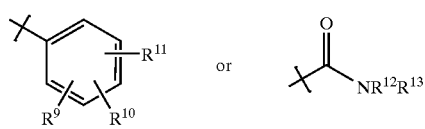 or 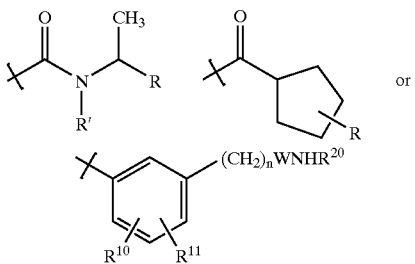

where $R^9$, $R^{10}$ and $R^{11}$ are independently selected from —$(M)_n$R, —$G(M_n)R$, —$(M)_n Z$, —$(M)_n CN$, —$(M)_n GR$, —$(M)_n NRWR$, —$(M)_n NRW$—GR, —$(M)_n W$—R, —G—$(M)_n W$—R, and —$(M)_n W$—GR, and include moieties such as, —$O(M_n)$aliphatic, —$O(M_n)$ cycloaliphatic, —$O(M_n)$heterocyclic and —$O(M_n)$aryl, where the aryl, heterocyclic, aliphatic and cycloaliphatic moiety may be substituted or unsubstituted, as well as moieties such as R, —OR, —SR, —CHO, —COR, —COOH (or amide, ester, carbamate, urea, oxime or carbonate thereof), —$NH_2$ (or substituted amine, amide, urea, carbamate or guanidino derivative therof), halo, trihaloalkyl, cyano, —$SO_2$—$CF_3$, —$OSO_2 F$, —$OS(O)_2 R$, —$SO_2$—NHR, —$NHSO_2 R$, sulfate, sulfonate, aryl and heteroaryl moieties. Alternatively, $R^{10}$ and $R^{11}$ are covalently linked together to form an aliphatic, hetercyclic or aryl fused ring, typically of 5–7 members. For example, in some embodiments, $R^{10}$ and $R^{11}$ comprise —G—$(M)_n$/—G'—, as illustrated by the following structure for B where, for the sake of example, each M is —$CH_2$— and n is 3:

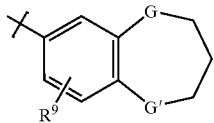

where in some cases G is —O— and G' is —S—, for example.

$R^{12}$ and $R^{13}$ are independently selected from the group consisting of hydrogen, aliphatic, heteroaliphatic, aryl, heteroaryl, (aryl)aliphatic-, or (heteroaryl)aliphatic, each of which (other than hydrogen) may be substituted or unsubstituted; (including e.g., hydrogen, aliphatic, —$M_n$-cycloaliphatic, —$M_n$-aryl, —$M_n$-heteroaryl, or —$M_n CO_2 R$, where the aliphatic, cycloaliphatic, aryl or heteroaryl moiety(ies) is(are) substituted or unsubstituted) or $R^{12}$ and $R^{13}$ are covalently linked together to form a heterocyclic moiety;

$R^{14}$ is R (and is preferably H); and,

U and W are independently —CO—, —CS—, —M—, —SO—, or —$SO_2$—.

In embodiments in which $R^6$ is $(H_2 O_3 P)_2 CH$—, particularly where $R^7$ and $R^8$ are H, B is —C(O)NRR', and X is —CHNR—, $R^4$ is other than a hydroxamic acid-containing moiety (i.e., does not comprise —NHOR where R is H, substituted or unsubstituted benzyl, trialkylsilyl, t-butyldiphenylsilyl, tetrahydropyranyl or t-butyl)).

Also, in embodiments in which Y is of the structure (a), shown above, where $R^6$ is —$OPO_3 RR'$, —$CF_2 PO_3 RR'$, —$CH_2 PO_3 RR'$, —$SO_3 R$, —$OSO_3 R$, $CH_2 SO_3 R$, —$SO_2 NH_2$, or —$CH_2 SO_2 NH_2$; and B is —(O)NRR' or

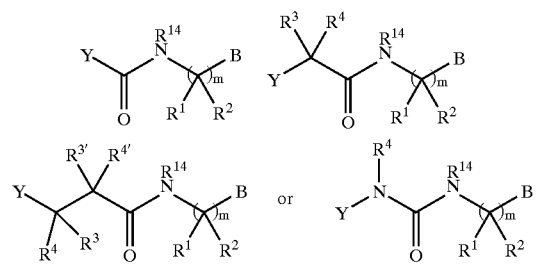

where $R^{10}$ is H, Z or alkyl; $R^{11}$ is H, alkyl, —OR, —$O(CH_2)_n$ aryl, —NRR', —$O(CH_2)_n$-substituted alkyl, —SR, —$O(CH_2)_n$-substituted aryl or —$(CH_2)_n$-cycloalkyl; and $R^{20}$ is H, substituted or unsubstituted alkyl, —OH or —$NH_2$, where the R groups are independently H, alkyl, cycloalkyl—$(CH_2)_n$—, aryl-$(CH_2)_n$—, heteroaryl-$(CH_2)_n$—, or —$(CH_2)(CH_2)_n$—COOH, where the alkyl, cycloalkyl, aryl and heteroaryl moieties are substituted or unsubstituted, then $R^7$ and $R^8$ are both a moiety other than H or Me, or $R^7$ is a moiety other than Cl (including in the cases of pharmaceutically acceptable sals, amides, esters or prodrugs thereof).

Compounds of Formula I thus include compounds having the following structures:

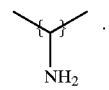

and comprise a number of subgenera of particular interest. Representative subgenera are illustrated in the examples which follow.

One subgenus includes compounds in which at least one $R^4$ moiety is H and at least one $R^3$ moiety is either H or $NH_2$. Compounds of the latter sort include those in which X is

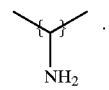

Also of interest are the subgenera of compounds in which the nitrogen atom of the moiety X is further elaborated, as depicted below:

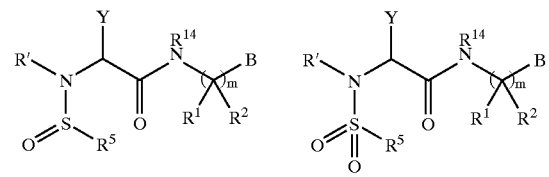

-continued

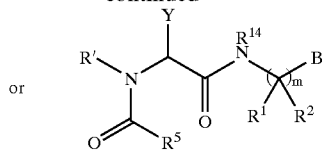

or

Another subgenus includes amides of the formula:

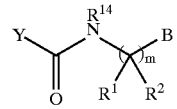

where $R^5$ comprises a substituted or unsubstituted, lower (i.e., containing 1–8 carbon atoms) aliphatic or alkoxyl group, or is a substituted or unsubstituted—$(M)_n$-aryl or —$(M)_n$-heterocyclic (including e.g., substituted and unsubstituted phenyl or benzyl group, or a homolog and heterocyclic analog thereof, including e.g., 2-naphthyl, 3-indolyl, and 1-imidazolyl);

Such compounds are further illustrated by the subset thereof in which $R^5$ comprises —$(M)_nCH_3$, —$(M)_n$aryl, —$(M)_n$heterocyclic, —$(M)_nCN$, —$(M)_nCOOR$, where n is 0, 1, 2, 3, 4, or 5. For instance, in some such compounds $R^5$ is a substituted or unsubstituted methyl, ethyl, n-propyl, i-propyl, n-butyl, sec-butyl, t-butyl, n-pentyl, sec-pentyl, i-pentyl, cyclo pentyl, etc. or benzyl moiety. In other such compounds $R^5$ comprises—$(CH_2)_nCH_3$, —$(CH_2)(CH_2)_n$aryl, —$(CH_2)(CH_2)_n$heterocyclic, —$(CH_2)(CH_2)_nCN$ or —$(CH_2)(CH_2)_nCOOR$, where n again is 0, 1, 2, 3, 4, or 5. Examples of such compounds include those in which $R^5$ comprises —$CH_2CN$, —$(CH_2)CO_2R$, —$(CH_2)_2CO_2R$ —$(CH_2)_3CO_2R$, —$(CH_2)_4CO_2R$, where R is H, lower alkyl or benzyl and those in which $R^5$ comprises —O-substituted or unsubstituted lower alkyl or benzyl).

Another subgenus of interest includes amides of the formula:

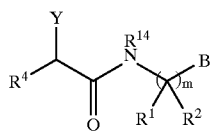

where $R^4$ is hydrogen, substituted or unsubstituted aliphatic (which may be branched, unbranched or cyclic, but preferably does not contain a hyroxamic acid moiety, —NHOR, where R is H, a subsituted or unsubstituted benzyl, trialkylsilyl, t=butyldiphenylsilyl, tetrahydropyranyl or t-butyl group), substituted or unsubstituted aryl-$(M)_n$—, substituted or unsubstituted heterocyclic-$(M)_n$—, or $(CO_2R)(M)_n$—. Such compounds are illustrated by those in which $R^4$ is —$(M)_n(CO)OR$, —$(M)_nSO_2R$, —$(M)_n(CO)NRR'$, or —$(M)_n$(tetrazole), including, for example, compounds in which $R^4$ is —$CH_2COOR$, —$CH_2SO_2R$, —$CH_2(CO)NRR'$, or -tetrazole. Simple members of this subgenus are those in which the R group(s) of $R^4$ is (are independently) H, lower alkyl (e.g., methyl, ethyl, n-propyl, isopropyl, n-butyl, isobutyl, tbutyl, etc.) or benzyl.

Another subgenus includes ureas of the formula:

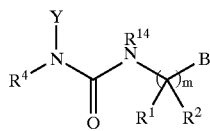

where $R^1$, $R^2$, $R^4$, $R^{14}$, Y and m are defined as above. Thus, $R^4$ may be simply H or may be a more complex $R^4$ moiety such as are noted above.

In many examples of the foregoing compounds, one or more R moieties (R', R" etc) are H.

Also, in many compounds of Formula I of interest, $R^{14}$ is H.

One subgenus of interest includes compounds of Formula I, including the examples described or illustrated above, in which m is 1, $R^1$ is H, and $R^2$ comprises H, HM), H —$(M)_n$-substituted or unsubstituted lower alkyl), —$(M)_n$-substituted or unsubstituted (aryl), —$(M)_n$-subsituted or unsubstituted heterocyclic), —$(M)_nCOOR$, or —$(M)_n(CO)NRR'$. That subclass is illustrated by compounds in which $R^1$ is H, and $R^2$ is methyl, ethyl, i-propyl, n-propyl, n-butyl, isobutyl, n-amyl, sec-amyl, isoamyl, substituted benzyl, $CH_2$-(3indolyl), $CH_2$-(4-imidazolyl), $CH_2CH_2COOR$, $CH_2CH_2CONH_2$, $CH_2COOR$ or $CH_2CONH_2$.

Another subgenus includes compounds of Formula I, including compounds of the sort described or illustrated above, in which $R^1$ and $R^2$ are independently selected, substituted or unsubstituted lower aliphatic groups, usually of 1–8 contiguous carbon E atoms, or $R^1$ and $R^2$ are covalently linked to each other to form a ring, which may be a substituted or unsubstituted, aliphatic or heterocyclic ring or ring system (e.g. a bicyclic moiety), generally containing 3–10 annular atoms. Compounds containing an unsubstituted 3–10-membered ring are illustrated by the following formula, where q is an integer from 1 to 8:

$$Y-X\diagdown_{U}\diagdown_{N}^{H}\diagup\diagdown^{B}_{()_q}$$

Another subgenus includes compounds of Formula I, including the examples described or illustrated above, in which m is 2, and each of $R^1$, $R^{1'}$, $R^2$, and $R^{2'}$ is independently selected from H, —$(M)_nH$, —$(M)_n$(lower alkyl), —$(M)_n$(aryl), —$(M)_n$-(heterocyclic), —$(M)_n$—COOR and —$(M)_n(CO)NRR'$, where the lower alkyl, aryl or heterocyclic moiety is substituted or unsubstituted. In some such compounds, each of $R^1$, $R^{1'}$, $R^2$, and $R^{2'}$ is H.

Another subgenus of compounds of interest are compounds of Formula I, including the examples described or illustrated above, in which at least one of $R^1$ and $R^2$ is methyl, ethyl, i-propyl, n-propyl, n-butyl, isobutyl, n-amyl, sec-amyl, isoamyl, substituted benzyl, —$CH_2$-(3-indolyl), —$CH_2$-(4-imidazolyl), —$CH_2CH_2COOR$, —$CH_2CH_2CONH_2$, —$CH_2COOR$ or —$CH_2CONRR'$, or $R^1$ and $R^2$ are covalently linked to form a ring. In some cases, at least one of $R^1$, $R^{1'}$, $R^2$, and $R^{2'}$ is methyl, ethyl, i-propyl, n-propyl, n-butyl, isobutyl, n-amyl, sec-amyl, isoamyl, substituted benzyl, —$CH_2$-(3-indolyl), —$CH_2$-(4imidazolyl), —$CH_2CH_2COOR$, —$CH_2CH_2CONH_2$, —$CH_2COOR$ or —$CH_2CONRR'$, or two of $R^1$, $R^{1'}$, $R^2$, and $R^{2'}$ are covalently linked to form a ring, which as in other cases, may be a substituted or unsubstituted, aliphatic or heterocyclic ring or ring system (e.g. a bicyclic moiety), generally containing 4–10 annular atoms. Compounds containing 3-, 5- and 6-membered rings are illustrated by the following formulas:

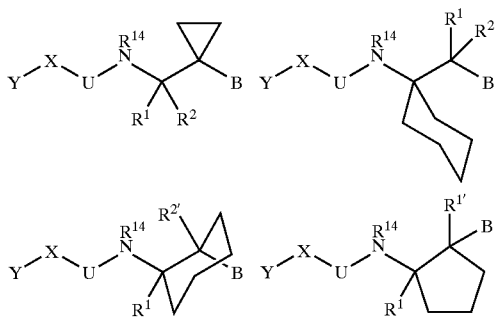

One subgenus of compounds of this invention, i.e., of compounds of Formula I, including among others the members of the various illustrative classes of compounds noted above, includes those compounds of Formula I in which m is 0:

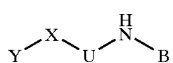

Compounds of Formula I, including, among others, compounds of the various subgenera described above, include those in which Y comprises

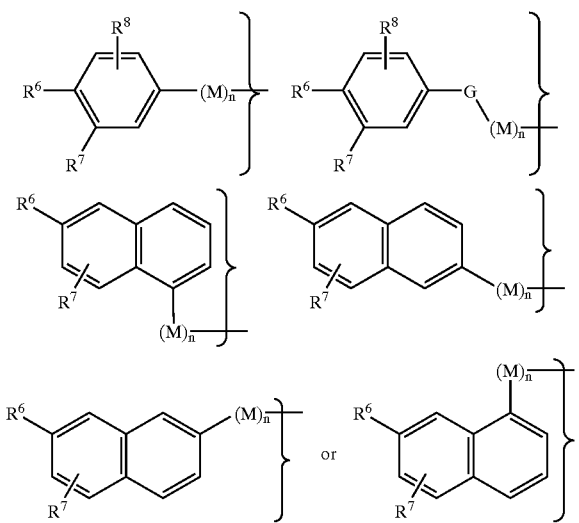

Such compounds in which $R^6$ comprises —$APO_3RR'$, —$OPO_3RR'$, —$ASO_3R$, —$OSO_3R$, —$ACO_2R$, —A-tetrazole, —$ASO_2NRR'$, —$ACOCF_3$, —C(R)(J)(K) or —C(Z)(J)(K); and, $R^7$ and $R^8$ are independently H, —CN, —$NO_2$, halogen, J, —A—$(M)_n$substituted or unsubstituted aliphatic, —$(M)_nCOCF_3$, —$(M)_nOH$, —$(M)_nCOOR$, —A—$(M)_nNRR''$, —$(M)_nCHO$, —A—$(M)_nN(R')(CO)R''$ or —A—$(M)_n$—CO—NRR' are of particular interest. This set of compounds is illustrated by those in which $R^6$ comprises —$APO_3RR'$, —$OPO_3RR'$, —$ACO_2R$, —$ACOCF_3$ or —C(R)(J)(K); A comprises —$M_m$— (e.g., —$CH_2$—, —$CF_2$—, —CHF—, —CHOH—, —$CH_2CF_2$—, etc), —GM— (e.g. —$OCH_2$—) or a covalent bond;

each R and R' is H, or substituted or unsubstituted lower alkyl or substituted or unsubstituted benzyl; and, $R^7$ and $R^8$ are independently H, J, —A—$(M)_n$substituted or unsubstituted aliphatic, —$(M)_nCOCF_3$, —$(M)_nOH$, —$(M)_nCOOR$, —A—$(M)_nNRR'$, —$(M)_nCHO$, —A—$(M)_nN(R)(CO)R'$ or —A—$(M)_nCO$—NRR'. For example, in some such cases, $R^6$ comprises —$PO_3RR'$, —$OPO_3RR'$, —$CH_2PO_3RR'$, —$CF_2PO_3RR'$, —$OCH_2CO_2R$, —$NHCH_2CO_2R$, —$CH_2CO_2R$, —$CF_2CO_2R$, —$CH_2SO_3R$, —$CF_2SO_3R$, —$CH_2COCF_3$, —$CF_2COCF_3$, —$CH(PO_3RR')_2$, —CH(OH)($PO_3RR'$), —$CH(NH_2)(PO_3RR')$, —$CH(CO_2R)_2$, —$CF(CO_2R)_2$, —$CH(PO_3RR')(CO_2R'')$, —$CH(PO_3RR')(SO_3R'')$, —$CH(PO_3RR')(SO_2NH_2)$, —$CH(SO_2NH_2)_2$, or —$CH(SO_3RR')_2$. In some such compounds, one or more of R, R' and R'' in the —$PO_3RR'$, —$OPO_3RR'$, —$CH_2PO_3RR'$, —$CF_2PO_3RR'$, —$OCH_2CO_2R$, —$NHCH_2CO_2R$, —$CH_2CO_2R$, —$CF_2CO_2R$, —$CH_2SO_3R$, —$CF_2SO_3R$, —$CH_2COCF_3$, —$CF_2COCF_3$, —$CH(PO_3RR')_2$, —CH(OH)($PO_3RR'$), —$CH(NH_2)(PO_3RR')$, —$CH(CO_2R)_2$, —$CF(CO_2R)_2$, —$CH(PO_3RR')(CO_2R'')$, —$CH(PO_3RR')(SO_3R'')$, —$CH(PO_3RR')(SO_2NH_2)$, —$CH(SO_2NH_2)_2$, or —$CH(SO_3RR')_2$ moiety is H. In others, one or more of those R groups is —$(M)_m$—$CH_2Z$, —$(M)_m$—$CHZ_2$, —$(M)_m$—$CZ_3$, —$R^{15}$, —M—O—CO—$OR^{15}$ or —M—O—CO—$R^{15}$, where Z is halogen and $R^{15}$ is substituted or unsubstituted lower aliphatic, aryl or heterocyclic. For example, in various embodiments, $R^{15}$ is methyl, ethyl, n-propyl, i-propyl, n-butyl, isobutyl, t-butyl, n-amyl, sec-amyl, benzyl or substituted benzyl, and M is $CH_2$, CHR (e.g. $CHCH_3$ etc.) and the like. Further illustrations include —$CH_2$—O—CO—OEt, —CH(Me)—O—CO—OEt, —$CH_2$—O—CO-t-butyl, etc.

In one subgenus of the foregoing compounds, $R^7$ and $R^8$ are both H. In another subgenus, $R^7$ is J, —$A(M)_n$(aliphatic, aryl or heterocyclic, each of which being substituted or unsubstituted), —$(M)_nCOCF_3$, —$(M)_nOH$, —$(M)_nCOOR$, —A—$(M)_nNRR''$, —$(M)_nCHO$, —A—$(M)_nN(R)(CO)R'$, —A—$(M)_n$—NRR' or —A—$(M)_n$—CO—NRR'; and $R^8$ is H. The latter subgenus is illustrated by compounds in which $R^7$ is lower alkyl, lower alkenyl, —OH, —$NH_2$, —$NO_2$, —CN, —NHR, —NHCOR, —CHO, —$CH_2CHO$, —$PO_3RR'$, —$OPO_3RR'$, —$CH_2PO_3RR'$, $CF_2PO_3RR'$, —$OCH_2CO_2R$, —$NHCH_2CO_2R$, —$CH_2CO_2R$, —$CF_2CO_2R$, —$SO_3R$, —$CH_2SO_3R$, —$CF_2SO_3R$, —$COCF_3$, —$COCH_2F$, —$COCF_2H$, —$CF_2COCF_3$ or —$SO_2NH_2$. In some such compounds, one or both of R and R' in —$PO_3RR'$, —$OPO_3RR'$, —$CH_2PO_3RR'$, —$CF_2PO_3RR'$, —$OCH_2CO_2R$, —$NHCH_2CO_2R$, —$CH_2CO_2R$, —$CF_2CO_2R$, —$SO_3R$, —$CH_2SO_3R$, or —$CF_2SO_3R$ is H. In others, one or more of those R groups is —$(M)_m$—$CH_2Z$, —$(M)_m$—$CHZ_2$, —$(M)_m$—$CZ_3$, —$R^{15}$, —M—O—CO—$OR^{15}$ or —M—O—CO—$R^{15}$, where Z is halogen and $R^{15}$ is substituted or unsubstituted lower aliphatic, aryl or heterocyclic. For example, in individual cases, $R^{15}$ is methyl, ethyl, n-propyl, i-propyl, n-butyl, isobutyl, t-butyl, n-amyl, sec-amyl, benzyl or substituted benzyl, and M is $CH_2$, CHR (e.g. $CHCH_3$ etc.) and the like.

In an illustrative subgenus, $R^6$ comprises —$APO_3RR'$ (e.g., —$OPO_3H_2$) and $R^7$ is —A—$(M)_n$substituted or unsubstituted aliphatic.

In another subgenus, $R^6$ and $R^7$ are independently selected from J and K.

In another subgenus, $R^6$ is —C(R)(J)(K). Illustrative compounds of this subgenus include those in which $R^6$ is —CH(J)(K) and those in which $R^6$ is —C(R)($PO_3R'R''$)(K). The latter compounds are illustrated by embodiments in which none, one, two or three of the R groups of the —C(R)($PO_3R'R''$)(K) moiety are H.

As In previously mentioned cases, compounds of this invention which contain a moiety J, e.g., compounds of Formula I in which $R^6$ is —C(R)(J)(K), include among others embodiments in which one or both of R and R' (e.g., of a —PO$_3$RR' moiety) are R$^{15}$, —(M)$_m$—CH$_2$Z, —(M)$_m$—CHZ$_2$, —(M)$_m$—CZ$_3$, —M—O—CO—OR$^{15}$ or —M—O—CO—R$^{15}$, where Z is halogen and R$^{15}$ is substituted or unsubstituted lower aliphatic, aryl or heterocyclic (e.g., methyl, ethyl, n-propyl, i-propyl, n-butyl, isobutyl, t-butyl, n-amyl, sec-amyl, benzyl or substituted benzyl), and M is CH$_2$, CHR (e.g. CHCH$_3$ etc.) and the like.

One group of compounds of Formula I, including those described by the various subgenera and illustrative examples disclosed herein, all contain a moiety, B, of the formula:

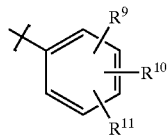

where R$^{9'}$ R$^{10}$ and R$^{11}$ are independently selected from —(M)$_n$R, —G(M$_n$)R, —(M)$_n$Z, —(M)$_n$CN, —(M)$_n$GR, —(M)$_n$NRWR, —(M)$_n$NRW—GR, —(M)$_n$W—R, —G—(M)$_n$W—R, and —(M)$_n$W—GR. Compounds of particular interest include those in which R$^9$ is H or —WGR and R$^{10}$ is —G'M$_n$R', as illustrated by compounds in which R$^9$ is H or —(O)NH$_2$ and R$^{10}$ is an —(CH$_2$)$_n$(aliphatic or cycloaliphatic) moiety. The aliphatic or cycloaliphatic moieties are illustrated by groups such as a substituted or unsubstituted methyl, ethyl, n-propyl, n-butyl, t-butyl, n-pentyl, or benzyl moiety or —CHR$^{16}$R$^{17}$ where R$^{16}$ and R$^{17}$ are independently selected lower aliphatic groups (such as methyl, ethyl, propyl, allyl, butyl, amyl, hexyl, etc) or are covalently linked together forming a cycloaliphatic ring (e.g. cyclopentyl, cyclohexyl, cycloheptyl, etc.). In many such compounds, n is 1 or 2. By way of further illustration, illustrative R$^{10}$ moieties include —OCH$_2$CHMe$_2$, —OCH$_2$CH(Me)(Et), —OCH$_2$CH(Et)$_2$, —OCH$_2$CH(Me)(Propyl), —OCH$_2$CH(Et)(Propyl), —OCH$_2$CH(Et)(Propyl), —OCH$_2$CH(propyl)$_2$, OCH$_2$cyclopentyl, OCH$_2$cyclohexyl or OCH$_2$cycloheptyl. R$^{11}$ may be H or may be any of the generally applicable substituents enumerated elsewhere herein. Compounds of particular current interest include those in which B is configured as follows:

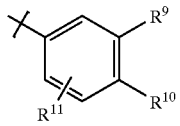

Another group of compounds of Formula I, including those described by the various subgenera and illustrative examples disclosed herein, all contain a moiety, B, of the formula —C(O)NR$^{12}$R$^{13}$. This group is illustrated by compounds in which R$^{12}$ is lower alkyl and R$^{13}$ is aliphatic, —M$_n$-cycloaliphatic, —M$_n$-aryl, —M$_n$-heteroaryl, or —M$_n$CO$_2$R, where the aliphatic, cycloaliphatic, aryl or heteroaryl moiety(ies) is(are) substituted or unsubstituted). Compounds of particular interest include those in which R$^{13}$ is —CH$_2$)$_n$-aliphatic —(CH$_2$)$_n$-cycloaliphatic. In such compounds, n in R$^{13}$ is often 2, 3 or 4.

From the perspective of Y moieties, compounds of particular interest include those compounds of Formula I, including those of the various subgenera and examples herein, which have the following structures:

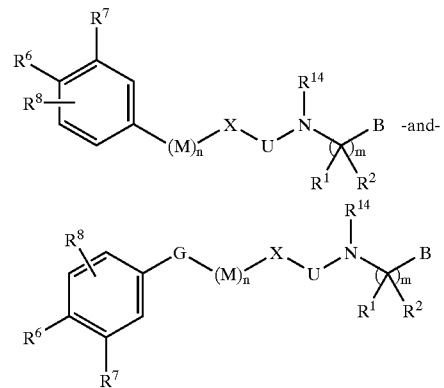

Of special note are compounds in which R$^6$ comprises —PO$_3$RR', —OPO$_3$RR', —OSO$_2$NRR', —(CH$_2$)PO$_3$RR', —(CF$_2$)PO$_3$RR' or —CRJK; R$^7$ comprises R (including among others, H, alkyl, alkenyl, etc.) —CN, amido, acylamino, J (e.g. —O$_2$R), or —CHO, and R$^8$ comprises H or one of the generally applicable substituents mentioned herein. For example, in some cases, R$^6$ comprises —OPO$_3$RR' or —(CF$_2$)PO$_3$RR' and R$^7$ is H. In some embodiments one or more R groups (including R', R", etc) of R$^6$ comprises —(M)$_m$—CH$_2$Z, —(M)$_m$—CHZ$_2$, —(M)$_m$—CZ$_3$—, —R$^{15}$, —M—O—CO—OR$^{15}$ or —M—O—CO—R$^{15}$, where Z is H or halogen and R$^{15}$ is substituted or unsubstituted lower aliphatic, aryl or heterocyclic. For example, in individual cases, R$^{15}$ is methyl, ethyl, n-propyl, i-propyl, n-butyl, isobutyl, t-butyl, n-amyl, sec-amyl, benzyl or substituted benzyl, and M is CH$_2$, CHR (e.g. CHCH$_3$ etc.) and the like.

Compounds of any of the following subgeneric structures are also of special interest:

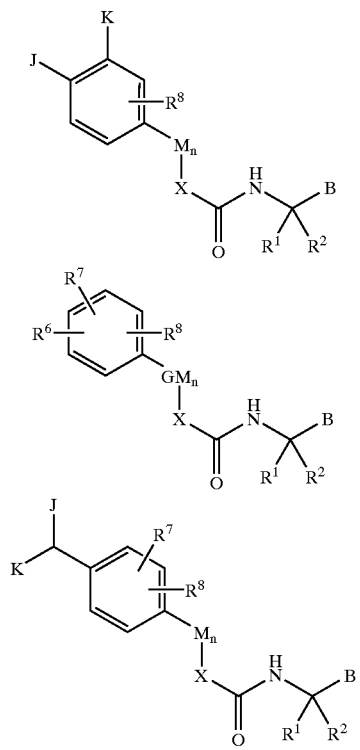

-continued

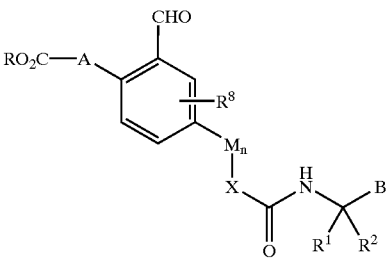

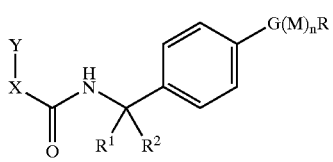

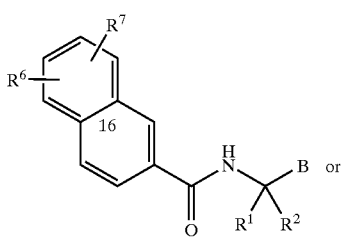

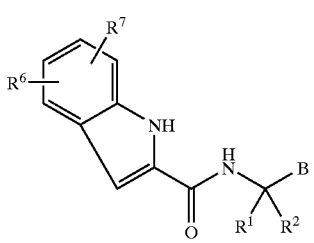

These are illustrated by the following more specific structures:

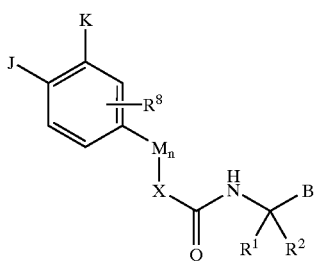

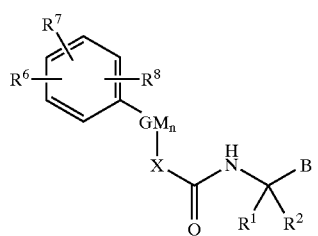

-continued

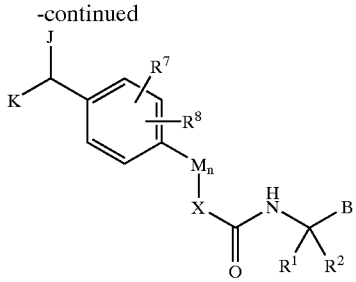

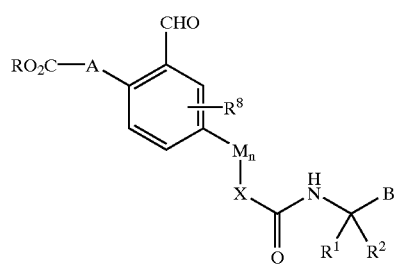

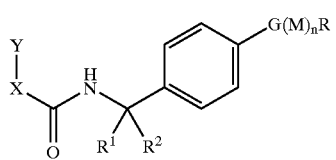

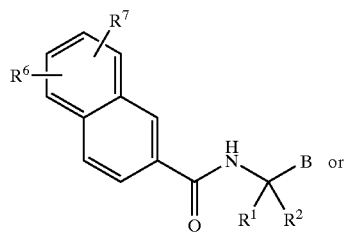

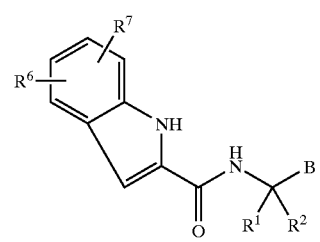

Also of special interest are compounds of the formula:

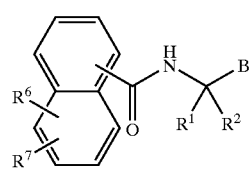

where $R^7$ is not H.

Within these subgenera of special interest individual embodiments include compounds in which at least one of J, K or $R^6$ comprises —$PO_3RR'$, —$OPO_3RR'$, —$MPO_3RR'$, —$OMPO_3RR'$, —$SO_2NRR'$, —$OSO_2NRR'$, —$ACO_2R$, —A-tetrazole, —CZJK or —CRJK. Such cases, are illustrated by compounds in which M is —$CH_2$ or —$CF_2$ or A is a covalent bond or is —$OCH_2$—. In some such cases, J and K are independently selected from the group consisting of —$PO_3RR'$, —COOR, and —$SO_2NRR'$. In some compounds of these subgenera of special interest $R^7$ comprises R, —CN, —$NO_2$, halogen, J, —A—$(M)_n$aliphatic, —G—$(M)_n$aliphatic, —$(M)_n COCF_3$, —$(M)_n OH$, —$(M)_n COOR$, —A—$(M)_n NRR'$, —G—$(M)_q NRR'$, —$(M)_n CHO$, —A—$(M)_n N(R)(CO)R'$, —G—$(M)_q N(R)(CO)R'$, —A—$(M)_n$—CO—NRR', or —G—$(M)_n$CO—NRR', where the aliphatic groups may be substituted or unsubstituted; or $R^8$ is a covalent bond to an $R^4$ substituent of X to form an aliphatic, aryl or heterocyclic ring of 4 to 8 atoms. In particular embodiments of such compounds, $R^7$ comprises H, lower alkyl, lower alkenyl, —CHO or J. In various embodiments, one or more of the R groups (including R', R", etc) of $R^6$ or $R^7$ comprise —$(M)_m$—$CH_2Z$, —$(M)_m$—$CHZ_2$, —$(M)_m$—$CZ_3$, —$R^{15}$, —M—O—CO—$R^{15}$ or —M—O—CO—$OR^{15}$ where Z is halogen and $R^{15}$ is a substituted or unsubstituted lower aliphatic, aryl or heterocyclic group. In some cases, one or more R groups (including R', R", etc) of $R^6$ or $R^7$ is H.

Compounds of this invention which are of special interest include those which bind to a given SH2 domain (or protein containing such SH2 domain) with a $IC_{50}$ value of less than 50 μM, preferably less than 20 μM, as determined by any scientifically valid method, in vitro or in vivo. SH2 domains of current interest include those of a Src, Fyn, Lck, Yes, Blk, Lyn, Fgr, Hck, Yrk, ZAP-70, Syk, STAT or Abl protein.

Also of interest are pharmaceutical compositions comprising a compound of this invention, or a pharmaceutically acceptable derivative thereof, and one or more pharmaceutically acceptable excipients.

Compounds of this invention (or a composition containing such a compound) can be administered to cells or to animals, preferably a mammal in need thereof, as a method for inhibiting SH2-mediated signal transduction therein. In particular cases, it will be advantageous to carry out that method using a pharmaceutical composition containing a compound which specifically binds to an SH2 domain of Src, ZAP-70, Syk, or STAT 6, or which otherwise inhibits signal transduction mediated by the protein of interest. In other cases it will be advantageous to carry out that method where the SH2-mediated signal transduction is mediated by a PDGF receptor protein, EGF receptor protein, HER2/Neu receptor protein, fibroblast growth factor receptor protein, focal adhesion kinase protein, p130 protein, or p68 protein.

Cases in which a mammal may be in need of inhibition of SH2-mediated signaling include cases in which the mammal has a proliferative disease, cancer, restenosis, osteoporosis, inflammation, allergies, or cardiovascular disease. In such cases, administering a therapeutically effective amount of the composition to the mammal, preferably to a human patient, will constitute treating or preventing the proliferative disease, cancer, restenosis, osteoporosis, inflammation, allergic reaction, or cardiovascular disease in the recipient or a method for causing immunosuppression in the recipient.

Generally preferred compounds of this invention include any of the foregoing compounds which yield an observable $IC_{50}$ value, when tested against an SH2 domain of interest and a pTyr-containing peptide ligand (or mimic thereof) for that SH2 domain, of 50 μM or better, preferably 5 μM or better, more preferably 1 μM or better, and even more preferably, 500 nM or better, as determined by any scientifically valid measure, especially when the SH2 domain is from a Src, Fyn, Lck, Yes, Blk, Lyn, Fgr, Hck, Yrk, ZAP, Syk, STAT or Abl protein.

A pharmaceutical composition may be prepared containing a compound of this invention (including a pharmaceutically acceptable derivative thereof) together with one or more pharmaceutically acceptable excipients.

A compound of this invention, preferably in the form of a pharmaceutical composition, may be administered to a mammal in need thereof, preferably a human patient, as a method for inhibiting SH2-mediated signal transduction in the recipient mammal. In some cases, the compound may be selected based on its ability to specifically bind to an SH2 domain, e.g. of Src, ZAP-70, Syk, or STAT 6, etc., or on its ability to inhibit a signal transduction pathway mediated by an SH2 domain-containing protein. Such use of an appropriately selected compound of this invention thus provides a method for inhibiting SH2-mediated signal transduction which is mediated by a PDGF receptor protein, EGF receptor protein, HER2/Neu receptor protein, fibroblast growth factor receptor protein, focal adhesion kinase protein, p130 protein, or p68 protein. Use of a compound of this invention may be particularly advantageous in cases in which the mammal has a proliferative disease, cancer, restenosis, osteoporosis, inflammation, allergies, or cardiovascular disease. In such cases, administering to the patient a therapeutically effective amount of a compound of this invention, preferably in the form of a pharmaceutical composition, provides a method for treating or preventing a proliferative disease, cancer, restenosis, osteoporosis, inflammation, allergies, or cardiovascular disease in the patient.

DETAILED DESCRIPTION OF THE INVENTION

Compounds and Definitions

As mentioned above, this invention provides a novel class of compounds useful as inhibitors of signal transduction pathways mediated by the interaction of protein receptors for phosphotyrosine-containing proteins, such as proteins containing one or more SH2 domains, with their phosphotyrosine-containing ligands. Compounds of this invention comprise those of Formula I, set forth above, and are illustrated in part by the various classes, subgenera and subsets of compounds noted above, and by the various subgenera and species disclosed elsewhere herein. The compound may be in the form of an individual enantiomer, diastereomer or geometric isomer, or may be in the form of a mixture of stereoisomers.

Also included are pharmaceutically acceptable derivatives of the foregoing compounds, where the phrase "pharmaceutically acceptable derivative" denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof, preferably one which is a signal transduction inhibitor. Pharmaceutically acceptable derivatives thus include among others pro-drugs. A pro-drug is a derivative of a compound, usually with significantly reduced pharmacological activity, which contains an additional moiety which is susceptible to removal in vivo yielding the parent molecule as the pharmacologically active species. An example of a pro-drug is an ester which is cleaved in vivo to yield a compound of interest. Pro-drugs of a variety of compounds, and materials and methods for derivatizing the parent compounds to create the pro-drugs, are known and may be adapted to the present invention.

The term "aliphatic" as used herein includes both saturated and unsaturated, straight chain (i.e., unbranched), branched, cyclic, or polycyclic aliphatic hydrocarbons, which are optionally substituted with one or more functional groups. Unless otherwise specified, alkyl, other aliphatic, alkoxy and acyl groups preferably contain 1–8, and in many cases 1–6, contiguous aliphatic carbon atoms, Illustrative aliphatic groups thus include, for example, methyl, ethyl, n-propyl, isopropyl, cyclopropyl, —CH$_2$-cyclopropyl, allyl, n-butyl, sec-butyl, isobutyl, tert-butyl, cyclobutyl, —CH$_2$-cyclobutyl, n-pentyl, sec-pentyl, isopentyl, tert-pentyl, cyclopentyl, —CH$_2$-cyclopentyl, n-hexyl, sec-hexyl, cyclohexyl, —CH$_2$-cyclohexyl moieties and the like, which again, may bear one or more substituents.

Some examples of substituents of aliphatic (and other) moieties of compounds of this invention include: R, —OH, —OR, —SH, —SR, —CHO, =O, —COR, —COOH (or amide, ester, carbamate, urea, oxime or carbonate thereof), —NH$_2$ (or substituted amine, amide, urea, carbamate or guanidino derivative therof), halo, trihaloalkyl, cyano, —SO$_2$—CF$_3$, —OSO$_2$F, —OS(O)$_2$R, —SO$_2$—NHR, —NHSO$_2$R, sulfate, sulfonate, aryl and heteroaryl moieties. Aliphatic, heteraliphatic, aryl and heterocyclic substituents may themselves be substituted or unsubstituted (e.g. mono-, di- and tri-alkoxyphenyl; methylenedioxyphenyl or ethylenedioxyphenyl; halophenyl; or -phenyl-C(Me)$_2$—CH$_2$—O—CO—[C3–C6] alkyl or alkylamino). Additional examples of generally applicable substituents are illustrated by the specific embodiments shown in the Examples which follow.

The term "aliphatic" is thus intended to include alkyl, alkenyl, alkynyl, cycloalkyl, cycloalkenyl, and cycloalkynyl moieties.

As used herein, the term "alkyl" includes both straight, branched and cyclic alkyl groups. An analogous convention applies to other generic terms such as "alkenyl", "alkynyl" and the like. Furthermore, as used herein, the language "alkyl", "alkenyl", "alkynyl" and the like encompasses both substituted and unsubstituted groups.

The term "alkyl" refers to groups usually having one to eight, preferably one to six carbon atoms. For example, "alkyl" may refer to methyl, ethyl, n-propyl, isopropyl, cyclopropyl, butyl, isobutyl, sec-butyl, tert-butyl, cyclobutyl, pentyl, isopentyl tert-pentyl, cyclopentyl, hexyl, isohexyl, cyclohexyl, and the like. Suitable substituted alkyls include, but are not limited to, fluoromethyl, difluoromethyl, trifluoromethyl, 2-fluoroethyl, 3-fluoropropyl, hydroxymethyl, 2-hydroxyethyl, 3-hydroxypropyl, benzyl, substituted benzyl and the like.

The term "alkenyl" refers to groups usually having two to eight, preferably two to six carbon atoms. For example, "alkenyl" may refer to prop-2-enyl, but-2-enyl, but-3-enyl, 2-methylprop-2-enyl, hex-2-enyl, hex-5-enyl, 2,3-dimethylbut-2-enyl, and the like. The language "alkynyl," which also refers to groups having two to eight, preferably two to six carbons, includes, but is not limited to, prop-2-ynyl, but-2-ynyl, but-3-ynyl, pent-2-ynyl, 3-methylpent-4-ynyl, hex-2-ynyl, hex-5-ynyl, and the like.

The term "cycloalkyl" as used herein refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of other aliphatic or heteroaliphatic or heterocyclic moieties, may optionally be substituted.

The term "heteroaliphaic" as used herein refers to aliphatic moieties which contain one or more oxygen, sulfur, nitrogen, phosphorous or silicon atoms, e.g., in place of carbon atoms. Heteroaliphatic moieties may be branched, unbranched or cyclic and include heterocycles such as morpholino, pyrrolidinyl, etc.

The term "heterocycle" as used herein refers to cyclic heteroaliphatic and heteroaryl groups and preferably three to ten ring atoms total, Includes, but is not limited to heteroaliphatic moieties such as oxetane, tetrahydrofuranyl, tetrahydropyranyl, aziridine, azetidine, pyrrolidine, piperidine, morpholine, piperazine and the like, and heteroaryl moieties as described below.

The terms "aryl" and "heteroaryl" as used herein refer to stable mono- or polycyclic, heterocyclic, polycyclic, and polyheterocyclic unsaturated moieties having 3–14 carbon atom which may be substituted or unsubstituted. Substituents include any of the previously mentioned substituents. Non-limiting examples of useful aryl ring groups include phenyl, halophenyl, alkoxyphenyl, dialkoxyphenyl, trialkoxyphenyl, alkylenedioxyphenyl, naphthyl, phenanthryl, anthryl, phenanthro and the like. Examples of typical heteroaryl rings include 5-membered monocyclic ring groups such as thienyl, pyrrolyl, imidazolyl, pyrazolyl, furyl, isothiazolyl, furazanyl, oxazolyl, isoxazolyl, thiazolyl, oxadiazolyl and the like; 6-membered monocyclic groups such as pyridyl, pyrazinyl, pyrimidinyl, pyridazinyl, triazinyl and the like; and polycyclic heterocyclic ring groups such as benzo[b]thienyl, naphtho[2,3-b]thienyl, thianthrenyl, isobenzofuranyl, chromenyl, xanthenyl, phenoxathienyl, indolizinyl, isoindolyl, indolyl, indazolyi, purinyl, isoquinolyl, quinolyl, phthalazinyl, naphthyridinyl, quinoxalinyl, quinazolinyl, benzothiazole, benzimidazole, tetrahydroquinoline cinnolinyl, pteridinyl, carbazolyl, beta-carbolinyl, phenanthridinyl, acridinyl, perimidinyl, phenanthrolinyl, phenazinyl, isothiazolyl, phenothiazinyl, phenoxazinyl, and the like(see e.g. Katritzky, Handbook of Heterocyclic Chemistry). The aryl or heteroaryl moieties may be substituted with one to five members selected from the group consisting of hydroxy, C1–C8 alkoxy, C1–C8 branched or straight-chain alkyl, acyloxy, carbamoyl, amino, N-acylamino, nitro, halo, trihalomethyl, cyano, and carboxyl. Aryl moieties thus include, e.g. phenyl; substituted phenyl bearing one or more substituents selected from groups including: halo such as chloro or fluoro, hydroxy, C1–C6 alkyl, acyl, acyloxy, C1–C6 alkoxy (such as methoxy or ethoxy, including among others dialkoxyphenyl moieties such as 2,3-, 2,4-, 2,5-, 3,4- or 3,5-dimethoxy or diethoxy phenyl or such as methylenedioxyphenyl, or 3-methoxy-5-ethoxyphenyl; or trisubstituted phenyl, such as trialkoxy (e.g., 3,4,5-trimethoxy or ethoxyphenyl), 3,5-dimethoxy-4-chloro-phenyl, etc.), amino, —SO$_2$NH$_2$, —SO$_2$NH (aliphatic), —SO$_2$N(aliphatic)$_2$, —O-aliphatic-COOH, and —O-aliphatic-NH$_2$ (which may contain one or two N-aliphatic or N-acyl substituents).

A "halo" substituent may be fluoro, chloro, bromo or iodo.

With respect to nomenclature, note that asymmetric moieties such as "—G—M—" are written in the direction or order in which they are intended to be read into a given structure. Thus, "—G—M—" is distinct from "—M—G—". For example, in "Ar—A—COOR", where A is —G—M—, the structure Ar—G—M—COOR, not Ar—M—G—COOR, is intended.

Synthesis

Those of ordinary skill in this art will appreciate that compounds of this invention may be produced using any of a variety of synthetic strategies. We typically use a convergent synthetic scheme in which an intermediate comprising the desired "YXU" moiety, protected as appropriate, is condensed with a second intermediate comprising the desired amino moiety HR$^{14}$N(CR$^1$R$^2$)$_m$B, again, protected as appropriate, to yield (following any necessary deprotection steps) the desired compound of Formula I. A variety of methods and materials for effecting the relevant chemical transformations, product recovery, purification and formulation are known in the art which may be adapted to use in the practice of this invention. The detailed examples which follow illustrate such syntheses and should provide helpful guidance to the practitioner.

Assays for Comparative Functional Evaluation of Compounds

Compounds of this invention may be evaluated in a variety of assays to determine their relative ability to bind to a receptor for a pTyr-containing ligand, such as a protein containing one or more SH2 or PI domains, or to otherwise inhibit an intermolecular interaction mediated by such a domain. See e.g. U.S. Pat. No. 5,667,980 (Pawson; competitive binding assays), PCT/US97/02635 (Rickles et al; cell-based assays) and PCT/US/97/06746 (Lynch et al, FP assays). Compounds may also be evaluated for their selectivity of binding to one such receptor (or family of receptors) relative to another such receptor (or family of receptors). The compounds of this invention can be further evaluated by conventional methods for possible therapeutic applications, including evaluations of toxicological and pharmacological activity. For example, the compounds may further be evaluated for activity in inhibiting cellular or other biological events mediated by a pathway involving the molecular interaction of interest using a suitable cell-based assay or an animal model. Cell-based assays and animal models suitable for evaluating inhibitory activity of a test compound with respect to a wide variety of cellular and other biological events are known in the art. New assays and models are regularly developed and reported in the scientific literature.

By way of non-limiting example, compounds which bind to an SH2 domain involved in the transduction of a signal leading to asthma or allergic episodes may be evaluated in a mast cell or basophil degranulation assay. The inhibitory activity of a test compound identified as an SH2 inhibitor by the method of this invention with respect to cellular release of specific mediators such as histamine, leukotrienes, hormonal mediators and/or cytokines, as well as its biological activity with respect to the levels of phosphatidylinositol hydrolysis or tyrosine phosphorylation can be characterized with conventional in vitro assays as an indication of biological activity. [See, e.g., Edward L. Barsumian et al, *Eur. J. Immunol.*, 11:317–323 (1981); M. J. Forrest, *Biochem. Pharmacol.*, 42:1221–1228 (1991) (measuring N-acetyl-betaglucosamin-adase from activated neutrophils); and Stephan et al., *J. Biol. Chem.*, 2:5434–5441 (1992)].

For example, histamine release can be measured by a radioimmunoassay using a kit available from AMAC Inc. (Westbrook, Me.). One can thus evaluate the biological activity of compounds of this invention and compare them to one another and to known active compounds or clinically relevant compounds which can be used as positive controls.

Generally speaking, in such assays IC50 scores of 20 $\mu$M or less are considered of special interest, scores below 1 $\mu$M are considered of particular interest and scores below about 500 nM are of high interest Inhibitors of this invention may also be tested in an ex vivo assay, e.g., for their ability to block antigen-stimulated contraction of sensitized guinea pig tracheal strip tissue. Activity in this assay has been shown to be useful in predicting the efficacy of potential anti-asthma drugs.

Numerous animal models of asthma have been developed and can be used [for reviews, see Larson, "Experimental Models of Reversible Airway Obstruction", in THE LUNG, Scientific Foundations, Crystal, West et al. (eds.), Raven Press, New York, pp. 953–965 (1991); Warner et al., *Am. Rev. Respir. Dis.*, 141:253–257 (1990)]. Species used in animal models of asthma include mice, rats, guinea pigs, rabbits, dogs, sheep and primates. Other in vivo models available are described in Cross et al., *Lab Invest.*, 63:162–170 (1990); and Koh, et al., *Science*, 256:1210–1213 (1992).

By way of further example, compounds which bind to an SH2 or other domain of interest involved in the transduction of a signal involved in the initiation, maintenance or spread of cancerous growth may be evaluated in relevant conventional in vitro and in Vivo assays. See e.g., Ishii et al., *J. Antibiot.*, XLII:1877–1878 (1989); and U.S. Pat. No. 5,206,249 (issued Apr. 27, 1993).

Compounds which bind to a ZAP SH2 domain or which otherwise inhibit ZAP-70-mediated signaling may be evaluated for immunosuppressive activity, e.g., in any of the well-known in vitro or in vivo immunosuppression assays.

Compounds which bind to a Src SH2 domain or which otherwise inhibit Src-mediated signaling may be evaluated for activity in a variety of assays considered predictive of activity in treating or preventing osteoporosis. Such assays include the various pit assays and calvaria assays, among others. Illustrative assays are described below.

Murine Calvaria Assay

In osteoporosis, excessive bone resorption results in decreased bone density. In vivo and in vitro models of bone resorption are used to study the processes leading to osteoporosis. In vitro, fetal rat long bone and murine calvaria cultures are routinely used. Both models display similar responses to parathyroid hormone (PTH), a physiological modulator of bone resorption (Stem, P. H. and N. S. Krieger. Comparison of fetal rat limb bones and neonatal mouse calvaria: effects of parathyroid hormone and 1,25-dihydroxyvitamin $D_3$. Calcif. Tissue Int. 35: 172–176, 1983). The calvaria model of bone resorption can be successfully used to screen osteotropic compounds as has been previously shown (Green, J. R., K. Muller and K. Jaeggi. Preclinical pharmacology of CGP 42'446, a new, potent, heterocyclic bisphosphonate compound. J. Bone Miner. Res. 9: 745–751, 1994.).

In one modification of the conventional calvaria model, calvaria are not labeled with $^{45}Ca^{++}$. Instead, calvarial calcium release into the media is assessed using a microtiter colorimetric calcium assay. This modification can yield more consistent responses than the radioactive methodology and provides results which are comparable to literature values for $^{45}Ca^{++}$ assays.

One calvaria culture model tests the ability of anti-resorptive compounds to prevent resorption (prophylactic model). A second model tests the ability of these compounds to terminate ongoing resorption (therapeutic model). Cytotoxicity may be assessed in both models using a lactate dehydrogenase (LDH) assay. These in vitro models of bone resorption may be used for routine screening and evaluation of compounds for their ability to alter osteoclast-mediated bone resorption.

Media Preparation

Calcium free Dulbecco's Modified Eagle's Medium (DMEM) may be obtained in a 5× solution (Specialty Media, D-012). A 1× solution is prepared using ultrafiltered water. A suitable media contains 15% heat inactivated horse serum (Sigma, H 1270). Calcium concentration is adjusted to 1.65 to 1.83 mM using 02 M $CaCl_2$. Penicillin (100 U/ml) and streptomycin (0.1 mg/ml) are added to the final media preparation. Indomethacin is prepared to 0.5 mg/ml (1.39× $10_{-7}$ M) in ethanol, and is added to an aliquot of DMEM to produce a final concentration of 0.5 μM. Bovine parathyroid hormone (1–34) may be obtained from Bachem (PCAL 100). PTH is solubilized in 0.1% BSA and is then diluted in DMEM to produce a final concentration of $10^{-6}$ M PTH. Ten-told serial dilutions are performed down to $10^{-11}$ M.

Calvaia Dissection

Pregnant CD-1 mice may be obtained from Charles River and are subjected to parturition. Neonatal mice (4–6 days) are cleansed with betadine and then euthanized by decapitation. Adherent skin is cleared away from the skull, exposing the calvaria. The calvaria are dissected away from the skull using a 12B scalpel. Calvaria are immediately placed into a glass petri dish containing room temperature Tyrode's Salt Solution (Sigma, T-2397). The calvaria are trimmed free of cartilage and bisected with a scalpel along the sagital suture. After dissection of all calvaria, calvaria are transferred into 24 well plates containing 0.5 μM indomethacin (Sigma, I-7378).

Culture Conditions

Calvaria are incubated in 1.5 ml DMEM in 24 well tissue culture plates at 37° C., 5% $CO_2$/air. Plates are rocked in the incubator using a Belico rocker platform. Calvaria are pre-incubated in 0.5 μM indomethacin for 24 hours. For each experiment, 6 to 8 random calvaria halves are used for each group. Both halves from a single mouse are never in the same group. Experiments are repeated at least three times.

Prophylactic Calvaria Experiment

After the 24 h pre-incubation period, calvaria are thoroughly washed in indomethacin-free DMEM. Calvaria are then transferred to new wells containing various PTH concentrations, and are cultured for an additional 72 hours. Media samples (30 μl) are obtained every 24 hours and assayed for calcium and LDH activity.

Therapeutic Calvaria Experiment

At the end of the 24 h pre-incubation period, the calvaria are washed free of indomethacin using DMEM. Calvaria are then transferred to new wells containing DMEM or various concentrations of PTH. After 24 hours calvaria are transferred into new wells with fresh media (PTH or DMEM) and cultured an additional 48 hours before addition of control vehicle. This may be accomplished by adding 3 μl of DMSO to new wells, and transferring each calvaria along with its media into wells. Culture continues for a further 24 hours. Media samples are obtained after 72 hours and 96 hours in culture with PTH and assayed for calcium. Additional samples are obtained after 48, 72, and 96 hours in culture with PTH and assayed for LDH.

Calcium Assay

A commercially available diagnostic calcium assay (Sigma, No. 588-3), modified for use in a microtiter format, may be used to determine circulating serum calcium concentrations. This colorimetric assay is dependent on the specific, high affinity complexation of calcium with arsenazo III dye under acidic conditions, which occurs with 1:1 stoichiometry and absorbs at 600 nm (Bauer, P. J. Affinity and stoichiometry of calcium binding by Arsenazo III. Anal Biochem, 110:61, 1981, Michaylova, V and P Ilkova. Photometric determination of micro amounts of calcium with Arsenazo III. Anal Chim Acta, 53: 194, 1971). Magnesium has very low affinity for arsenazo III.

Briefly, 15 μl of media or rat sera (see below) is diluted 18-fold with ultrafiltered water (nearly calcium-free). Fifty μl of this solution are pipetted into microtiter wells (Nunc, Maxisorp, flat-bottom, 0.4 ml/well). Standards of 0, 0.5, 1, 2.5, 3.75, 5, 6.25, and 7.5 mg/dl (mg%) calcium, diluted 8-fold with ultrafiltered water from control standards (Sigma, 360-11), are used to construct standard curves. Once all standards and samples are pipetted onto the plate, 150 μl of diagnostic reagent is added to initiate complexation. Optical density measurements are obtained on a microtiter plate reader (Molecular Devices, ThermoMax) at 600 nm.

Lactate Dehydrogenase Assay

Phosphate buffer is prepared in distilled water (0.26 M $K_2HPO_4.3H_2O$, 0.26 M $KH_2PO_4$; pH 7.4). A mix consisting of: 22 ml of phosphate buffer, 6 ml distilled water and 2.0 ml of 0.01 M pyruvate is prepared. NADH is prepared to 0.4 mg/ml in phosphate buffer.

Ten μl of media samples obtained from incubated calvaria are added to 96 well plates. Wells containing 10 μl of DMEM serve as blanks. To each well, 90 μl distilled water and 150 μl phosphate mix is added. 50 μl NADH is added using an eight channel pipette immediately before the plate is read on a microtiter plate reader at 340 nm. A kinetic assay is performed for 10 minutes, with a read interval of 20 seconds.

Thyroid/parathyroidectomized Rat Model of Bone Resorption

Parathyroid hormone (PTH) replacement in thyroparathyroidectomized (TPTX) rats is routinely used as an in vivo model of controlled bone resorption. Rats are the species of choice since the mechanisms of bone modeling in the rat resemble those in humans. In addition, hormones and pharmacologic agents have similar effects on both rat and human bone (Frost, H. M. and W. S. S. Jee. On the rat model of human osteopenias and osteoporoses. Bone and Mineral, 18: 227–236, 1992). Removal of the thyroid and parathyroid glands results in a rapid loss of parathyroid hormone (PTH) from the circulation. Since PTH induces osteoclast-mediated bone resorption, this process is inhibited in TPTX animals. In addition, PTH mediates calcium reabsorption from the kidneys and absorption from the small intestines. The lack of these activities work in concert to decrease serum calcium levels. In the absence of PTH, rats remain in a hypocalcemic state. Restriction of dietary calcium limits intestinal calcium absorption and renal calcium filtration such that serum calcium levels are primarily influenced by bone resorption. Controlled PTH replacement therapy results in a controlled return of serum calcium to baseline levels. When replacement occurs, concomitantly with a low calcium diet, serum calcium increase is due to PTH-induced osteoclast-mediated bone resorption.

In this model, drugs which inhibit bone resorption prevent the PTH-mediated return of serum calcium to baseline levels.

Female Wistar rats (226–250 gm, Charles River) are fasted overnight and anesthetized with 0.15 ml of 1.2% tribromoethanol (TBE). The ventral neck area is shaved and swabbed with betadine and isopropanol. A midline incision is made in the neck through the skin and superficial muscle layer, as well as in the stemohyoid muscle. Blunt dissection is performed to expose the thyroid gland. The thyroid gland is carefully isolated from the trachea, thyrohyold muscle, as well as adjacent nerves and blood vessels, using blunt dissection. The thyroid gland is excised one lobe at a time. Cautery is performed for hemostasis. Care is taken to avoid damaging the recurrent laryngeal nerve since damage to it is shown to affect serum calcium concentrations (Hirsch, P. F., G. F. Gauthier and P. L. Munson. Thyroid hypocalcemic principle and recurrent laryngeal nerve injury as factors affecting the response to parathyroidectomy in rats. Endocrinology, 73: 244–252, 1963. et al., 1963). The incisions are closed using 3-0 vicryl. The wound is coated with triple antibiotic ointment (Fougera; 400 units/g bacitracin zinc, 5 mg/g neomycin sulfate, 5000 units/g polymyxin B sulfate). Following TPTX, rats are pair fed a low calcium diet (Harlan Teklad TD 95065; $\leq 0.003\%$ $Ca^{++}$, $\leq 0.04\%$ $PO_4$) such that each rat receives the same quantity of food. Rats are fed at least 5 grams, but not more than 10 grams, of food. Rats consuming less than 3.0 grams of food receive the nutritional supplement Nutri-Cal p.o. (Evsco; $\leq 0.0033\%$ calcium).

PTH Dose Response/Pump Implantation

Three days post TPTX, rats which are found to be hypocalcemic, based on day 2 serum calcium levels, are implanted with PTH-containing Alzet mini-osmotic pumps (ALZA, model 2001D) which pumps at a rate of 1 $\mu l/h$. The rats are anesthetized with ketamine (50 mg/kg, i.p.) and acepromazine (1.67 mg/kg, i.p.). The scapula region is shaved and prepared for surgery with betadine and isopropanol. A lateral incision of approximately 2 cm in length is made between the scapulae. Using hemostats, a subcutaneous pocket is created into which the Alzet pump is inserted. The wound is closed either with nylon suture or with staples. Triple antibiotic ointment is applied as described previously.

Bovine parathyroid hormone 1–34 (PTH) (Bachem Calif., PCAL100) is prepared In vehicle ($10^{-3}$ N HCl, 0.15 M NaCl, 20 mg/ml cysteine-HCl) at the following concentrations: 0.156, 0.47, 1.56, 4.7, 15.6, and 156 $\mu M$. Alzet mini-osmotic pumps are filled with the PTH solution and maintained in 37° C. saline for 4 hours prior to implantation.

Serum Samples

Rats are anesthetized by $CO_2$ from dry ice and daily blood samples are obtained via cardiac puncture using a 27 gauge needle. Baseline samples are taken just prior to TPTX. Daily samples are obtained in the morning. Samples are allowed to clot on their side for several hours and subsequently spun at 1000×g for 15 minutes to obtain serum. Serum is aliquoted and stored in the refrigerator until assayed for serum calcium. Serum calcium is measured (see above) daily for at least 7 days following TPTX.

Uses of Compounds of This Invention

Compounds of this invention which bind to an SH2 domain of interest may be used as biological reagents in assays as described herein for functional classification of a pTyr-binding domain (e.g. SH2 or PI domain) of a particular protein, particularly a newly discovered protein. Families or classes of such proteins which bind to pTyr-containing ligands may now be defined functionally, with respect to ligand specificity. Moreover, compounds of this invention can be used to inhibit the occurrence of biological events resulting from molecular Interactions mediated by the protein of interest. Inhibiting such interactions can be useful in research aimed at better understanding the biology of events mediated by the binding of pTyr-containing ligands to their receptors.

Such compounds would be useful, for example, in the diagnosis, prevention or treatment of conditions or diseases resulting from a cellular processes mediated by the binding of a pTyr-containing ligand with a receptor therefor. For example, a patient can be treated to prevent the occurrence or progression of osteoporosis or to reverse its course by administering to the patient in need thereof an SH2inhibitor which selectively binds Src SH2 or otherwise interferes with Src-mediated signaling.

There are many other conditions for which such signal transduction inhibitors may be useful therapeutically, including, e.g., breast cancer where the SH2 domain-containing proteins Src, PLCgamma and Grb7 have been implicated. Other relevant conditions include prostate cancer, in which case targeting Grb2, PLCgamma, and PI3K, all of which contain SH2 domains, may be useful in treatment or prevention of the disease. Inhibition of the interaction of Grb2 or Abl SH2 domains with BCR-abl may be useful to treat chronic myelogenous leukemia (CML) or acute myelogenous leukemia (AML).

Still other relevant applications include the prevention of interferon-, growth factor-, or cytokine-mediated diseases (e.g. Inflammatory diseases) by targeting the interaction of STAT proteins with their pTyr-containing ligands or otherwise inhibiting their signal transduction pathways. Agents that block the SH2 domains of ZAP-70, or which otherwise inhibit ZAP-70-mediated signaling, would be candidates for the treatment of immune-related disorders such as rejection of transplanted bone marrow, skin or other organs; rheumatoid arthritis; inflammatory bowel disease; and systemic lupus erythmatosis, and a variety of autoimmune diseases.

By virtue of the capacity to inhibit protein-protein interactions or a relevant kinase or phosphatase activity required for cellular events of pharmacologic importance, compounds of this invention which inhibit cellular signal transduction may be used in pharmaceutical compositions and methods for treatment or prevention in a subject in need thereof. Such inhibitors can be used to treat or reduce the risk of the diseases or their pathological effects mediated by such interactions.

For example, drugs that completely block one of the two ZAP SH2 domains should effectively prevent ZAP from associating with the activated TCR and thus block T cell activation. A ZAP antagonist or inhibitor would specifically inhibit T cells and avoid the toxicity of the currently used immunosuppressive drugs, FK506 and cyclosporin, which target the more ubiquitously expressed protein, calcineurin. Since calcineurin is required for cellular activities in several tissues in addition to T cells, cyclosporin and FK506 cause side effects in the kidney and central nervous system which limit their application largely to patients with organ transplant rejection.

Therapeutic/prophylactic Administration & Pharmaceutical Compositions

Compounds of this invention can exist in free form or, where appropriate, in salt form. Pharmaceutically acceptable salts of many types of compounds and their preparation are well-known to those of skill in the art. The pharmaceutically acceptable salts of compounds of this invention include the conventional non-toxic salts or the quaternary ammonium salts of such compounds which are formed, for example, from inorganic or organic acids of bases.

The compounds of the invention may form hydrates or solvates. It is known to those of skill in the art that charged compounds form hydrated species when lyophilized with water, or form solvated species when concentrated in a solution with an appropriate organic solvent.

This invention also relates to pharmaceutical compositions comprising a therapeutically (or prophylactically) effective amount of the compound, and a pharmaceutically acceptable carrier or excipient. Carriers include e.g. saline, buffered saline, dextrose, water, glycerol, ethanol, and combinations thereof, and are discussed in greater detail below. The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Formulation may involve mixing, granulating and compressing or dissolving the ingredients as appropriate to the desired preparation.

The pharmaceutical carrier employed may be, for example, either a solid or liquid.

Illustrative solid carrier include lactose, terra alba, sucrose, talc, gelatin, agar, pectin, acacia, magnesium stearate, stearic acid and the like. A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Illustrative liquid carriers include syrup, peanut oil, olive oil, water, etc. Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carders are useful in sterile liquid form compositions for parenteral administration. The liquid carrier for pressurized compositions can be halogenated hydrocarbon or other pharmaceutically acceptable propellant. Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

The carrier or excipient may include time delay material well known to the art, such as glyceryl monostearate or glyceryl distearate along or with a wax, ethylcellulose, hydroxypropylmethylcellulose, methylmethacrylate and the like. When formulated for oral administration, 0.01% Tween 80 in PHOSAL PG-50 (phospholipid concentrate with 1,2-propylene glycol, A. Nattermann & Cie. GmbH) has been recognized as providing an acceptable oral formulation for other compounds, and may be adapted to formulations for various compounds of this invention.

A wide variety of pharmaceutical forms can be employed. If a solid carrier is used, the preparation can be tableted, placed in a hard gelatin capsule in powder or pellet form or in the form of a troche or lozenge. The amount of solid carrier will vary widely but preferably will be from about 25 mg to about 1 g. If a liquid carrier is used, the preparation will be in the form of a syrup, emulsion, soft gelatin capsule, sterile injectable solution or suspension in an ampule or vial or nonaqueous liquid suspension.

To obtain a stable water soluble dosage form, a pharmaceutically acceptable salt of the compound may be dissolved in an aqueous solution of an organic or inorganic acid, such as a 0.3M solution of succinic acid or citric acid. Alternatively, acidic derivatives can be dissolved in suitable basic solutions. If a soluble salt form is not available, the compound is dissolved in a suitable cosolvent or combinations thereof. Examples of such suitable cosolvents include, but are not limited to, alcohol, propylene glycol, polyethylene glycol 300, polysorbate 80, glycerin, polyoxyethylated fatty acids, fatty alcohols or glycerin hydroxy fatty acids esters and the like in concentrations ranging from 0–60% of the total volume.

Various delivery systems are known and can be used to administer the compound, or the various formulations thereof, including tablets, capsules, injectable solutions, encapsulation in liposomes, microparticles, microcapsules, etc. Methods of introduction include but are not limited to dermal, intradermal, intramuscular, intraperitoneal, intravenous, subcutaneous, intranasal, pulmonary, epidural, ocular and (as is usually preferred) oral routes. The compound may be administered by any convenient or otherwise appropriate route, for example by infusion or bolus injection, by absorption through epithelial or mucocutaneous linings (e.g., oral mucosa, rectal and intestinal mucosa, etc.) and may be administered together with other biologically active agents. Administration can be systemic or local. For treatment or prophylaxis of nasal, bronchial or pulmonary conditions, preferred routes of administration are oral, nasal or via a bronchial aerosol or nebulizer.

In certain embodiments, it may be desirable to administer the compound locally to an area in need of treatment; this may be achieved by, for example, and not by way of limitation, local infusion during surgery, topical application, by injection, by means of a catheter, by means of a suppository, or by means of a skin patch or implant, said implant being of a porous, non-porous, or gelatinous material, including membranes, such as sialastic membranes, or fibers.

In a specific embodiment, the compositon is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic to ease pain at the side of the injection. Generally, the ingredients are supplied either separately or mixed together in unit dosage form, for example, as a lyophilized powder or water free concentrate in a hermetically sealed container such as an ampoule or sachette indicating the quantity of active agent. Where the composition is to be administered by Infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Administration to an individual of an effective amount of the compound can also be accomplished topically by administering the compound(s) directly to the affected area of the skin of the individual. For this purpose, the compound is administered or applied in a compositon including a pharmacologically acceptable topical carrier, such as a gel, an ointment, a lotion, or a cream, which includes, without limitation, such carriers as water, glycerol, alcohol, propylene glycol, fatty alcohols, triglycerides, fatty acid esters, or mineral oils.

Other topical carriers include liquid petroleum, isopropyl palmitate, polyethylene glycol, ethanol (95%), polyoxyethylene monolaurate (5%) in water, or sodium lauryl sulfate (5%) in water. Other materials such as anti-oxidants, humectants, viscosity stabilizers, and similar agents may be added as necessary. Percutaneous penetration enhancers such as Azone may also be included.

In addition, in certain instances, it is expected that the compound may be disposed within devices placed upon, in, or under the skin. Such devices include patches, implants, and injections which release the compound into the skin, by either passive or active release mechanisms.

Materials and methods for producing the various formulations are well known in the art and may be adapted for practicing the subject invention. See e.g. U.S. Pat. Nos. 5,182,293 and 4,837,311 (tablets, capsules and other oral formulations as well as intravenous formulations) and European Patent Application Publication Nos. 0 649 659 (published Apr. 26, 1995; illustrative formulation for IV administration) and 0 648 494 (published Apr. 19, 1995; illustrative formulation for oral administration).

The effective dose of the compound will typically be in the range of about 0.01 to about 50 mg/kgs, preferably about 0.1 to about 10 mg/kg of mammalian body weight, administered in single or multiple doses. Generally, the compound may be administered to patients in need of such treatment in a daily dose range of about 1 to about 2000 mg per patient.

The amount of compound which will be effective in the treatment or prevention of a particular disorder or condition will depend in part on the nature and severity of the disorder or condition, which can be determined by standard clinical techniques. In addition, in vitro or in vivo assays may optionally be employed to help identify optimal dosage ranges. Effective doses may be extrapolated from dose-response curves derived from in vitro or animal model test systems. The precise dosage level should be determined by the attending physician or other health care provider and will depend upon well known factors, including route of administration, and the age, body weight, sex and general health of the individual; the nature, severity and clinical stage of the disease; the use (or not) of concomitant therapies.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceutical products, which notice reflects approval by the agency of manufacture, use or sale for human administration.

The representative examples which follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art.

The following examples contain important additional information, exemplification and guidance which can be adapted to the practice of this invention in its various embodiments and the equivalents thereof.

EXAMPLES

Abbreviations. The following abbreviations are used in this document.

| | |
|---|---|
| Abu | alpha-aminobutyric acid |
| Ac | acetyl |
| aq | aqueous |
| Bn | benzyl |
| Boc | tertiary butyloxycarbonyl |
| BOC—ON | $(CH_3)_3COCO_2N=C(C_6H_5)CN$ |
| Cbz | benzyloxycarbonyl |
| CDI | 1,1'-carbonyldiimidazole |
| Chx | cyclohexyl |
| DCM | dichloromethane |
| DBU | 1,8-diazabicyclo[5.4.0]undec-7-ene |
| DIBAL-H | diisobutylaluminum hydride |
| DIEA | N,N-diisoopropylethylamine |
| DMAP | 4-dimethylaminopyridine |
| DME | ethylene glycol dimethyl ether |
| DMF | N,N-dimethylformamide |
| DMSO | dimethylsulfoxide or methyl sulfoxide |
| EDC.HCl | 1-(3-dimethylaminopropyl)-3-ethylcarbodiimide |
| Gln | glutamine |
| Glu | glutamic acid |
| Gly | glycine |
| HMDS | 1,1,1,3,3,3-hexamethyldisilazane |
| HOBT | 1-hydroxybenzotriazole |
| HPLC | high performance liquid chromatography |
| LiHMDS | lithium hexamethyldisilazide |
| MeCN | acetonitrile |
| MS | mass spectrometry |
| Ms | methanesulfonyl (mesyl) |
| NBS | N-bromosuccinimide |
| NMR | nuclear magnetic resonance |
| Pd/C | palladium on carbon |
| Rochelle salt | potassium sodium tartrate |
| satd | saturated |
| Su | succinimide |
| pyr | pyridine |
| rt or RT | room temperature |
| TBAF | tetrabutylammonium fluoride |
| TBS | tertiarybutyldimethylsilyl |
| TFA | trifluoroacetic acid |
| TFAA | trifluoroacetic anhydride |
| THF | tetrahydrofuran |
| TLC | thin layer chromatography |

| | |
|---|---|
| TMS | trimethysilyl |
| Tyr | tyrosine |

Example 1

[(4-{(S)-2-Acetylamino-2-[(S)-1-(3-carbamoyl-4-cyclohexylmethoxy-phenyl)-ethylcarbamoyl]-ethyl}-phenyl)-phosphono-methyl]-phosphonic Acid

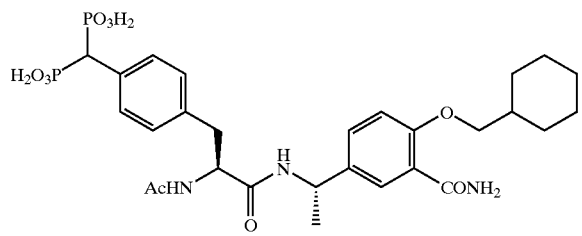

(a) p(CH$_2$PO$_3$Et$_2$)-L-Phe-OH

Fmoc-p(CH$_2$PO$_3$Et$_2$)-L-Phe-OH (5.0 g, 93 mmol) was dissolved in 170 mL of THF and 50 mL of diethyl amine and the mixture was vigorously stirred at rt for 3 h. Solvents were removed under reduced pressure and the solid was resuspended in anhydrous ether, filtered, and dried on high vacuum to afford 2.8 g (94%) of p(CH$_2$PO$_3$Et$_2$)-L-Phe-OH as white solid which was used without purification in the next step.

(b) N-Boc-p(CH$_2$PO$_3$Et$_2$)-L-Phe-OH

To a solution of p(CH$_2$PO$_3$Et$_2$)-L-Phe-OH (5.0 g, 16.7 mmol) in a 1:1 mixture of DME/water (140 ml) at 0° C. was added NaHCO$_3$ (3.1 g, 36.8 mmol) followed by Boc$_2$O (4.0 g, 18.4 mmol). The mixture was stirred at 0° C. for 30 min then warmed to rt and red for 1 hr. About 50 ml of DME was removed by evaporation then the remaining aqueous solution was extracted with EtOAc (2×50 mL). The aqueous layer was brought to pH 4 with 1 N HCl and extracted with EtOAc (3×100 mL). The combined extracts (second) were washed with water, dried over MgSO$_4$, filtered and concentrated to a colorless oil (62 g, 900%). MS [M−H]$^-$ 414.

(c) N-Boc-p(CH$_2$PO$_3$Et$_2$)-L-Phe-OMe,

To a solution of N-Boc-p(CH$_2$PO$_3$Et$_2$)-L-Phe-OH (5.1 g, 12.2 mmol) in DMF (60 mL) was added Cs$_2$CO$_3$ (4.8 g, 14.7 mmol) followed by MeI (0.76 ml, 12.2 mmol). The mixture was stirred for 1 hr, diluted with water (600 ml) and extracted with EtOAc (3×100 mL). The combined extracts were washed with water, 10% NaHSO$_3$, dried over MgSO$_4$, filtered and concentrated to a solid which was recrystallized from EtOAc/hexane to give a white solid (4.6 g, 88%). MS [M−H]$^-$ 428. m.p. 104–105° C.

(d) N-Boc-p[CH(PO$_3$Et$_2$)$_2$]-L-Phe-OMe

To a suspension of N-Boc-p(CH$_2$PO$_3$Et$_2$)-L-Phe-OMe (7.0 g, 16.3 mmol) in 185 mL of anhydrous DME, purged with N$_2$ and cooled to −42° C. (CH$_3$CN/dry ice), was added dropwise lithium bis(trimethylsilyl)amide (1 M THF, 48.9 mL, 48.9 mmol) and the reaction mixture was stirred at −42° C. for 15 min. Diethylchlorophosphate (4.7 mL, 32.6 mmol) was added and the orange solution was stirred at −42° C. for an additional 20 min before being quenched with 1 N HCl (20 ml). The mixture was further diluted with water and extracted with EtOAc (3×100 mL). The combined extracts were washed with water, dried over MgSO$_4$, filtered, concentrated, and chromatographed over silica gel (3% MeOH/CH$_2$Cl$_2$) to give a colorless oil (6.0 g, 65%). MS [M−H]$^-$564.

(e) N-Boc-p[CH(PO$_3$Et$_2$)$_2$]-L-Phe-OH

To a solution of N-Boc-p[CH(PO$_3$Et$_2$)$_2$]-L-Phe-OMe (0.490 g, 0.966 mmol) in 5 mL of THF cooled to 0° C. was added dropwise a solution of lithium hydroxide monohydrate (49.0 mg, 1.17 mmol) in 1.0 mL of water. The reaction mixture e was stirred at 0° C. for 1 h. THF was removed under reduced pressure to a yellow oil which was diluted with 10 mL of 1 N HCl. The aqueous phase was extracted with CH$_2$Cl$_2$ (8×15 mL), and the extracts were combined, dried over Na$_2$SO$_4$, and concentrated to afford 0.453 g (95%) of N-Boc-p[CH(PO$_3$Et$_2$)$_2$]-L-Phe-OH as a crystalline white solid. MS [M−H]$^-$ 550. m.p. 84–87° C.

(f) [(4-{(S)-2-tert-Butoxycarbonylamino-2-[(S)-1-(3-carbamoyl-4-cyclohexylmethoxy-phenyl)-ethylcarbamoyl]-ethyl}-phenyl)-(diethoxy-phosphoryl)-methyl]-phosphonic Acid Diethyl Ester To N-Boc-p[CH(PO$_3$Et$_2$)$_2$]-L-Phe-OH (2.0 g, 3.63 mmol) in CH$_2$Cl$_2$/DMF (5:1, 37 mL) at 0° C. was added HOBT (0.54 g, 3.98 mmol) and EDC (0.76 g, 3.98 mmol). The mixture was stirred for 10 min then (S)-5-(1-amino-ethyl)-2-cyclohexylmethoxybenzamide (WO 97/12903) (1.10 g, 398 mmol) was added and stirring was continued for 1 h. The solution was dumped into water and the layers separated. The aqueous layer was extracted with methylene chloride and the combined extracts were washed with water, 1 N HCl, sat'd NaHCO$_3$, dried over magnesium sulfate and concentrated to a glassy solid (2.8 g, 95%) which was homogeneous by HPLC. MS [M−H]$^-$ 808.

(g) [(4-{(S)-2-Amino-2-[(S)-1-(3-carbamoyl-4-cyclohexylmethoxy-phenyl)-ethylcarbamoyl]-ethyl}-phenyl)-(diethoxy-phosphoryl)-methyl]-phosphonic Acid Diethyl Ester To [(4-{(S)-2-tert-Butoxycarbonylamino-2-[(S)-1-(3-carbamoyl-4-cyclohexylmethoxy-phenyl)-ethylcarbamoyl]-ethyl}-phenyl)-(diethoxy-phosphoryl)-methyl]-phosphonic acid diethyl ester (2.8 g, 3.5 mmol) in methylene chloride (20 mL) was added TFA (6 mL). The mixture was stirred for 20 min., evaporated to dryness, and dissolved in DMSO (30 mL). Purification by RP HPLC (CH$_3$CN/H$_2$O) and lyophylization yielded a white solid (1.9 g, 2.3 mmol, 66%). MS [M+H]$^+$ 710.

(h) [(4-{(S)-2-Acetylamino-2-[(S)-1-(3-carbamoyl-4-cyclohexylmethoxy-phenyl)-ethylcarbamoyl]-ethyl}-phenyl)-(diethoxy-phosphoryl)-methyl]-phosphonic Acid Diethyl Ester To [(4-{(S)-2-amino-2-[(S)-1-(3-carbamoyl-4-cyclohexylmethoxy-phenyl)-ethylcarbamoyl]-ethyl}-phenyl)-(diethoxy-phosphoryl)-methyl]-phosphonic acid diethyl ester. TFA salt (1.9 g 23 mmol) in CH$_2$Cl$_2$ (50 mL) at 0° C. was added DIPEA (2.32 mL, 13.4 mmol) and Ac$_2$O (0.32 mL, 3.34 mmol). The mixture was stirred for 10 min., diluted with 1 N HCl and the layers seperated. The aqueous layer was extracted with methylene chloride and the combined extracts were washed with water, 1 N HCl, sat'd NaHCO$_3$, dried over magnesium sulfate, and concentrated to a glassy solid (1.7 g, 98%) which was homogeneous by HPLC. MS [M−H]$^-$ 750.

(i) [(4-{(S)-2-Acetylamino-2-[(S)-1-(3-carbamoyl-4-cyclohexylmethoxy-phenyl)-ethylcarbamoyl]-ethyl}-phenyl)-(diethoxy-phosphono)-methyl]-phosphonic Acid To [(4-{2-Acetylamino-2-[1-(3-carbamoyl-4-cyclohexylmethoxy-phenyl)-ethylcarbamoyl]-ethyl}-phenyl)-phosphoryl-methyl]-phosphonic acid diethyl ester (1.83 g, 2.43 mmol) in CH$_3$CN (30 mL) at −10° C. was added TMSI (6.92 mL, 48.7 mmol). The mixture was stirred for 10 min., quenched with sat'd NaHCO$_3$ and decolorized with the dropwise addition of 10% sodium hydrogen sulfite.

The CH₃CN was removed on a rotary evaporator and the remaining aqueous solution diluted with DMF (10 mL). Purification by RP HPLC (CH₃CN/H₂O) and lyophylization on yielded a white solid (15 g, 66%). MS [M+H]⁻ 639.

Example 2

[(4-{(S)-2-Acetylamino-2-[(S)-1-(4-cyclohexylmethoxy-phenyl)-ethylcarbamoyl]-ethyl}-phenyl)-phosphono-methyl]-phosphonic Acid

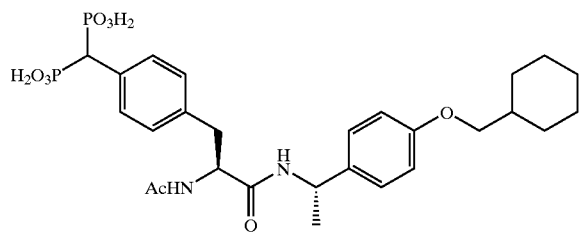

(a) 1-(4-(Cyclohexylmethoxy)phenyl)ethanone

To a solution of 4'-hydroxyacetophenone (10.6 g, 77.7 mmol) in 600 mL MeOH and 15 mL H₂O at room temperature was added Cs₂CO₃ (25.6 g, 1.01 eq). The reaction mixture immediately turned yellow and was then stirred for 40 min. The MEOH was removed in vacuo, and the remaining H₂O was removed azetropically with 5×100 mL toluene. The resulting yellow solid was suspended in DMF (450 mL) and treated with (bromomethyl)cyclohexane (13.0 mL, 1.2 eq). The reaction mixture was heated to 90° C. and stirred overnight. The reaction mixture was then cooled to room temperature, poured into 500 mL of ice water and extracted with Et₂O. The Et₂O extract was dried over MgSO₄ and concentrated in vacuo to a yellow oil, which smelled of the starting bromide. The bromide was distilled off at 50° C. under high vacuum until the bottoms reached a constant weight (13.96 g, 77%). This oil solidified to a white solid upon standing. ¹H NMR (300 MHz CDCl₃): 7.91 (2H, d, J=8.9 Hz), 6.90 (2H, d, J=8.8 Hz), 3.81 (2H, d, J=6.1 Hz), 2.55 (3H, s), 1.8 (6H, m), 1.2 (3H, m), 1.1 (2H, m).

(b) (R)-1-(4-(Cyclohexylmethoxy)phenyl)-1-ethanol

A solution of 1-(4-(Cyclohexylmethoxy)phenyl)ethanone (1.05 g, 4.5 mmol) in THF (2.5 mL) was added dropwise to a solution of (+)-DIP-Cl 2.3 g 1.59 eq) in THF (7.2 mL) at −55° C. under N₂. The reaction mixture was allowed to slowly warm to −14° C. After 18 h, the reaction mixture was warmed to room temperature and concentrated in vacuo. The resulting oil was then diluted with Et₂O (50 mL) and treated with diethanolamine (1.5 mL). This mixture was stirred for 3 h and then filtered through Celite to remove the white precipitate. The filtrate was removed in vacuo to give a yellowish oil. Flash chromatography on silica gel eluting with 20:1 to 85:15 hexanes-EtOAc afforded 790 mg of material contaminated with reagent by-products as impurities.

(c) (S)-1-(4-(Cyclohexylmethoxy)phenyl)-1-azidoethane

To a solution of (R)-1-(4-(Cyclohexylmethoxy)phenyl)-1-ethanol (790 mg, 3.3 mmol) in toluene (5.7 mL) at 0° C. was added (PhO)₂PON₃ (0.87 mL, 1.2 eq) followed by DBU (0.61 mL, 1.2 eq) (dropwise). The reaction was allowed to slowly warm to room temperature overnight. The reaction mixture was washed with H₂O and 5% aq HCl. The organic layer was dried over MgSO₄ and concentrated in vacuo. Flash chromatography on silica gel eluting with 100:1 to 20:1 hexanes-EtOAc gave 700 mg of pure azid. ¹H NMR (300 MHz, CDCl₃): 7.22 (2H, d J=98.6 Hz), 6.88 (2H, d, J=8.6 Hz), 4.55 (1H, q, J=6.8 Hz), 3.75 (2H, d, J=6.2 Hz), 1.8 (6H,), 1.51 (3H, d, J=6.8), 1.25 (3H, m), 1.05 (2H, m).

(d) (S)-(4-(Cyclohexylmethoxy)phenyl)-1-ethylamine, Hydrochloride Salt

A solution of (S)-1-(4-(Cyclohexylmethoxy)phenyl)-1-azidoethane (700 mg, 2.69 mmol) in EtOH (50 mL) containing 10% Pd/C (143 mg, 0.05 eq) was stirred under an atmosphere of H₂ (balloon) for 2.5 h. The catalyst was then removed by filtration, and the filtrate was concentrated in vacuo. The material was diluted with 50 mL of Et₂O and acidified with 50 mL ethereal HCl (prepared from 50 mL Et₂O, 0.27 mL MeOH and 0.29 mL AcCl). The resulting HCl salt precipitated and was collected by filtration. NMR of free base (300 MHz, CDCl₃): 7.25 (2H, d, J=6.8 Hz), 6.85 (2H, d, J=6.7 Hz), 4.05 (1H, q, J=6.6 Hz), 3.73 (2H, d, J=6.3 Hz), 1.75 (6H m), 1.35 (3H, d, J=6.6 Hz), 1.22 (3H, m), 1.05 (2H, m).

(e) [(4-{(S)-2-Acetylamino-2-[(S)-1-(4-cyclohexylmethoxy-phenyl)-ethylcarbamoyl]-ethyl}-phenyl)-phosphono-methyl]-phosphonic Acid The title compound was synthesized in a manner similar to that described for Example 1. The product was obtained as a colorless powder. Electrospray Mass Spectrum (50/50 acetonitrile/water +0.1% ammonium hydroxide) m/z 595.2 (M−H).

Example 3

({4-[(S)-2-Acetylamino-2-(4-cyclohexylmethoxy-benzylcarbamoyl)-ethyl]-phenyl}-phosphono-methyl)-phosphonic Acid

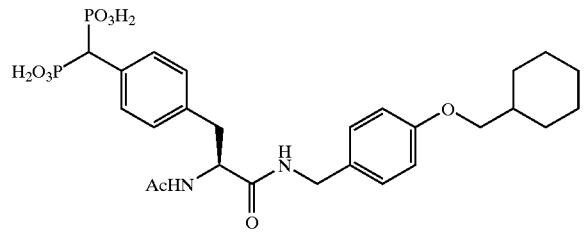

(a) 4-(Cyclohexylmethoxy)benzaldehyde

A mixture of 4-hydroxybenzaldehyde (1.22 g, 10.0 mmol), K₂CO₃ (1.45 g, 10.5 mmol), and bromomethylcyclohexane (1.54 mL, 11.0 mmol) in CH₃CN (20 mL) was stirred at reflux for three days. The reaction mixture was then cooled, poured into 1 M aq NaOH and extracted with Et₂O. The extract was washed with H₂O and brine. The aqueous washes were reextracted once with Et₂O, and the combined extracts were dried over MgSO₄ and concentrated to 2.03 g (93%) of ether as a solid. This material was used without further purification.

(b) 4-Cyclohexylmethoxy)benzoxime

To a solution of 4-Cyclohexylmethoxy)benzaldehyde (1.97 g, 9.02 mmol) in pyridine (10 mL) at rt under N₂ was added hydroxylamine hydrochloride (0.69 g, 9.93 mmol). The yellow solution was stirred at rt for 2 h and then concentrated under a stream of nitrogen. The residue was taken up in CHCl₃ and loaded onto a silica gel column. Elution with 5:1 hexanes-ethyl acetate followed by 3:1 hexanes-ethyl acetate afforded 2.07 g (98%) of oxime as a mixture of geometric isomers.

(c) 4-(Cyclohexylmethoxy)benzylamine Hydrochloride

A solution of 4-(Cyclohexylmethoxy)benzoximine (2.06 g, 8.83 mmol) in EtOH (80 mL)-conc. HCl (0.75 mL) containing 10% Pd/C (0.235 g, 0.22 mmol) was stirred under an atmosphere of H₂ (double stuffed balloon) for 5 h. The mixture was then filtered through a pad of Celite using excess EtOH. The solution was concentrated under a stream of $N_2$ overnight The resulting solid was transferred to a filter and washed with $Et_2O$. The solid was dried to 2.14 g (95%) of amine·HCl. Electrospray Mass Spectrum (50/50 acetonitrile/water +0.1% ammonium hydroxide) m/z 203.3 (M+H–$NH_3$).

(d) ({4-[(S)-2-Acetylamino-2-(4-cyclohexylmethoxy-benzylcarbamoyl)-ethyl]-phenyl}-phosphono-methyl)-phosphonic Acid The title compound was synthesized in a manner similar to that described for Example 1. The product was obtained as a colorless powder. Electrospray Mass Spectrum (50/50 acetonitrile/water +0.1% ammonium hydroxide) m/z 581.0 (M–H).

Example 4

[(4-{(S)-2-[1-(3-Carbamoyl-4-isobutoxy-phenyl)-1-methyl-ethylcarbamoyl]-2-(2,2-dimethylpropionylamino)-ethyl}-phenyl)phosphono-methyl]-phosponic Acid

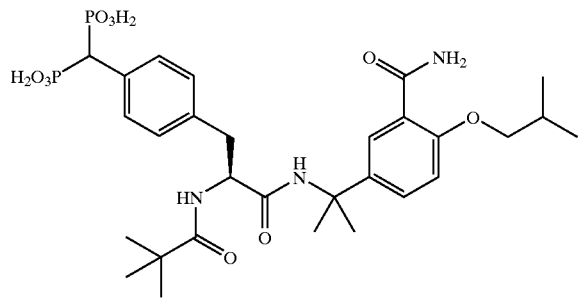

(a) 5-Acetyl-2-(2-(2-methylpropyloxy)benzamide

To a mixture of 5-acetylsalicylamide (8.96 g, 50.0 mmol) in 400 mL of MeOH containing 10 mL of $H_2O$ was added $Cs_2CO_3$ (16.45 g, 50.5 mmol) at rt. The mixture was stirred at rt for 44 min. The resulting yellow solution was then concentrated in vacuo. Toluene (~200 mL) was added to the residue and then removed in vacuo to azeotropically remove the $H_2O$. This was repeated twice more. The resulting yellow powder was suspended in DMF (~200–300 mL) and treated with isobutyl bromide (82 mL, ~75.0 mmol). The reaction mixture was stirred at 90° C. for 20 h and then cooled to rt Water (~500 mL) was then added with vigorous stirring. The mixture was then cooled to 0° C. with continued stirring. The mixture was then filtered, and the solid was washed with $H_2O$ and $Et_2O$. Drying under high vacuum over $P_2O_5$ afforded 10.44 g (89%) of ether.

(b) 5-(1-Hydroxy-1-methylethyl)-2-(2-methylpropyloxy)benzamide

To a suspension of 5-Acetyl-2-(2-methylpropyloxy) benzamide (10.44 g, 44.4 mmol) in THF (100 mL) at 0° C. under $N_2$ was added MeMgBr (90 mL, 3.0 M in $Et_2O$). The resulting thick slurry could no longer be stirred with the magnetic stirrer, so the flask was swirled by hand a few times. An additional 20 mL of THF was added to allow the reaction mixture to be stirred with the magnetic stirrer. After 1 h, the reaction was still incomplete, so an additional 15 mL of MeMgBr and 10 mL of THF was added. The reaction mixture was stirred at 0° C. for an additional 1 h and then quenched by the slow, careful addition of 1 M aqueous $H_2SO_4$ at 0° C. The mixture was diluted with additional 1 M $H_2SO_4$ and then extracted with EtOAc. The extract was then washed with $H_2O$ and brine. The aqueous washes were reextracted once with EtOAc, and the combined extracts were dried over $MgSO_4$ and concentrated. The crude material was purified by flash chromatography on silica gel. Elution with 20:1 $CHCl_3$-MeOH did not produce good separation. All fractions containing product were collected and concentrated. The residued was resubjected to flash chromatography on silica gel. Elution with 1:1 EtOAc-hexanes followed by 2:1 EtOAc-hexanes afforded 5.11 g (46%) of alcohol.

(c) 5-(1-Azido-1-methylethyl)-2-(2-methylpropyloxy) benzamide

To a mixture of $NaN_3$ (3.96 g, 60.9 mmol) in a solution of 5-(1-Hydroxy-1-methylethyl)-2-(2-methylpropyloxy) benzamide (5.1 g, 20.3 mmol) in $CHCl_3$ (160 mL) at 0° C. under $N_2$ was slowly added TFA (7.8 mL, 101 mmol). The reaction mixture was stirred overnight while slowly warming to rt. The thick slurry was then poured into $H_2O$ (100 mL). The layers were separated, and the organic layer was washed with additional $H_2O$ (100 mL) and brine (100 mL). The aqueous washes were reextracted with EtOAc, and the combined extracts were dried over $MgSO_4$ and concentrated. The material was purified by flash chromatography on silica gel. Elution with 2:1 hexanes-EtOAc produced product that was still contaminated with TFA. The product was dissolved in EtOAc and washed with half-saturated aqueous $NaHCO_3$ (100 mL) and saturated aqueous $NaHCO_3$ (100 mL). The aqueous washes were reextracted once with EtOAc, and the combined extracts were dried over $MgSO_4$ and concentrated to 5.23 g (93%) of azide as a white solid which was used without further purification.

(d) 5-(1-Amino-1-methylethyl)-2-(2-methylpropyloxy) benzamide

A solution of the azide (5.23 g, 18.9 mmol) in EtOH (170 mL) containing 10% Pd/C (0.5 g, 0.473 mmol) was stirred at rt under an atmosphere of $H_2$ (double stuffed balloon) for 3 h. At this point, additional 10% Pd/C was added and the balloon was changed. After an additional 2 h, the reaction mixture was filtered through a pad of Celite using excess EtOAc. The filtrate was then concentrated. The residue was dissolved in 1.0 M aqueous HCl (100 mL) and $H_2O$ (150 mL) and washed twice with EtOAc. The aqueous layer was then basified by the addition of 6.0 M aqueous NaOH and extracted twice with $CH_2Cl_2$. The combined extracts were dried over $K_2CO_3$ and concentrated in vacuo affording 4.30 (91%) of amino as a white solid. Electrospray Mass Spectrum (50/50 acetonitrile/water +0.1% ammonium hydroxide) m/z 249.4 (M–H).

(e) [(4-{(S)-2-[1-(3-Carbamoyl-4-isobutoxy-phenyl)-1-methyl-ethylcarbamoyl]-2-(2,2-dimethylpropionylamino)-ethyl}-phenyl)-phosphono-methyl]-phosphonic Acid The title compound was synthesized in a manner similar to that described for Example 1. The product was obtained as a colorless powder. Electrospray Mass Spectrum (50/50 acetonitrile/water +0.1% ammonium hydroxide) m/z 654.1 (M–H).

Example 5

(e) ({4-[(S)-2-[(S)-1-(3-Carbamoyl-4-isopropoxy-phenyl)-ethylcarbamoyl]-2-(2,2-dimethylpropionylamino)-ethyl]-phenyl}-phosphono-methyl)-phosphonic Acid

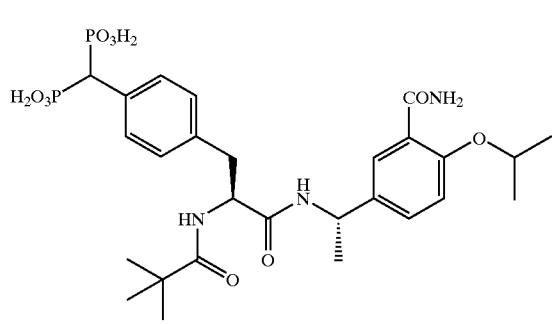

The title compound was synthesized in a manner similar to that described for Example 1. The product was obtained as a white solid MS [M–H]⁻ 626.

Example 6

[(4-{(S)-2-[(S)-1-(3-Carbamoyl-4-isobutoxy-phenyl)-ethylcarbamoyl]-2-phenylacetylaminoethyl}-phenyl)-phosphono-methyl]-phosphonic Acid

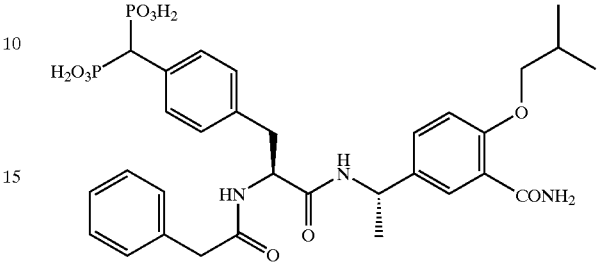

The title compound was synthesized in a manner similar to that described for Example 1. The product was obtained as a white solid. MS [M–H]⁻ 674.

The compounds of Examples 5 and 6 have also been prepared using solid phase chemistry by the method illustrated in the following scheme:

Solid Phase Synthesis

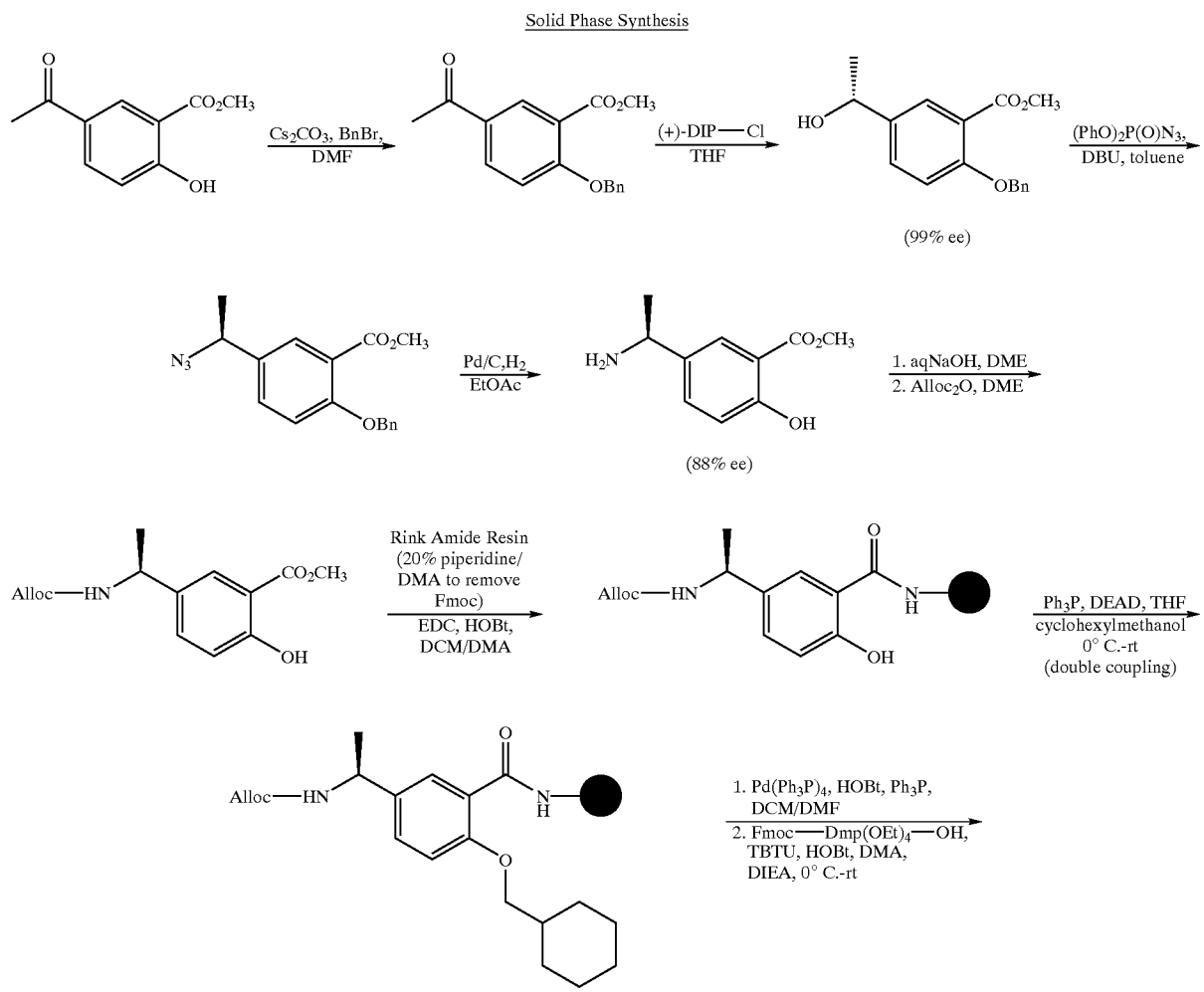

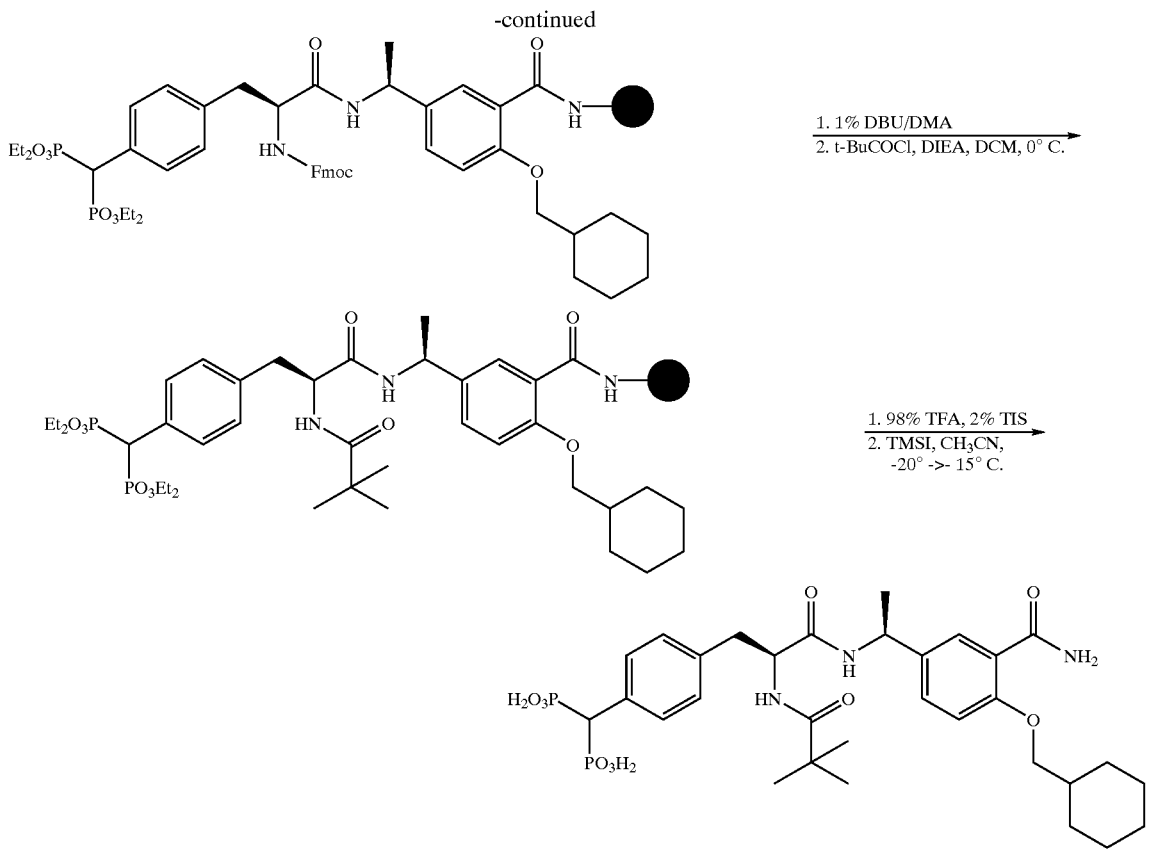

Example 7

4-{(S)-2-Acylamino-2-(S)-1-(3-carbamoyl-4-cyclohexylmethoxy-phenyl]ethylcarbamoyl-ethylphenyl-phosphonoacetic Acid

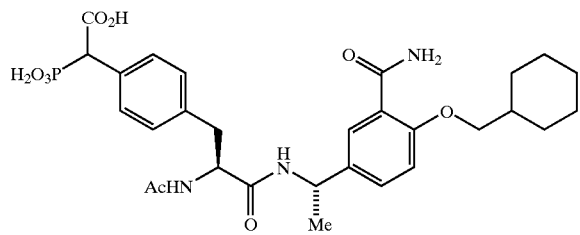

(a) Dietoxy-phosphoryl)-(4-iodophenyl)acetic Acid t-Butyl Ester

To diethoxyphosphoryl acetic acid t-butyl ester (5.04 g, 20 mmol) in DMF (25 mL) was added sodium hydride (0.84 g, 60 mmol) in small portions under nitrogen. After 30 min. a solution of 1,4-diiodobenzene (3.3 g, 10 mmol) and copper (I) iodide (3.8 g, 10 mmol) in DMF (10 mL) was added and nitrogen was bubbled through this solution for 10 min. to make sure that there was no air in the system and the tube was sealed and heated to 100° C. for 6 h. The reaction mixture after cooling was poured into 10% hydrochloric acid (200 mL). The solution was filtered on celite and the celite was repeatedly washed with ethyl acetate (3×50 mL). Ethyl acetate was separated and the aquoes solution was extracted repeatedly with ethyl acetate (2×25 mL). Combined ethyl acetate was washed with water (10 mL), dried ($Na_2SO_4$) and concentrated to give a yellow gum which was purified by column chromatography on silica gel using hexane/acetone (7/3) to give a pale yellow gum which solidified in the freezer, m.p 68° C. (3.28 g, 72%).

(b) 4-{(t-Butoxycarbonyl-diethoxyphophonyl)-methyl-N-(t-butoxycarbonyl-S-phenyl Alanine Bezyl Ester Zinc (0.1438 g, 2.2 mmol) was covered with THF/DMA (2 mL) and heated to 60° C. dibomoethane (22 μL) was added and the flask was removed from the oil bath. TMS chloride (30 μL) was added and the mix was sonicated at rt for 15 min. after which it was again heated to 60° C. on an oil bath. N-t-butoxycarbonyl-2-iodo-L-alanine benzyl ester (0.8105 g, 2 mmol) in THF/DMA (4 mL, 1/1) was added to the activated zinc at 60° C. and the reaction mixture was again sonicated for 30 min after which it was heated to 60° C. After 1 h, a mixture of diethoxyphosphoryl)-(4-iodophenyl)acetic acid t-butyl ester (0.4542 g, 1 mmol), bis(benzonitrile)palladium(II)chloride (21.86 mg, 0.057 mmol), tri-o-tolylphosphine (33.17 mg, 0.109 mmol) in THP/DMA (8 mL, 1/1) was added and the reaction mixture was diluted with excess of ethyl acetate (~200 mL) and 1N Hcl (20 mL) and it was filtered through celite. Organic layer was separated, washed (water, 10 mL), dried ($Na_2SO_4$) and concentrated in vacuo. The resulting gum was purified by flash chromatography on silica gel using hexane ethyl acetate (85/15) to give the recovered starting material 120 mg, 22%), and the product, 424 mg (70%)., m.p. 89° C.

(c) 4-{(t-Butoxycarbonyl-diethoxyphophonyl)-methyl-N-(t-butoxycarbonyl-S-phenyl Alanine To 4-{(t-butoxycarbonyl-diethoxyphophonyl)-methyl-N-(t-butoxycarbonyl-S-phenyl alanine propionic acid bezyl ester (420 mg, 0.695 mmol) was added ethyl acetate (45 mL) followed by 10% Pd/C (75 mg) carefully in an inert atmosphere. The flask was fitted with a balloon containing hydrogen and stirred at rt for 5 h. The catalyst was filtered over a pad of celite and was repeatedly washed with ethyl acetate (3×10 mL). Combined ethyl acetate were concentrated to give 348.2 mg (97%), m.p. 138° C.

(d) 4-{(S)-2-Acylamino-2-(S)-1-(3-carbomoyl-4-cyclohexylmethoxy-phenyl)ethylcarbonyl-ethyl}phenyl-phosphonoacetic Acid The title compound was synthesized in a manner similar to that described for Example 1. The product was obtained as a colorless powder. Electrospray Mass Spectrum (50/50 acetonitrile/water +0.1% ammonium hydroxide) m/z 602 (M−H).

Example 8

[(4-{2-[(S)-1-(3-Carbamoyl-4-cyclohexylmethoxy-phenyl)-ethylcarbamoyl]-ethyl}-phenyl)-sulfamoyl-methyl]-phosphonic Acid

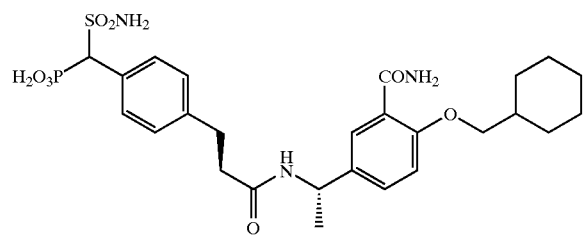

The title compound was synthesized in a manner similar to that described for Example 1. The product was obtained as a white solid. MS [M+H]$^+$ 581.

Example 9

(5-{(S)-2-Acetylamino-2-[(S)-1-(3-carbamoyl-4-cyclohexylmethoxy-phenyl)-ethylcarbamoyl]-ethyl}-2-phosphonooxy-phenyl)-phosphonic Acid

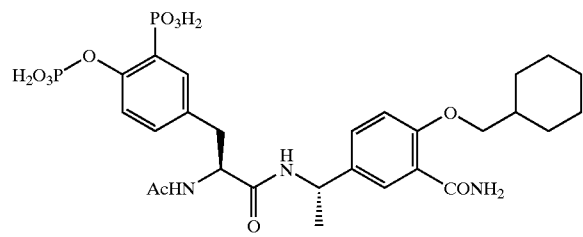

(a) 2-Acetylamino-3-(3-bromo-4-hydroxy-phenyl)-propionic Acid Methyl Ester

To N-acetyl-L-tyrosine methyl ester (6 g, 25.3 mmol) in THF (60 mL) at rt was added NBS (5.4 g, 30.3 mmol) followed by five drops of sulfuric acid. The mixture was stirred for 16 h at rt The solvent was removed under reduced pressure and then water was added. The aqueous layer was extracted twice with EtOAc, and the combined extracts were dried over magnesium sulfate and concentrated to a solid. The solid was recrystallized from ethyl acetate/hexane (6 g, 75%). MS (M+H)$^+$ 316.

(b) 2-Acetylamino-3-[3-(diethoxy-phosphoryl)-4-hydroxy-phenyl]-propionic Acid Methyl Ester To 2-Acetylamino-3-(3-bromo-4-hydroxy-phenyl)-propionic acid methyl ester (3 g, 9 mmol), diethyl phosphite (1.6 ml, 11 mmol) and 4-methylmorpholine (1.5 mL, 13.5 mmol) in toluene (10 mL) and MeCN (10 mL) was added Pd(Ph$_3$)$_4$ (0.5 g, 0.45 mmol). The mixture was allowed to stir for two days at 100° C. It was then diluted with saturated NH$_4$Cl and extracted with EtOAc. The organic layer was dried over magnesium sulfate, concentrated, and chromatographed over silica gel (5% MeOH/CHCl$_3$) to an oil. MS [M+H]$^+$ 374 and [M−H]$^−$ 372.

(c) 2-Acetylamino-3-[3-diethoxy-phosphoryl)-4-(diethoxy-phosphoryloxy)-phenyl]-propionic Acid Methyl Ester To 2-Acetylamino-3-[3-(diethoxy-phosphoryl)-4-hydroxy-phenyl]-propionic acid methyl ester (0.15 g, 0.25 mmol) in MeCN (10 mL) was added diethyl chlorophosphate (0.05 mL, 0.3 mmol) followed by K$_2$CO$_3$ (0.07 g, 0.5 mmol) at rt. The reaction was stirred for 4 h before H$_2$O (10 mL) and EtOAc (20 mL) were added. The organic layer was dried over magnesium sulfate, concentrated, and chromatographed over silica gel (20% MeOH/CHCl$_3$) to an oil. MS [M+H]$^+$ 510.

(d) (5-{(S)-2-Acetylamino-2-[(S)-1-(3-carbamoyl-4-cyclohexylmethoxy-phenyl)-ethylcarbamoyl]-ethyl}-2-phosphonooxy-phenyl)-phosphonic Acid The title compound was synthesized in a manner similar to that described for Example 1, steps e and f, followed by the TMSI promoted deprotection reaction. To a solution of 2-(diethylphosphonyl)-4-{(S)-2-acetylamino-2-[(S)-1-(3-carbamoyl-4-cyclohexylmethoxy-phenyl)ethylcarbamoyl]ethyl}-diethyl-phosphonate (80 mg, 0.12 mmol) in MeCN (3 mL) at −11° C. was added TMSI (0.3 mL, 2.3 mmol). The mixture was stirred for 3 h at −11° C. and then quenched with saturated NaHCO$_3$ (1 mL). The resulting mixture was purified by RP HPLC (CH$_3$CN/H$_2$O). Lyophilization left a white solid. MS [M+H]$^+$ 642.

Example 10

4-[(S)-2-Acetylamino-3-(3-phosphono-4-phosphonooxy-phenyl)propionylamino]-4-[(3-cyclohexyl-propyl)-methyl-carbomoyl]-butyric Acid

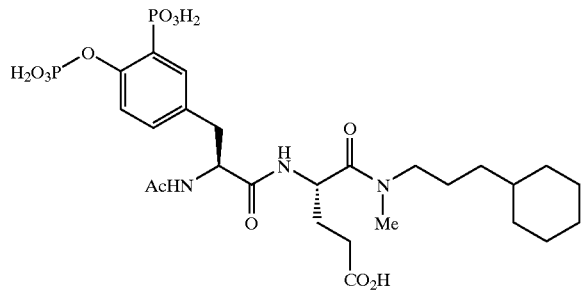

This compound was prepared following the procedure of example 8 except that L-Glu(OtBu)-N(methyl)(3-cyclohexylpropyl) (WO 97/12903) was used in the coupling procedure. MS [M−H]$^−$ 648.

Example 11

(4-{(S)-2-Acetylamino-2-[(S)-1-(3-carbamoyl-4-cyclohexylmethoxy-phenyl)ethylcarbamoyl]-ethyl}-2-phosphono-phenyl)-phosphonic Acid

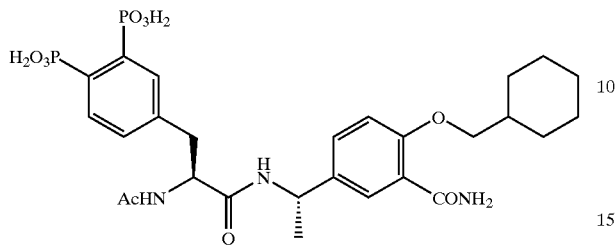

(a) 2-tert-Butoxycarbonylamino-3-(3,4-dihydroxy-phenyl)-propionic Acid Methyl Ester To (3,4-Dihydroxyphenyl)-L-alanine methyl ester hydrochloride (5.4 g, 25.4 mmol) and Di-tert-butyl dicarbonate (5.5 g, 25.4 mmol) in a mixture of THF (20 mL) and water (20 mL) at rt was added sodium bicarbonate (32 g, 38.1 mmol). The mixture was allowed to stirred for 16 h then washed with water, extracted with EtoAc. The organic layer was dried over magnessium sulfate, concentrated to a solid. The solid was recrystallized frome ethyl acetate/hexane (7 g, 88%). MS [M+H]$^+$ 312. m.p. 132–135° C.

(b) 3-(3,4-bis-Trifluoromethanesulfonyloxy-phenyl)-2-tert-butoxycabonylamino-propionic Acid Methyl Ester To 2-tert-Butoxycarbonylamino-3-(3,4-dihydroxy-phenyl)-propionic acid methyl ester (12 g, 38.6 mmol) and triethyl amine (13 mL, 88.7 mmol) in methylene chloride (100 mL) at 0° C. was added N-phenyl-bis (trifluoromethanesulfonimide) (31.6 g, 88.7 mmol). The mixture was allowed to stirred for two days then washed sequentially with 1 N NaOH, 1 N HCl, and brine. The organic layer was dried over magnessium sulfate, concentrated to a solid. The solid was recrystallized frome Dichloremethane/hexane. MS [M+N]$^+$ 598. m.p. 80–82° C.

(c) 3-[3,4-bis-(Diethoxy-phosphoryl)-phenyl]-2-tert-butoxycarbonylamino-propionic Acid Methyl Ester To 3-(3,4-Bis-trifluoromethanesulfonyloxy-phenyl)-2-tert-butoxycarbonylamino-propionic acid methyl ester (2 g, 3.47 mmol), diethyl phosphite (1 mL, 7.65 mmol) and 4-methyl morpholine (0.93 mL, 8.3 mmol) in MeCN (10 ml) was added Pd(Ph$_3$)$_4$ (167 mg, 0.15 mmol). The mixture was allowed to stirred for two days at 95° C. then diluted with saturated NH$_4$Cl and extracted with EtOAc. The organic layer was dried over magnessium sulfate, concentrated, and chromatographed over silica gel (5% MeOH/EtOAc) to an oil (0.2 g 37% yield). MS [M+H]$^+$ 552 and [M+Na] 574.

(d) 3-[3,4-bis-(Diethoxy-phosphoryl)-phenyl]-2-tert-butoxycarbonylamino-propionic Acid To a solution of 3-[3,4-Bis-(diethoxy-phosphoryl)-phenyl]-2-tert-butoxycarbonylamino-propionic acid methyl ester (110 mg, 0.2 mmol) in 5 mL of THF cooled to 0° C. was added dropwise a solution of lithium hydroxide monohydrate (8.5 mg, 0.2 mmol) in 1.0 mL of water. The reaction mixture was stirred at 0° C. for 1 h. THF was removed under reduced pressure to a yellow oil which was diluted with 10 mL of 1 N HCl. The aqueous phase was extracted with CH$_2$Cl$_2$ (2×15 mL), and the extracts were combined, dried over Na$_2$SO$_4$, and concentrated to afford an oil 107 mg (100%). MS [M−H]$^-$ 537.

(e) (4-{(S)-2-Acetylamino-2-[(S)-1-(3-carbamoyl-4-cyclohexylmethoxy-phenyl)-ethylcarbamoyl]-ethyl}-2-phosphono-phenyl)phosphonic Acid The title compound was synthesized in a manner similar to that described for Example 1. The product was obtained as a colorless powder (20 mg). MS [M+H]$^+$ 626.

Example 12

Phosphoric Acid Mono-(4-{(S)-2-acetylamino-2-[(S)-1-(3-carbamoyl-4-cyclohexylmethoxy-phenyl)-ethylcarbamoyl]-ethyl}-2-phosphonooxy-phenyl) ester

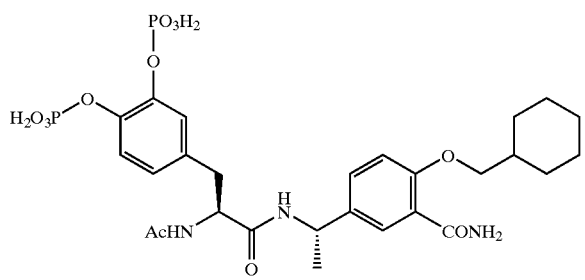

(a) 2-tert-Butoxycarbonylamino-(S)-3-(3,4-dihydroxy-phenyl)propionic Acid Methyl Ester To [3-(3,4-(Dihydroxyphenyl)-L-alanine] methyl ester (5.4 g, 25.4 mmol) and Di-tert-butyl dicarbonate (5.5 g, 25.4 mmol) in a mixture of THF (20 mL) and water (20 mL) at rt was added sodium bicarbonate (3.2 g, 38.1 mmol). The mixture was allowed to stirred for 16 h then washed with water. extracted with EtOAc. The organic layer was dried over magnessium sulfate, concentrated to a solid. The solid was recrystallized frome ethyl acetate/hexane (7 g, 88%). Ms [M+H]$^+$ 312.

(b) 3-(S)[3,4-bis-(Diethoxy-phosphoryloxy)-phenyl]-2-tert-butoxycarbonylamino-propionic Acid Methyl Ester To 2-tert-Butoxycarbonylamino-(S)-3-(3,4-dihydroxy-phenyl)-propionic acid methyl ester (2 g, 6.4 mmol) in MeCN (30 mL) was added diethyl chlorophosphate (1.1 mL, 7.7 mmol) followed by K$_2$CO$_3$ (3.5 g, 25.6 mmol) at rt The reaction was stilted for 8 h before H$_2$O (50 mL) and EtOAc (50 mL) were added. The organic layer was dried over magnesium sulfate, concentrated, and chromatographed over silica gel (5% MeOH/CHCl$_3$) to an oil (23 g, 62%). MS [M+H]$^+$ 584.

(c) Phosphoric Acid Mono-4-{(S)-2-acetylamino-2-[(S)-1-(3-carbamoyl-4-cyclohexylmethoxy-phenyl)-ethylcarbamoyl]-ethyl}-2-phosphonooxy-phenyl)ester The title compound was synthesized in a manner similar to that described for Example 1. The product was obtained as a colorless powder. Electrospray Mass Spectrum (50/50 acetonitrile/water +0.1% ammonium hydroxide) MS [M+H]$^+$ 673.

Example 13

(5-{2-[1-(3-Carbamoyl-4-cyclohexylmethoxy-phenyl)ethylcarbamoyl]ethyl}-2Phosphonomethoxy-phenyl)-phosphonic Acid

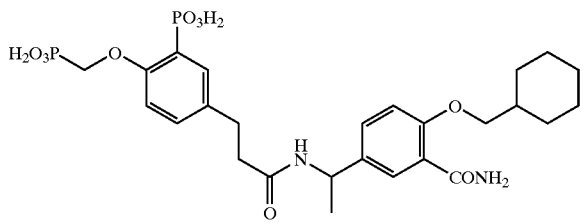

(a) 3-(4-Diethylphospnonooxyphenyl)propionic Acid Methyl Ester

To methyl 3-(4-hydroxyphenyl)propionate (11 g, 61 mmol) in dry ether (250 mL) at 0° C., was added NaH (1.8 g, 75 mmol) portionwise. The reaction mixture was stirred at room temperature for 1 hr and diethyl chlorophosphate (10.6 mL, 73 mmol) was added. Stirring was continued for another 2 hrs. The reaction was quenched by slow addition of water. Organic layer was separated and aqeous layer was extracted with ether twice. Combined organic layer was washed with 4N NaOH, brine and dried over $MgSO_4$. Afte removal of the solvent, the crude product was obtained as a colorless oil (19.0 g, 98%).

(b) 3-(3-Diethylphosphono-4-hydroxphenyl)propionic Acid Methyl Ester

Diisopropylamine (7.2 mL, 52.1 mmol) in dry THF (200 mL) at −78° C. was added BuLi (32.8 mL, 1.6 M in hexanes, 52.5 mmol) via syringe. The reaction was stirred at −78° C. for 30 min. 3-(4-Diethylphosphonophenyl)propionic acid methyl ester (4.66 g, 14.7 mmol) in dry THF (250 mL) was added by cannulation. Stirring was continued at −78° C. for 1 hr. The reaction was allowed to warm to room temperature, quenched with staurated $NH_4Cl$ (50 mL). The mixture was extracted with ether 3 times, and combined organic layer was dried $MgSO_4$ and concentrated. The residue was purified by flash column chromatography on silica gel (50% EtOAc/hexane, Rf=0.43) to give product as a clear oil (2.3 g, yield 50%).

(c) 3-(3-Diethylphosphono-4-diisopropylphosphonomethoxyphenyl)propionic Acid Methyl Ester 3-(3-Diethylphosphono-4-hydroxphenyl)propionic acid methyl ester (3.16 mg, 1 mmol) was dissolved in 4 mL of DMF and $Cs_2CO_3$ (429 mg, 1.32 mmol) was added, followed by diisopropyl bromomethylphosphonate (337 mg, 1.32 mmol). The reaction was stirred at 75° C. under $N_2$ overnight. The reaction was partitioned between EtOAc and $H_2O$, organic layer was separated, dried over $Na_2SO_4$ and concentrated. The residue was further purified by flash column chromatography on silica gel (10% MeOH/EtOAc, Rf=0.45) to obtain the pure product as a clear oil 474 mg (yield 96%).

(d) 3-(3-Diethylphosphono-4-diisopropylphosphonomethoxyphenyl)propionic Acid 3-(3-Diethylphosphono-4-diisopropylphosphonomethoxyphenyl)propionic acid methyl ester (474 mg, 0.96 mmol) in 5 mL THF at 0° C. was added $LiOH.H_2O$ (60 mg, 1.43 mmol) in 1 mL $H_2O$. The reaction mixture was stirred at 0° C. for 1 hr. THF was removed in vacuo and 5 mL 1N HCl was added. Aqueous phase was extracted with DCM (8×10 mL). Combined organic was dried over $Na_2SO_4$, concentrated to yield crude product 400 mg (yield 87%) as a clear oil. Electrospray mass spectrum: m/z 479.50 (M−H).

(e) (5-{2-[1-(3-Carbamoyl-4-cyclohexylmethoxy-phenyl)ethylcarbamoyl]ethyl}-2-diisopropylphosphonomethoxy-phenyl)phosphonic Acid Diethyl Ester HOBt (94 mg, 0.69 mmol) and EDC.HCl (140 mg, 0.73 mmol) were dissolved in 2.5 mL of dry DCM at 0° C. 3-(3-Diethylphosphono-4-diisopropylphosphonomethoxyphenyl)propionic acid (200 mg, 0.42 mmol) in 1.2 mL of dry DMF was added dropwise with stirring. After 5 min, racemic 1-(3-carbamoyl-4-cyclohexylmethoxyphenyl)ethylamine (120 mg, 0.43 mmol) in 0.8 mL of dry DMF was added dropwise. Stirring was continued at 0° C. for 1 hr. The reaction was quenched with 1 mL of saturated $NH_4Cl$, diluted with 17 mL of EtOAc. The organic layer was separated and washed with $H_2O$, 1 N HCl, $H_2O$, 5% $NAHCO_3$, and saturated $NH_4Cl$. The organic layer was dried over $Na_2SO_4$ and concentrated to give 253 mg (yield 66%) crude product as an oil.

(f) (5-{2-[1-(3-Carbamoyl-4-cyclohexylmethoxy-phenyl)ethyl]carbomoyl}-2-Phosphonomethoxy-phenyl)-phosphonic Acid To a solution of (5-{2-[1-(3-carbamoyl-4-cyclohexylmethoxy-phenyl)ethylcarbamoyl]ethyl}-2-diisopropylphosphonomethoxy phenyl)-phosphonic acid diethyl ester (253 mg, 0.34 mmol) in dry MeCN (3 mL) at −12° C. was added TMSI (1.02 mL, 7.2 mmol). The mixture was stirred for 3 hr at −12° C. and then quenched with saturated $NaHCO_3$ (4 mL), saturated $NaHSO_4$ (2 mL). The resulting mixture was purified by RP HPLC ($CH_3CN/H_2O$). Lyophilization left a white solid, 139.5 mg (yield 68%). Electrospray mass spectrum: m/z 597.45 (M−H).

Example 14

(5-{2-[1-(3-Carbamoyl-4-cyclohexylmethoxy-phenyl)ethylcarbamoyl]ethyl}-2-phosphonomethyl-phenyl)phosphonic Acid

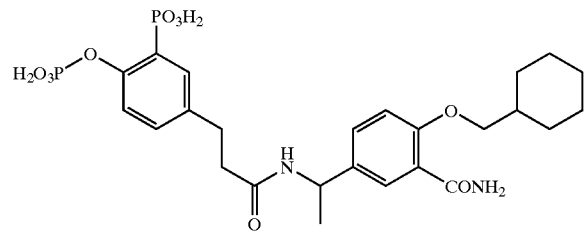

(a) 3-(3-Diethoxyphosphoryl-4-trifluoromethanesulfonyloxy-phenyl)-propionic Acid Methyl Ester 3-(3-Diethoxyphosphoryl-4-hydroxyphenyl)-propionic acid methyl ester (3.16 g, 10 mmol) and $PhNTf_2$ (3.93 g, 11 mmol) was dissolved in 30 mL dry DCM. The was cooled to 0° C. and $NEt_3$ (1.67 mL 12 mmol) was added dropwise. The reaction was stirred at 0° C. for 1 hr and slowly warmed to rt. The reaction mixture was diluted with 85 mL ether, then washed with $H_2O$, 1 N NaOH, $H_2O$, brine. The organic layer was dried over $MgSO_4$ and concentrated. Crude product was purified by flash column chromatography on silica gel (EtOAc/hexane 3:1, Rf=0.38) to obtain an oil 3.41 g (yield 78%).

(b) 3-(3-Diethoxyphosphoryl-4-vinyl-phenyl)propionic Acid Methyl Ester 3-(3-(diethoxyphosphoryl-4-trifluoromethanesulfonyloxy-pheny)-propionic acid methyl ester (1 g, 223 mmol) was dissolved in dry dioxane 25 mL together with vinyl tributyltin (0.67 mL, 229 mmol), LiCl (283 mg, 6.7 mmol), Pd(PPh$_3$)$_2$Cl$_2$ (47 mg, 0.067 mmol) and a crystal of 2,6-di-tert-butyl-4-methylphenol. Reaction mixture was degassed with Argon and heated to 98° C. and stirred for 2 hrs. Reaction mixture was cooled to rt and diluted with excess ether and 10 mL saturated aqueous KF solution and stirred at rt overnight. The reaction mixture was filtered through celite and separated organic layer was washed with 1 N HCl, brine, dried Na$_2$SO$_4$ and concentrated. Brownish oil was purified by flash column chromatography (EtOAc/hexane 90:10, Rf=0.50) to give an oil 470 mg (yield 65%).

(c) 3-(3-Diethoxyphosphoryl-4-formyl-phenyl)propionic Acid Methyl Ester 3-(3-Diethoxyphosphoryl-4-vinyl-phenyl)propionic acid methyl ester (200 mg, 0.61 mmol) was dissolved in 3.9 mL CCl$_4$ and 3.9 mL of MeCN. NaIO$_4$ (388 mg, 1.81 mmol) was dissolved in 6 mL H$_2$O and was added. The mixture was stirred vigorously and RuCl$_3$ (10 mg, 0.05 mmol) was then added and the mixture was stirred for 1 hr at rt The reaction was diluted with DCM, organic layer was separated, dried Na$_2$SO$_4$ and concentrated. The residue was purified by flash column chromatography on silica gel (4/1 EtOAc/hexane, Rf=0.37) to give pure product as an oil, 153 mg (yield 76%).

(d) 3-(3-Diethoxyphosphoryl-4-hydroxymethyl-phenyl) propionic Acid Methyl Ester 3-(3-Diethoxyphosphoryl-4-hydroxymethyl-phenyl) propionic acid methyl ester (328.3 mg, 1 mmol) and NaBH$_3$CN (67.0 mg, 1.1 mmol) were dissolved in 3 mL MeOH, a trace of methyl orange was added, and 2 N HCl/MeOH was added dropwise with stirring to maintain the red color. After ca. 15 min. the color changed very slowly. The stirring was continued for an additional 45 min. MeOH was evaporated. Residue was taken up in 3 mL of H$_2$O, saturated with NaCl, extracted with 3 mL (4×) of ether. Combined organic layer was dried MgSO$_4$ and concentrated to give crude product 330 mg (yield 100%).

(e) 3-(3-Diethoxyphosphoryl-4-bromomethyl-phenyl) propionic Acid Methyl Ester 3-(3-Diethoxyphosphoryl-4-hydroxymethyl-phenyl) propionic acid methyl ester (330 mg, 1 mmol), PPh$_3$ (289 mg, 1.1 mmol) and CBr$_4$ (365 mg, 1.1 mmol) were dissolved in 5 mL dry THF. The reaction mixture was stirred at 25° C. for 1 hr. The mixture turned cloudy. Solid was filtered and the filtrate was concentrated. The residue was further purified by flash column chromatography on silica gel (EtOAC/hexane 3/1, Rf=0.40). Pure product was obtained as an oil 150 mg (yield 38%).

(f) 3-(3-Diethoxyphosphoryl-4-diethoxyphosphorylmethyl-phenyl)propionic Acid Methyl Ester 3-(3-Diethoxyphosphoryl-4-diethoxyphosphoryl-phenyl) propionic acid methyl ester (150 mg, 038 mmol) was dissolved in P(OEt)$_3$ (2 mL, 11.4 mmol) and the reaction was heated at 130° C. for 1 hr. The volatile component was blown away by N$_2$ flow. The product was obtained as a clear oil 172 mg (yield: 100%).

(g) 3-(3-Diethoxyphosphoryl-4-diethoxyphosphorylmethyl-phenyl)propionic Acid

This compound was synthesized in a manner similar to that described in example 1.

(h) (5-{2-[1-(3-Carbamoyl-4-cyclohexylmethoxy-phenyl) ethylcarbamoyl]ethyl}-2-diethoxyphosphoryl-methyl-phenyl)-phosphonic Acid This compound was synthesized in a manner similar to that described in example 1.

(I) (5-{2-[1-(3-Carbamoyl-4-cyclohexylmethoxy-phenyl) ethylcarbamoyl]ethyl}-2-phosphonomethyl-phenyl)-phosphonic Acid This compound was synthesized in a manner similar to that described in example 1.

Example 15

N-(7-Carbonyl-1-hydroxynaphtho[1,2-c]furan-3 (1H)-one)-L-Glu-N(methyl)(3-cyclohexylpropyl)

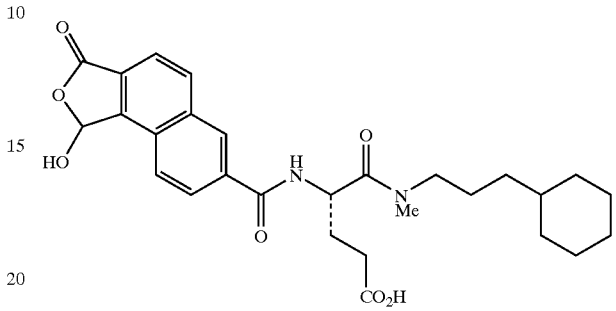

(a) Benzyl 5-Formyl-6-hydroxy-2-naphthoate

To a suspension of 5-formyl-6-hydroxy-2-naphthoic acid (1.12 g, 5.18 mmol) in 7.3 mL DMF at rt under N$_2$ was added 569 mg (5.69 mmol) of KHCO$_3$ and 1.11 mL (9.32 mmol) of benzyl bromide. The mixture was stirred for 3 days, at which point it was diluted with H$_2$O and extracted with EtOAc. The extract was washed with saturated aqueous NaHCO$_3$, dried over MgSO$_4$ and concentrated in vacuo. The crude material was purified by flash chromatography on silica gel, using 85:15 hexanes-EtOAc as the eluent, to give 410 mg (25%).

(b) Benzyl 5-Formyl-6-[[(trifluoromethyl)sulfonyl]oxy]-2-naphthoate

To a mixture of benzyl 5-formyl-6-hydroxy-2-naphthoate (410 mg, 1.33 mmol) in 6.25 mL of CH$_2$Cl$_2$ at rt under N$_2$ was added 0.28 mL (2.00 mmol) of Et$_3$N followed by 717 mg (2.00 mmol) of N-phenyltrifluoromethanesulfonimide. The mixture was stirred for 18 h at rt, diluted with saturated aqueous NaHCO$_3$ and extracted with CH$_2$Cl$_2$. The extract was dried over MgSO$_4$ and concentrated in vacuo. The crude material was purified by flash chromatography on silica gel. Elution with 4:1 hexanes-Et$_2$O afforded 560 mg (96%).

(c) 7-Benzyloxycarbonyl-1-methoxynaphtho[1,2-c]furan-3 (1H)-one

To a solution of benzyl 5-formyl-6-[[(trifluoromethyl) sulfonyl]oxy]-2-naphthoate 560 mg (1.27 mmol) in 3.6 mL of dry DMSO and 2.54 mL of dry MeOH at rt was added 0.39 mL (2.8 mmol) of Et$_3$N, 8.5 mg (0.038 mmol) of Pd(OAc)$_2$, and 15.6 mg (0.038 mmol) of bis (diphenylphosphino)propane. The mixture stirred under an atmosphere of CO (balloon) at rt for 1.5 h and then at 60° C. for 2 h. The mixture was then cooled to rt, diluted with H$_2$O and extracted with EtOAc followed by CHCl$_3$. The combined extracts were dried over MgSO$_4$ and concentrated In vacuo. The crude material was purified by flash chromatography on silica gel. Elution with 85:15 hexanes-EtOAc afforded a mixture of products. The mixture was diluted with Et$_2$O, washed with 10 mL of 1.0 M aqueous NaOH, H$_2$O and saturated aqueous NH$_4$Cl. The organic extract was dried over MgSO$_4$ and concentrated in vacuo affording 33 mg (10%).

(d) 7-Hydroxycarbonyl-1-methoxynaphtho[1,2-c]furan-3 (1H)-one

A mixture of 7-benzyloxycarbonyl-1-methoxynaphtho[1, 2-c]furan-3(1H)-one (33 mg, 0.095 mmol) and a catalytic amount of 10% Pd/C in 2 mL of EtOH was stirred at rt under an atmosphere of $H_2$ (balloon) for 2 h. The mixture was then diluted with THF and filtered through a pad of Celite. The filtrate was then concentrated in vacuo. The crude material was dissolved in saturated aqueous $NaHCO_3$ and washed with EtOAc. The aqueous layer was then acidified with 1 M aqueous HCl and extracted with EtOAc. The extract was dried over $MgSO_4$ and concentrated in vacuo affording 19 mg (79%).

(e) N-7-Carbonyl-1-methoxynaphtho[1,2-c]furan-3(1H)-one-L-Glu-(OtBu)-N(methyl)(3-cyclohexypropyl)

To a solution of 7-hydroxycarbonyl-1-methoxynaphtho[1,2-c]furan-3(1H)-one (19 mg. 0.074 mmol) and 30 mg (0.088 mmol) of L-Glu(OtBu)-N(methyl) (3-cyclohexylpropyl) (WO 97/12903) in 0.4 mL of $CH_2Cl_2$ was added 12 mg (0.088 mmol) of HOBT, 19.4 µL (0.111 mmol) of DIEA and 17 mg (0.088 mmol) of EDC. The solution was stirred for 4 h at which point it was poured into 1.0 M aqueous citric acid and extracted with $CH_2Cl_2$. The organic extract washed with half saturated aqueous $NaHCO_3$ and brine. The aqueous washes were reextracted with EtOAc, and the combined extracts were dried over $MgSO_4$ and concentrated in vacuo. The crude material was purified by flash chromatography on silica gel. Elution with EtOAc provided the title compound which was used directly in the next step.

(f) N-7-Carbonyl-1-hydroxynaphtho[1,2-c]furan-3(1H)-one-L-Glu-N(methyl)(3-cyclohexypropyl)

N-7-Carbonyl-1-methoxynaphtho[1,2-c]furan-3(1H)-one-L-Glu-(OtBu)-N(methyl)(3-cyclohexypropyl), from the previous step, was dissolved in 2 mL 95% aqueous TFA containing 50 µL of anisole. The solution was stirred for 75 min and then concentrated under a stream of $N_2$. The residue was purified by preparative reverse-phase HPLC. Elution with 50:50 MeCN-$H_2O$ (each containing 0.1% TFA) provided the methyl acetal of the title compound. This material was again subjected to the same reaction conditions and stirred for 36 h at rt. The reaction mixture was concentrated under a stream of $N_2$, and the remaining residue was again purified by preparative reverse-phase HPLC. Elution with 43:57 MeCN-$H_2O$ (each containing 0.1% TFA) afforded 4 mg of the title compound. $^1$H NMR (300 MHz, $CD_3CN$) δ 8.54 (s, 1H), 8.22 (m, 2H), 8.06 (d, J=8.7 Hz, 1H), 7.83 (d, J=8.5 Hz, 1H), 7.57 (m, 1H), 6.98 (s, 1H), 5.96 (br s, 1H), 5.10 (ddd, J=3.9, 8.9, 17.0 Hz, 1H), 3.57, 3.43 (m, m, 1H), 3.27 (m, 1.0H), 3.13, 2.90 (s, s, 3H), 2.45 (m), 230–1.90 (br m), 1.75–1.50 (br m), 1.30–1.10 (br m), 0.88 (m) ppm.

Example 16

N-(5-Carbonyl-3-hydroxynaphtho[2,3-c]furan-1 (3H)-one)-L-Glu-N(methyl)(3-cyclohexylpropyl)

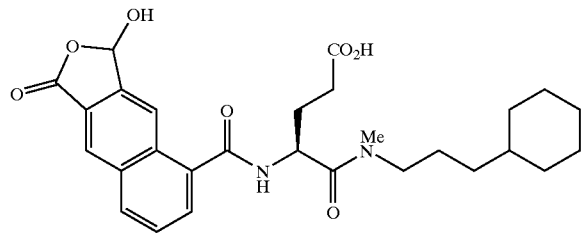

(a) Methyl 3,5-Dihydroxy-2-naphthoate

To a solution of 3,5-dihydroxy-2-naphthoic acid (5.05 g) in MeOH (100 mL) was added TsOH (93 mg). Tho reaction mixture was stirred at reflux for 18 hours and then $CH(OMe)_3$ (1 mL) was added. The reaction mixture was stirred at reflux for an additional 5 hours, at which point $H_2SO_4$ (10 drops) was added. After an additional 18 h, the reaction mixture was cooled to rt, poured into saturated aqueous $NaHCO_3$ and extracted with EtOAc. The extract was dried over $MgSO_4$ and concentrated in vacuo to give the title compound as a yellow-white solid (5.19 g, 96%).

(b) Methyl 3,5-Bis[[(trifluoromethyl)sulfonyl]oxy]-2-naphthoate

To a solution of methyl 3,5-dihydroxy-2-naphthoate (2.0 g, 9.17 mmol) in $CH_2Cl_2$ (43 mL) at rt was added $Et_3N$ (4.0 g, 5.6 mL, 40.3 mmol) followed by $PhNTf_2$ (7.2 g, 20.2 mmol). The solution was then stirred at rt for 18 hours. The reaction mixture was diluted with $Et_2O$ and washed with 1.0 M aqueous HCl. Th extract was dried over $MgSO_4$ and concentrated in vacuo. The crude material was chromatographed on silica gel (20:1 hexanes:EtOAc) to give a 1:1 mixture of the title compound and PhNHTf.

(c) Methyl 3,5-Diethenyl-2-naphthoate

To a solution of a 1:1 mixture of methyl 3,5-bis[[(trifluoromethyl)sulfonyl]oxy]-2-naphthoate and PhNHTf (3.24 g, 4.5 mmol) in DMF (11.25 mL) was added $(PPh_3)_2PdCl_2$ (158 mg, 0.23 mmol) and LiCl (1.14 g, 27.0 mmol). The mixture was stirred at rt for 20 min at which point $Bu_3SnCHCH_2$ (2.6 mL, 9.45 mmol) was added. The reaction mixture was heated for 90 min whereupon saturated aqueous KF was added. The resulting precipitate was filtered off and the filtrate extracted with EtOAc. The organic layer was washed with 1.0 M aqueous HCl, and the organic layer was dried over $MgSO_4$ and concentrated in vacuo. The crude material was chromatographed on silica gel (2% to 5% EtOAc/hexanes) to give the title compound (slightly impure as judged by $^1$H-NMR) as a clear oil. This material was used in the next reaction without further purification.

(d) Methyl 3,5-Diformyl-2-naphthoate $O_3$ was bubbled through a solution of slightly impure methyl 3,5-diethenyl-2-naphthoate (from the previous reaction) in $CH_2Cl_2$ (30 mL) and pyridine (2 mL) at −78° C. until a blue color persisted. Next, $Me_2S$ (2 mL) was added, producing a yellow color. The mixture warmed to rt over 18 h. All volatiles were then removed in vacuo. The crude material was chromatographed on silica gel (20:1 to 85:15 hexanes:EtOAc) to give the title compound (slightly impure as judged by $^1$H NMR). The material was used in the next step without further purification.

(e) 5-Formyl-3-hydroxynaphtho[2,3-c]furan-1(3H)-one

To a solution of the impure methyl 3,5-diformyl-2-naphthoate in THF (10 mL) at rt was added 1.0 M aqueous LiOH (5 mL, 5 mmol). After 1.5 hours, the reaction mixture was diluted with $H_2O$ and washed with $Et_2O$. The aqueous layer was acidified with 1.0 M aqueous HCl and extracted with EtOAc. The organic layer was dried over $MgSO_4$ and concentrated in vacuo to give the title compound (200 mg, 19% from methyl 3,5-diethenyl-2-naphthoate) as a white solid.

(f) 3-Acetoxy-5-formylnaphtho[2,3-c]furan-1(3H)-one

To a solution of 5-formyl-3-hydroxynaphtho[2,3-c]furan-1(3H)-one (190 mg, 0.83 mmol) pyridine (1.66 mL) at rt was added $Ac_2O$ (126 mg, 0.117 mL, 1.25 mmol). The solution was stirred at rt for 18 hours and then poured into brine and extracted with EtOAc. The extract was dried over $MgSO_4$ and concentrated The crude material was chromatographed on silica get (3:1 hexanes:EtOAc) to give the title compound (100 mg, 44%).

(g) 3-Acetoxy-5-hydroxycarbonylnaphtho[2,3-c]furan-1(3H)-one

To a solution of 3-acetoxy-5-formylnaphtho[2,3-c]furan-1(3H)-one (100 mg, 0.377 mmol) in MeCN (0.373 mL) and $H_2O$ (0.150 mL) at rt was added $NaH_2PO_4$ (15.3 mg, 0.097 mmol) followed by 50% $H_2O_2$ (0.026 mL). $NaClO_2$ (1.0 M in $H_2O$, 0.518 mL) was added over the course of 2 h via syringe pump. The reaction mixture was then diluted with saturated aqueous $NH_4Cl$ and extracted with EtOAc. The organic layer was dried over $MgSO_4$ and concentrated to give the title compound (87 mg, 80%).

(h) N-5-Carbonyl-3-hydroxynaphtho[2,3-c]furan-1(3H)-one)-L-Glu-N(methyl)(3-cyclohexylpropyl)

The title compound was synthesized in a manner similar to that described for example 15. Electrospray Mass Spectrum (50/50 acetonitrile/water +0.1% ammonium hydroxide) m/z 509 (M–H).

Example 17

N-6-Carbonyl-1-hydroxynaphtho[2,3-c]furan-1(1H)-one)-L-Glu-N(methyl)(3-cyclohexylpropyl)

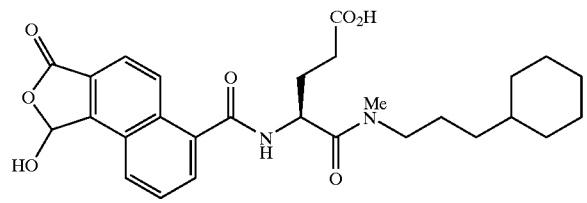

(a) 5-Formyl-hydroxy-1-naphthoic Acid

To a solution of 6-hydroxy-1-naphthoic acid (5.0 g, 37.6 mmol) in $CH_2Cl_2$ (60 mL) at 0° C. was added 1.0 M $TiCl_4$ in $CH_2Cl_2$ (80 mL, 80 mmol) dropwise. After 5 min, $Cl_2CHOCH_3$ (10.16 g, 88.14 mmol, 8 mL) was added. The reaction mixture was then warmed to room temperature and stirred overnight The reaction mixture was cooled to 0° C. and quenched with 100 mL $H_2O$, followed by 100 mL 1.0 M aqueous HCl. The resulting mixture was filtered, and the remaining solid was dissolved in 100 mL 1.0 M aqueous NaOH and filtered. The basic filtrate was acidified with 1.0 M aqueous HCl, and the resulting red solid was filtered and washed with 1.0 M aqueous HCl and $Et_2O$ to give the title compound.

(b) Methyl 5-Formyl-6-hydroxy-1-naphthoate

To a solution of 5-formyl-4-hydroxy-1-naphthoic acid (1.89 g, 8.75 mmol) in THF (200 mL) and EtOH (200 mL) was slowly added $CH_2N_2$ in $Et_2O$ until no SM remained by HPLC. The excess $CH_2N_2$ was quenched with a small amount of AcOH, and the volatiles were then removed in vacuo. The resulting crude material was chromatographed on silica gel (85:15 hexanes:EtOAc) to give the title compound.

(c) Methyl 5-Formyl-6-[(trifluoromethyl)sulfonyl]oxy-1-naphthoate

To a solution of methyl 5-formyl-6-hydroxy-1-naphthoate (500 mg, 2.17 mmol) in $CH_2Cl_2$ (10.2 mL) at rt was added $Et_3N$ (483 mg, 4.78 mmol, 0.664 mL) followed by $PhNTf_2$ (928 mg, 2.6 mmol). The mixture was stirred for 18 h and then diluted with $Et_2O$ and washed with 1.0 M HCl. The extract was dried with $MgSO_4$ and concentrated in vacuo. The crude material was chromatographed on silica gel (20:1 hexanes/EtOAc), and the material thus obtained was recrystallized from hexanes to give 1.0 g of a 3:2 mixture of the title compound and PhNHTf (~90% yield).

(d) 1-Methoxy-6-methoxycarbonylnaphtho[1,2-c]furan-3(1H)-one

To a solution of a 3:2 mixture of methyl 5-formyl-6-[(trifluoromethyl)sulfonyl]oxy-1-naphthoate (1.5 mmol) and PhNHTf in DMSO (4.5 mL) at rt was added $Pd_2(dba)_3$·$CHCl_3$ (155 mg, 0.217 mmol), and MeOH (4.34 mL). CO gas was bubbled through the mixture for 3 min and then $Et_3N$ (0.522 mL, 3.75 mmol) was added. The mixture was then heated to 60° C. CO gas was bubbled through the mire for another 10 min, and the mixture was stirred for an additional 30 min. The mixture was then poured into 1.0 M aqueous HCl and extracted with EtOAc. The organic layer was dried over $MgSO_4$ and concentrated in vacuo. The crude material was chromatographed on silica gel (20:1 hexanes:EtOAc) to give the title compound.

(e) 1-Hydroxy-6-hydroxycarbonylnaphtho[1,2-c]furan-3(1H)-one

To a solution of 1-methoxy-6-methoxycarbonylnaphtho[1,2c]furan-3(1H)-one (160 mg, 0.588 mmol) in THF (10 mL) at rt was added 1.0 M aqueous LiOH (2 mL, 2 mmol). The mixture was stirred for 2 h, acidified with 1.0 M HCl and extracted with EtOAc. The extract was dried over $MgSO_4$ and concentrated in vacuo. The resulting material was carried into next reaction.

(f) 6-Hydroxycarbonyl-1-methoxycarbonylnaphtho[1,2-c]furan-3(1H)-one

To a solution of 1-hydroxy-6-hydroxycarbonylnaphtho[1,2-c]furan-3(1H)-one in dry MeOH (15 mL) was added TsOH (150 mg) and $CH(OMe)_3$ (0.5 mL). The mixture was stirred at reflux for 2 h. The mixture was then cooled to rt, diluted with saturated aqueous $NaHCO_3$, acidified with AcOH and extracted with EtOAc. The extract was dried over $MgSO_4$ and concentrated in vacuo. The crude material was chromatographed on silica gel (85:15:1 to 66:33:1 hexanes:EtOAc:AcOH) to give the title compound (120 mg, 79% from 1-hydroxy-6-hydroxycarbonylnaphtho[1,2-c]furan-3(1H)-one).

(g) N-(6-Carbonyl-1-hydroxynaphtho[1,2-c]furan-3(1H)-one)-L-Glu-N(methyl)(3-cyclohexylpropyl)

The title compound was synthesized in a manner similar to that described for example 15. Electrospray Mass Spectrum (50/50 acetonitrile/water +0.1% ammonium hydroxide) m/z 509 (M–H).

Example 18

N-[5-Formyl-6-(hydroxycarbonyl)methoxynaphtho-2-yl]-L-Glu-N(methyl)(3-cyclohexylpropyl)

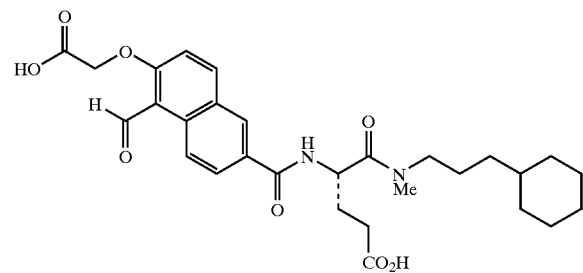

(a) N-[5-1,3-Dithiolan-2-yl)-6-[(1,1-dimethylethoxy)carbonyl]methoxynaphtho-2-yl]-L-Glu(O-1,1-dimethylethyl)-N(methyl)(3-cyclohexylpropyl)

To a solution of N-[5-(1,3-dithiolan-2-yl)-6-hydroxynaphtho-2-yl]-L-Glu(O-1,1-dimethylethyl)-N(methyl)(3-cyclohexylpropyl) (example 19) (89 mg, 0.144 mmol) in DMF (0.288 mL) at rt was added by t-butylbromoacetate (0.023 mL, 0.16 mmol), followed by $K_2CO_3$ (22.1 mg, 0.16 mmol). After 5 h, additional by t-butylbromoacetate (0.005 mL) was added and stirring was continued for an additional 1 h. The reaction mixture was then diluted with $H_2O$ and extracted with EtOAc. The organic layer was washed with brine, dried over MgSO$_4$ and concentrated in vacuo to give the title compound (65 mg, 59%).

(b) N-[6-[(1,1-Dimethylethoxy)carbonyl]methoxy-5-formylnaphtho-2-yl-L-Glu(O-1,1-dimethylethyl)-N(methyl)(3-cyclohexylpropyl)

To a solution of NBS (95 mg, 0.53 mmol) in MeCN (0.712 mL) and H$_2$O (0.190 mL) at 0° C. was added a solution of N-[5-(1,3-dithiolan-2-yl)-6-[(1,1-dimethylethoxy)carbonyl]methoxynaphtho-2-yl]-L-Glu(O-1,1-dimethylethyl)N(methyl)(3-cyclohexylpropyl) (65 mg, 0.089 mmol) in MeCN followed by 5×0.5 mL rinses. After 2.5 hours, the reaction mixture was diluted with EtOAc and poured into saturated aqueous NaHSO$_3$ (5 mL). The organic layer was washed with saturated aqueous NaHCO$_3$, H$_2$O and brine. The aqueous layers were acidified with 1.0 M aqueous HCl and extracted with EtOAc. The combined organic extracts were dried over MgSO$_4$ and concentrated in vacuo to give 70 mg of the title compound which was used without further purification.

(c) N-[5-Formyl-6-(hydroxycarbonyl)methoxynaphtho-2-yl]-L-Glu-N(methyl)(3-cyclohexylpropyl)

The title compound was synthesized in a manner similar to that described for example 15. Electrospray Mass Spectrum (50/50 acetonitrile/water +0.1% ammonium hydroxide) m/z 539 (M–H).

Example 19

N-(5-Formyl-6-phosphonooxynaphtho-2-yl)-L-Glu-N(methyl)(3-cyclohexylpropyl)

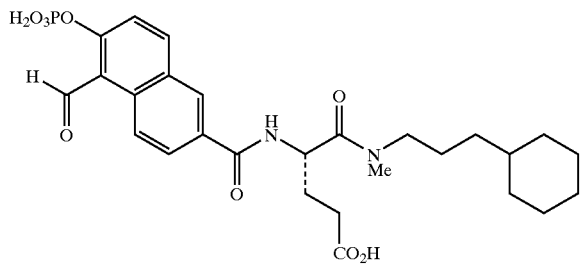

(a) 5-Formyl-6-hydroxy-2-naphthoic Acid

To a mixture of 941 mg (5.0 mmol) of 6-hydroxynaphthoic acid in 20 mL of (CH$_2$Cl)$_2$ at 0° C. under N$_2$ was added 1.0 mL (11.0 mmol) of CHCl$_2$OMe followed by 1.15 mL (10.5 mmol) of TiCl$_4$ (added slowly). The mixture was stirred at rt overnight, then cooled to 0° C. and diluted with 25 mL of 10% aq HCl. The mixture was extracted with 3:1 EtOAc-THY and the extract washed with 25 mL of 1 M aq HCl. The first aqueous layer, which had suspended solids, was filtered and the pink solid washed with 1 M aq HCl. The solid was dried under high vacuum over P$_2$O$_5$ affording 197 mg. The filtrate was reextracted once with 3:1 EtOAc-THF and washed with the second aqueous layer. The combined extracts wore concentrated in vacuo affording an additional 752 mg of about 90% purity. Electrospray Mass Spectrum (50/50 acetonitrile/water +0.1% ammonium hydroxide) m/z 215.06 (M–H).

(b) 5-(1,3-Dithiolan-2-yl)-6-hydroxy-2-naphtoic Acid

To a suspension of 184 mg (0.85 mmol) of 5-formyl-6-hydroxy-2-naphthoic acid in 4.2 mL of CH$_2$Cl$_2$ at 0° C. under N$_2$ was added 0.23 mL (1.79 mmol) of BF$_3$.OEt$_2$ followed by 0.07 mL of 1,2-ethanedithiol. The mixture was stirred at rt for 4 days. The mixture was then diluted with 10 mL of 1 M aq HCl and EtOAc. The resulting mixture was stirred vigorously for 45 min and then extracted with EtOAc. The organic layer was washed with 10 mL of H$_2$O followed by 10 mL of brine. The aqueous washes were reextracted once with EtOAc, and the combined extracts were dried over MgSO$_4$ and concentrated to a dark red solid. The material was purified by flash chromatography on silica gel. Elution with 20:1 CHCl$_3$-MeOH followed by 15:1 CHCl$_3$-MeOH afforded 164 mg (66%). TLC (15:1 CHCl$_3$-MeOH), R$_f$ 0.27. (cN-[5-(1,3-Dithiolan-2-yl)-6-hydroxynaphtho-2-yl]-L-Glu (O-1,1-dimethylethyl)-N(methyl(3-cyclohexylpropyl)

To a solution of 155 mg (0.530 mmol) of 5-(1,3-Dithiolan-2-yl)-6-hydroxy-2-naphthoic acid and 220 mg (0.557 mmol) of that L-Glu(OtBu)-N(methyl)(3-cyclohexylpropyl) (WO 97/12903) in 4 mL of 3:1 CH$_2$Cl$_2$-DMF at 0° C. under N$_2$ was added 0.14 mL (0.795 mmol) of DIEA, 97 mg (0.636 mmol) of HOBT, and 122 mg (0.636 mmol) of EDC. The mixture was stirred at rt for 3 h and then poured into 5 mL of 1 M aq citric acid. The mixture was extracted with EtOAc, and the extract was washed with 2×10 mL of H$_2$O and 1×10 mL of brine. The aqueous washes were reextracted once with EtOAc, and the combined extracts were dried over MgSO$_4$ and concentrated in vacuo to give 489 mg of a dark yellow residue. The crude material was purified by flash chromatography on silica get. Elution with 1:1 EtOAc/hexanes afforded 306 mg (94%) of a yellow gum. TLC (1:1 hexanes-EtOAc), R$_f$ 0.36.

(d) N-[6-Dibenzylphosphonooxy)-5-(1,3-dithiolan-2-yl)-naphtho-2-yl]-L-Glu(O-1,1-dimethylethyl)-N(methyl)(3-cyclohexylpropyl)

To a mixture of 305 mg (0.496 mmol) of N-[5-(1,3-Dithiolan-2-yl)-6-hydroxynaphtho-2-yl]-L-Glu(OtBu)-N(methyl)(3-cyclohexylpropyl) in 3.0 mL of CH$_3$CN at rt under N$_2$ was added 0.24 mL (248 mmol) of CCl$_4$ and 0.18 mL (1.04 mmol) of DIEA. The resulting solution was cooled to –5° C. resulting in the formation of a precipitate. To this mixture was added 6 mg (0.05 mmol) of DMAP followed by 0.16 mL (0.719 mmol) of dibenzylphosphite. The resulting solution was stirred for 45 min while warming to 5° C. The reaction mixture was then diluted with 1 mL of 0.5 M aq KH$_2$PO$_4$. The mixture was stirred vigorously for 10 min at rt, diluted with 5 mL of H$_2$O, and extracted with EtOAc. The extract was washed with 5 mL of H$_2$O and 5 mL of brine. The aqueous washes were reextracted once with EtOAc, and the combined extracts were dried over MgSO$_4$ and concentrated in vacuo to 490 mg. The crude material was purified by flash chromatography on silica gel. Elution with 1:1 EtOAc/hexanes followed by 3:2 EtOAc-hexanes afforded 413 mg (95%) of a light yellow gum. TLC (1:1 hexanes-EtOAc), R$_f$ 0.24.

(e) N-[(6-Dibenzylphosphonooxy)-5-formylnaphtho-2-yl-L-Glu(OtBu)-N(methyl)(3-cyclohexylpropyl)

To a solution of 500 mg (2.81 mmol) of NBS in 3.7 mL CH$_3$CN/1.0 mL H$_2$O at 0° C. was added a solution of 410 mg (4.069 mmol) of N-[6-(Dibenzylphosphonooxy)-5-(1,3-dithiolan-2-yl)-naphtho-2-yl]-L-Glu(O-1,1-dimethylethyl)-N (methyl)(3-cyclohexylpropyl) in 2.2 mL of CH$_3$CN followed by two 0.5 mL rinses. After 1.5 h, the reaction mixture was diluted with EtOAc and poured into 5 mL of saturated aq NaHSO$_3$. The layers were separated, and the organic extract was washed with 5 mL of saturated aq NaHCO$_3$, 5 mL of H$_2$O, and 5 mL of brine. The aqueous washes were reextracted once with EtOAc, and the combined extracts were dried over MgSO$_4$ and concentrated In vacuo to provide 492 mg of crude material. $^1$H-NMR revealed the presence of a significant amount of succinimide. Flash chromatography on silica silica gel eluting with EtOAc-hexanes failed to separate the desired compound from the succinimide, therefore the mixture was carried into the next step.

(f) N-5-Formyl-6-phosphonooxynaphtho-2-yl)-L-Glu-N(methyl)(3-cyclohexylpropyl)

A solution of 473 mg of a mixture of N-[(6-dibenylphosphonooxy)-5-formylnaphtho-2-yl-Glu(O-1,1-dimethylethyl)-N(methyl)(3-cyclohexylpropyl) and succinimide in 4.1 mL of 95% aq TFA containing 0.1 mL of anisole was stirred at rt for 3 h. The solution was concentrated under a stream of $N_2$. The remaining dark pink residue was purified by reverse phase HPLC. Gradient elution from $H_2O$ containing 0.1% TFA to $CH_3CN$ containing 0.1% TFA afforded 143 mg (54% from N-[6-(Dibenzylphosphonooxy)-5-(1,3-dithiolan-2-yl)-naphtho-2-yl]-L-Glu(O-1,1-dimethylethyl) N(methyl)(3-cyclohexylpropyl) of the title compound as a white solid. Electrospray Mass Spectrum (50/50 acetonitrile/water +0.1% ammonium hydroxide) m/z 561.27 M–H). $^1$H NMR (300 MHz, DMSO-$d_6$) d 10.70 (s, 1H), 9.15 (d, J=9.0 Hz, 1H), 8.74 (dd, J=16.0, 8.0 Hz, 1H), 8.59 (d, J=2.6 Hz, 1H), 8.39 (d, J=9.1 Hz, 1H), 8.15 (dd, J=8.9, 2.6 Hz, 1H), 7.68 (d, J=9.0 Hz, 1H), 4.98 (br, 1H), 3.58–3.16 (m, 2H), 3.11, 2.83 (s, s, 3H), 2.37 (br, 2H), 1.96–1.91 (m, 2H), 1.64–1.45 (m, 7H), 1.12–1.09 (m, 6H), 0.88–0.81 (m, 2H) ppm.

Example 20

N-[-(5-Phosphonoxyindol-2-yl)carbonyl]-Glu(Otbu)-N(methyl)(3-cyclohexylpropyl)

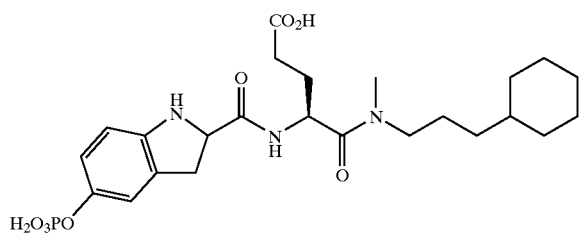

(a) N-[(5-Hydroxyindol-2-yl)carbonyl]-L-Glu(OtBu)-N(methyl)(3-cyclohexylpropyl)

To 5-hydroxy-2-indolecarboxylic acid (1.64 mmol, 0.291 g) in dichloromethane (20 mL) was added and L-Glu(OtBu)-N(methyl)(3-cyclohexylpropyl) (1.64 mmol, 0.562 g) followed by addition of 1-(3-dimethylaminopropyl)3-ethyl-carbodiimide hydrochloride (1.64 mmol, 0.315 g) and HOBT (1.64 mmol, 0.222 g). After stirring 14 h at rt, the reaction mixture was concentrated. The residue was taken up in ethyl acetate (50 mL) and washed successively with 10% hydrochloric acid (50 mL), water (50 mL), aqueous saturated sodium bicarbonate (50 mL) and brine (50 mL). The organic layer was dried over magnesium sulfate, concentrated, and chromatography of the residue (2:1, hexane/ethyl acetate) gave the product as a white solid (0.626 g, 77%). TLC: Rf 0.80 2/1 hexanes/ethyl acetate; MS: (50/50 acetonitrile/water). MS [M+H]$^+$ 500.

(b) N-[(5-Dibenzylphosphonoxyindol-2-yl)carbonyl]-L-Glu(OtBu)-N(methyl)(3-cyclohexylpropyl)

This compound was prepared following the procedure of example 16, step d. MS [M+H]$^+$ 760.

(c) N-[(5-Phosphonoxyindol-2-yl)carbonyl]-L-Glu(OtBu)-N(methyl)(3-cyclohexylpropyl)

This compound was prepared following the procedure of example 16, step f. The crude material was purified by HPLC to yield a white solid (25 mg). MS: (50/50 acetonitrile/water) MS (M+H]$^+$ 524; $^1$H NMR (300 MHz, DMSO): δ 735 (m, 2H), 720 (s, 1H), 7.00 (s, 1H), 4.95 (bs, 1H), 3.05 (m, 2H), 2.80 (s, 1H), 2.30 (m, 2H), 1.65 (m, 12H), 1.40 (t, 3H), 1.12 (m, 5H).

Example 21

[(4-{(S)-2-Acetylamino-(S)-2-[1-(4-carbamoyl-7,8-dihydro-6H-5-oxa-9-thia-benzocyclohepten-2-yl)-ethylcarbomoyl]-ethyl}-phenyl)-difluoro-methyl] phosphonic Acid

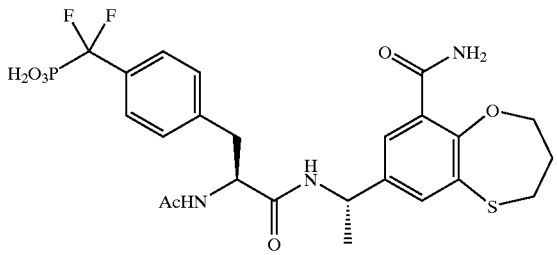

(a) 2-(3-Hydroxy-propylsulfanyl)phenol

2-Hydroxythiophenol (1.00 g, 8.70 mmol) was added to a mixture of DMF (10 mL) and $Cs_2CO_3$ (2.90 g, 8.90 mmol). To this was added 3-bromopropanol (0.80 mL, 9.16 mmol) and the mixture was stirred for 20 min. The mixture was added to into water and extracted with EtoAc. The combined extracts were washed with water, dried over magnesium sulfate and concentrated to a clear oil (236 g, 100%). MS [M–H]$^-$ 183.

(b) 7,8-Dihydro-6H-5-oxa-9-thia-benzocycloheptene

To 2-(3-hydroxy-propylsulfanyl)-phenol (29.2 g, 158.5 mmol) in THF (450 mL) was added triphenylphosphine (52.0 g, 200.0 mmol). The solution was cooled to –40° C. and diethyl azodicarboxylate (31.5 mL, 164.0 mmol) was added slowly. The solution was warmed to rt and stirred for 2.5 h. The THF was removed by evaporation and the residue was treated with 1 L of $Et_2O$. The formed solids were filtered off, and the filtrate concentrated to an oil which was purified over silica gel (10% $Et_2O$/hexane) to a pink oil (16.2 g, 61%).

(c) 7,8-Dihydro-6H-5-oxa-9-thia-benzocycloheptene-4-carboxylic Acid

To 7,8-dihydro-6H-5-oxa-9-thia-benzocycloheptene (16.2 g, 97 mmol) in 250 mL of dry hexane was added tetramethylethylene diamine (16 mL, 106 mmol). The solution was cooled to 0° C. and n-butyllitium (1.6 M solution in hexane, 73 mL, 116.8 mmol) was slowly added with stirring. A tan-colored precipitate slowly started to form and some gas evolution occured. The suspension was stirred at rt for 18 h, after which $CO_2$ gas was bubbled though it for 20 min. An exothermic reaction occured. The mixture was diluted with 300 mL ethyl acetate and 4 N HCl. After all solids dissolved, the organic layer was washed with 1 N HCl. The acid was extracted into 10 tho water layer using sat. $NaHCO_3$. The aqueous layer was washed with ethyl acetate and treated with 10 N HCl to pH 1. Extraction with ethyl acetate (2×250 mL), drying over $Na_2SO_4$ and concentration yielded the compound as a tan solid (16.5 g, 81%). MS [M–H]$^-$ 209.

(d) 7,8-Dihydro-6H-oxa-9-thia-benzocycloheptene-4-carboxylic Acid Amide

To 7,8-dihydro-6H-5-oxa-9-thia-benzocycloheptene-4-carboxylic acid (16.5 g, 78.4 mmol) in 100 mL DMF was added in succession solid HOBT (213 g, 1573 mmol), solid EDC hydrochloride (30.1 g, 157.0 mmol), and 25% aqueous ammonia (18 ml, 128.4 mmol). After stirring for 48 h, the reaction mixture was diluted with 200 mL ethyl acetate and washed with water, 1N HCl, saturated $NaHCO_3$, sated $NH_4Cl$, and brine. Drying over $Na_2SO_4$ and concentration yielded the amide as a tan solid (10.5 g, 64%).

(e) 5-Acetyl-3-(3-chloro-propylsulfanyl)-2-hydroxy-benzamide

Solid aluminum chloride (9.0 g, 67.7 mmol) was suspended in 20 mL of dry dichloromethane at 0° C. The 7,8-dihydro-6H-5-oxa-9-thia-benzocycloheptene-4-carboxylic acid amide (2.7 g, 12.7 mmol) was added as a solution in 20 mL dichloromethane. The deep green solution was stirred at 0° C. for 10 min. then neat acetyl chloride (10 mL, 140.6 mmol) was added dropwise with stirring. The suspension was stirred at 0° C. for 20 min, then at rt for 30 h. The reaction was quenched with 4 N HCl and extracted repeatedly with ethyl acetate. Drying over $Na_2SO_4$ and concentration yeilded the crude product Sgc (ethyl acetate) yielded the product as a tan solid (1.6 g, 44%). MS [M–H]⁻ 286.

(f) 2-Acetyl-7,8-dihydro-6H-5-oxa-9-thia-benzocycloheptene-4-carboxylic Acid Amide The 5-acetyl-3-(3-chloro-propylsulfanyl)-2-hydroxy-benzamide (2.87 g, 10 mmol) was dissolved in 8 mL dry DMF. Solid $Cs_2CO_3$ (4.93 g, 15.1 mmol) was added, followed by catalytic amounts of KI (0.1 g). The suspension was warmed to 70° C. under nitrogen and was stirred for 72 h. After cooling, it was diluted with ethyl acetate and enough 4 N HCl to make the pH about 2. The aqueous layer was extracted with more ethyl acetate. The combined organic layers were washed with water and brine. Drying over $Na_2SO_4$ and concentration yielded the product as a solid (1 g, 40%).

(g) 2-(1-Hydroxy-ethyl)-7,8-dihydro-6H-5-oxa-9-thia-benzocycloheptene-4-carboxylic Acid Amide To 2-acetyl-7,8-dihydro-6H-5-oxa-9-thia-benzocycloheptene-4-carboxylic acid amide (0.40 g, 1.59 mmol) suspended in EtOH (10 mL) was added $NaBH_4$ (0.060 g, 1.59 mmol). The mixture was stirred for 5 min. made acidic with 1 N HCl, and the EtOH removed in vacuuo. The aqueous was extracted with EtOAc. The combined extracts were washed with water, dried over magnesium sulfate and concentrated to a foam (0.35 g, 87%). MS [M+H]⁺ 252.

(h) 2-(1-Azido-ethyl)-7,8-dihydro-6H-5-oxa-9-thia-benzocycloheptene-4-carboxylic Acid Amide This compound was prepared as for example 1 (d). (0.26 g, 66%).

(i) 2-(1-Amino-ethyl)-7,8-dihydro-6H-5-oxa-9-thia-benzocycloheptene-4-carboxylic Acid Amide To 2-(1-(azido-ethyl)-7,8-dihydro-6H-5-oxa-9-thia-benzocycloheptene-4-carboxylic acid amide (0.20 g 0.73 mmol) in THF (5 mL) was added water (0.10 mL) and triphenylphosphine (0.19 g, 0.73 mmol). The mixture was heated to 50° C. for 20 h, evaporated, and chomatographed over silica gel (10% MeOH/CHCl₃) to give a colorless oil (0.10 g, 55%).

(j) [(4-{(S)-2-Acetylamino-(S)-2-[1-(4-carbamoyl-7,8-dihydro-6H-oxa-9-thia-benzocyclohepten-2-yl)-ethylcarbomoyl]-ethyl}-phenyl)-difluoro-methyl]-phosphonic Acid This compound was prepared as for example 3 (a–b). MS [M+H]⁺ 572.

What is claimed is:
1. A compound of the formula:

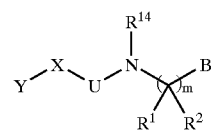

I wherein
Y is

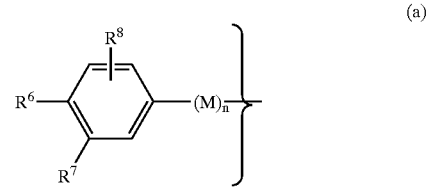

(a)

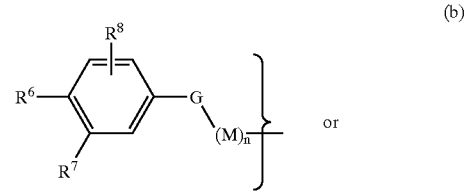

(b)

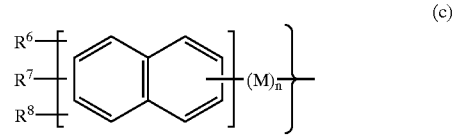

(c)

G is —O—, —S— or —N—;
R⁶ comprises —APO₃RR', —OPO₃RR', —ASO₃R, —OSO₃R, —ACO₂R, —A-tetrazole, —ASO₂NRR', —ACOCF₃, —C(O)J, —C(R)(J)(K) or —C(Z)(J)(K);
where each occurrence of A is independently a covalent bond, —G—M— or —(M)$_m$—;
each occurrence of M is an independently selected, substituted or unsubstituted, methylene moiety, and any M—M' moiety may be electronically saturated or unsaturated;
each n is independently 0, 1, 2, 3, 4 or 5;
each m is independently 0, 1 or 2;
J and K are independently —APO₃RR', —OPO₃RR', —ASO₃R, —OSO₃R, —ACO₂R, —A-tetrazole, —ASO₂NRR', —(M)$_n$—NRR' or —(M)$_n$—OR;
Z is a halogen;
R⁷ and R⁸ are independently R, —CN, —NO₂, Z, J, —A(M)$_n$aliphatic, —G(M)$_n$aliphatic, —(M)$_n$COR) —(M)$_n$OR, —(M)$_n$COOR, —A—(M)$_n$NRR', —G(M)$_q$NRR', —(M)$_n$CHO, —A(M)$_n$N(R)(CO)R', —A(M)$_n$N(R)(CO)GR', —G(M)$_n$N(R)(CO)R', —G—(M)$_n$N(R)(CO)G'R', —A—(M)$_n$—CO—NRR', or —G(M)$_n$—CO—NRR, where the aliphatic groups may be substituted or unsubstituted; or R⁸ is a covalent bond to an R⁴ substituent of X to form an aliphatic, aryl or heterocyclic ring of 4 to 8 atoms which may be saturated or unsaturated;
each occurrence of R (unnumbered) represents hydrogen or an aliphatic, heteroaliphatic, aryl, heteroaryl, (aryl) aliphatic-, or (heteroaryl)aliphatic-moiety, each of which (other than hydrogen) may be substituted or unsubstituted;

q is an integer from 1 to 8;

$R^1$ is hydrogen, aliphatic, $—(M)_n$-cycloaliphatic, $—(M)_n$-aryl, or $—(M)_n$-heterocyclic, each of which, other than H, may be substituted or unsubstituted; and $R^2$ is hydrogen or substituted or unsubstituted aliphatic;

or $R^1$ and $R^2$ are covalently linked together to form a ring;

or $R^1$ or $R^2$ are covalently linked to B or a substituent of B to form a 4–0-membered ring (which may be saturated or unsaturated);

X is: $—(CR^3R^4)_m—$ or $—NR^4—$;

$R^3$ is hydrogen, R(CO)NR'—, RR'N(CO)NR"—, R'SO$_2$NR—, R'C(S)NR—, RR'NCSNR"—, RR'NSO$_2$NR"—, R'OCONR—, RR'N—, or

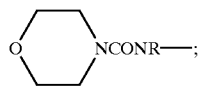

$R^4$ is hydrogen, aliphatic, cycloaliphatic-$(M)_n$—, aryl-$(M)_n$—, heterocyclic-$(M)_n$—, R—SO$_2$M$_n$—, (RO—CO)$(M)_n$— or (RR'N—CO)$(M)_n$—, where the aliphatic, cycloaliphatic, aryl or heterocyclic moiety is substituted or unsubstituted;

B is

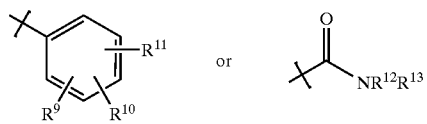

where $R^9$, $R^{10}$ and $R^{11}$ are independently selected from $—(M)_nR$, $—G(M_n)R$, $—(M)_nZ$, $—(M)_nCN$, $—(M)_nGR$, $—(M)_nNRWR$, $—(M)_nNRW—GR$, $—(M)_nW—R$, $—G—(M)_nW—R$, and $—(M)_nW—GR$, or $R^{10}$ and $R^{11}$ are covalently linked together to form an aliphatic, hetercyclic or aryl fused ring;

$R^{12}$ and $R^{13}$ are independently selected from the group consisting of hydrogen, aliphatic, heteroaliphatic, aryl, heteroaryl, (aryl)aliphatic-, or (heteroaryl)aliphatic, each of which (other than hydrogen) may be substituted or unsubstituted; or $R^{12}$ and $R^{13}$ are covalently linked together to form a heterocyclic moiety;

$R^{14}$ is R; and,

U and W are independently —CO—, —CS—, —M—, —SO—, or —SO$_2$—;

such that in embodiments in which $R^6$ is (H$_2$O$_3$P)$_2$CH—, $R^7$ and $R^8$ are H, B is —C(O)NRR', and X is —CHNR—, then $R^4$ is a group other than —NHOR where R is H, substituted or unsubstituted benzyl, trialkylsilyl, t butyldiphenylsilyl, tetrahydropyranyl or t-butyl; and in embodiments in which Y is of the structure (a), shown above, where $R^6$ is —OPO$_3$RR', —CF$_2$PO$_3$RR', —CH$_2$PO$_3$RR', —SO$_3$R, —OSO$_3$R, —CH$_2$SO$_3$R, —SO$_2$NH$_2$, or —CH$_2$SO$_2$NH$_2$; and B is —C(O)NRR' or

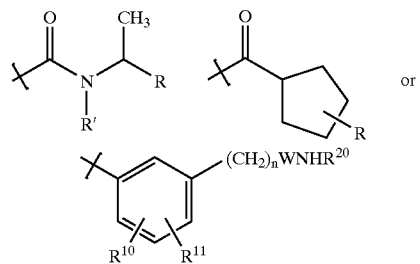

where $R^{10}$ is H, Z or alkyl; $R^{11}$ is H, alkyl, —OR, —O(CH$_2$)$_n$aryl, —NRR', —O(CH$_2$)$_n$-substituted alkyl, —SR, —(CH$_2$)$_n$-substituted aryl or —(CH$_2$)$_n$-cycloalkyl; and $R^{20}$ is H, substituted or unsubstituted alkyl, —OH or —NH$_2$, where the R groups are independently H, alkyl, cycloalkyl —(CH$_2$)$_n$—, aryl —(CH$_2$)$_n$—, heteroaryl-(CH$_2$)$_n$—, or —(CH$_2$)(CH$_2$)$_n$—COOH, where the alkyl, cycloalkyl, aryl and heteroaryl moieties are substituted or unsubstituted, then $R^7$ and $R^8$ are both a moiety other than H or Me, or $R^7$ is a moiety other than Cl;

or a pharmaceutically acceptable derivative thereof.

2. A compound of claim 1 of the formula:

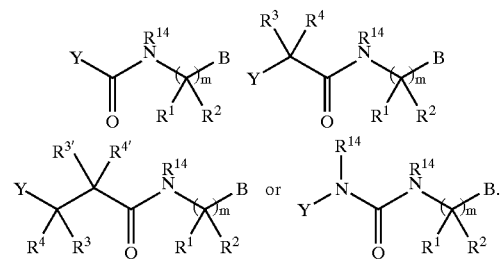

3. A compound of claim 2 containing a $R^4$ moiety which is H.

4. A compound of claim 2 in which $R^3$ and $R^4$ are H.

5. A compound of claim 1 wherein n is 0, 1 or 2.

6. A compound of claim 2 wherein n is 0, 1 or 2.

7. A compound of claim 1 wherein X is —CH(NH$_2$)—.

8. A compound of claim 1 of the formula

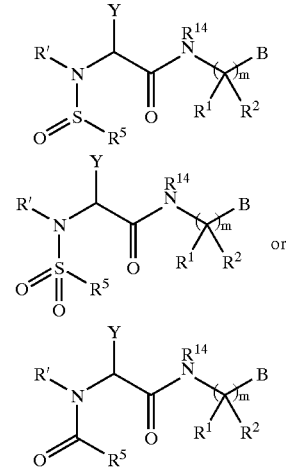

where $R^5$ comprises a substituted or unsubstituted lower aliphatic or alkoxyl or is a substituted or unsubstituted $—(M)_n$-aryl or $—(M)_n$-heterocyclic group.

9. A compound of claim 8 wherein $R^5$ comprises —$(M)_n$CH$_3$, —$(M)_n$aryl, —$(M)_n$heterocyclic, —$(M)_n$CN or —$(M)_n$COOR, where n is 0, 1, 2, 3, 4, or 5.

10. A compound of claim 8 wherein $R^5$ is a methyl, ethyl, propyl, butyl, pentyl, hexyl, benzyl, aryl, heterocyclic, —(CH$_2$)-aryl or —(CH$_2$)-heterocyclic moiety, which may be substituted or unsubstituted.

11. A compound of claim 8 wherein $R^5$ comprises —(CH$_2$)CH$_3$, —(CH$_2$)(CH$_2$)$_n$aryl, —(CH$_2$)(CH$_2$)$_n$heterocyclic, —(CH$_2$)(CH$_2$)$_n$CN, or —(CH$_2$)(CH$_2$)$_n$COOR, where n is 0, 1, 2, 3, 4, or 5.

12. A compound of claim 11 wherein $R^5$ comprises —CH$_2$CN, —(CH$_2$)COOR, —(CH$_2$)$_2$COOR, —(CH$_2$)$_3$COOR, —(CH$_2$)$_4$COOR, where R is H, lower alkyl or benzyl.

13. A compound of claim 11 wherein $R^5$ comprises —O-(substituted or unsubstituted lower alkyl or benzyl).

14. A compound of claim 1 of the formula

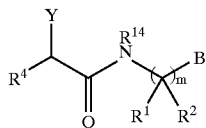

where $R^4$ is hydrogen, substituted or unsubstituted aliphatic (which may be branched, unbranched or cyclic), substituted or unsubstituted aryl-$(M)_n$—, substituted or unsubstituted heterocyclic-$(M)_n$—, or $(CO_2R)(M)_n$—.

15. A compound of claim 14 wherein $R^4$ is —$(M)_n$(CO)OR, —$(M)_n$SO$_2$R, —$(M)_n$(CO)NRR', or —$(M)_n$(tetrazole).

16. A compound of claim 15 wherein $R^4$ is —CH$_2$COOR, —CH$_2$SO$_2$R, —CH$_2$(CO)NRR', or -tetrazole.

17. A compound of claim 15 wherein each R and R' is independently H, lower alkyl or benzyl.

18. A compound of claim 1 of the formula

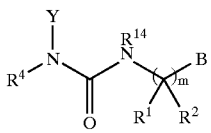

where $R^4$ is hydrogen, substituted or unsubstituted aliphatic (which may be branched, unbranched or cyclic), substituted or unsubstituted aryl-$(M)_n$—, substituted or unsubstituted heterocyclic-$(M)_n$—, or $(CO_2R)(M)_n$—.

19. A compound of claim 18 wherein $R^4$ is hydrogen.

20. A compound of claim 1 of the formula

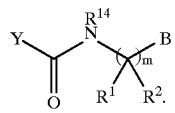

21. A compound of claim 8 wherein R and R' are H.

22. A compound of any of claims 9–13 wherein R and R' are H.

23. A compound of any of claims 1–20 wherein $R^{14}$ is H.

24. A compound of claim 22 wherein $R^{14}$ is H.

25. A compound of any of claims 1–21 and 6, having the formula:

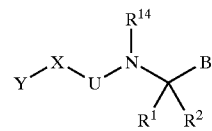

wherein $R^1$ is H, and $R^2$ comprises H, —$(M)_n$H, —$(M)_n$-substituted or unsubstituted lower alkyl), —$(M)_n$-substituted or unsubstituted aryl), —$(M)_n$-substituted or unsubstituted heterocyclic), —$(M)_n$COOR, or —$(M)_n$(CO)NRR'.

26. A compound of claim 25, wherein $R^2$ is methyl, ethyl, i-propyl, n-,propyl, n-butyl, isobutyl, n-amyl, sec-amyl, isoamyl, substituted benzyl, —CH$_2$-(3-indolyl), —CH$_2$CH$_2$COOR, —CH$_2$CH$_2$CONH$_2$, —CH$_2$COOR or —CH$_2$CONH$_2$.

27. A compound of claim 25, wherein R, R', R14 are H.

28. A compound of any of claims 1–21 and 6, wherein $R^1$ and $R^2$ are independently selected, substituted or unsubstituted lower aliphatic groups, or $R^1$ and $R^2$ are covalently linked to each other to form a ring.

29. A compound of any of claims 1–21 and 6, having the formula

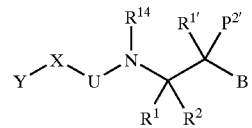

wherein each of $R^1$, $R^{1'}$, $R^2$, and $R^{2'}$ is independently selected from H, —$(M)_n$H, —$(M)_n$-(substituted or unsubstituted lower alkyl), —$(M)_n$-(substituted or unsubstituted aryl), —$(M)_n$-(substituted or unsubstituted heterocyclic), —$(M)_n$—COOR and —$(M)_n$(CO)NRR'.

30. A compound of claim 25, wherein each of $R^1$, $R^{1'}$, $R^2$, and $R^{2'}$ is H.

31. A compound of any of claims 1–21 and 6, wherein at least one of $R^1$ and $R^2$ is methyl, ethyl, i-propyl, n-propyl, n-butyl, isobutyl, t-butyl, n-amyl, sec-amyl, isoamyl, substituted benzyl, —CH$_2$-(3-indolyl), —CH$_2$CH$_2$COOR, —CH$_2$CH$_2$CONH$_2$, —CH$_2$COOR or —CH$_2$CONRR', or $R^1$ and $R^2$ are covalently linked to form a ring.

32. A compound of claim 28, wherein at least one of $R^1$ and $R^2$ is methyl, ethyl, i-propyl, n-propyl, n-butyl, isobutyl, t-butyl, n-amyl, sec-amyl, isoamyl, substituted benzyl, —CH$_2$—(3-indolyl), —CH$_2$CH$_2$COOR, —CH$_2$CH$_2$CONH$_2$, —CH$_2$COOR or —CH$_2$CONRR', or $R^1$ and $R^2$ are covalently linked to form a ring.

33. A compound of claim 29, wherein at least one of $R^1$, $R^{1'}$, $R^2$, and $R^{2'}$ is methyl, ethyl, i-propyl, n-propyl, n-butyl, isobutyl, t-butyl, n-amyl, sec-amyl, isoamyl, substituted benzyl, —CH$_2$-(3-indolyl), —CH$_2$CH$_2$COOR, —CH$_2$CH$_2$CONH$_2$, —CH$_2$COOR or —CH$_2$CONRR', or two of $R^1$, $R^{1'}$, $R^2$, and $R^{2'}$ are covalently linked to form a ring.

34. A compound of any of claims 1–21 and 6, wherein Y comprises

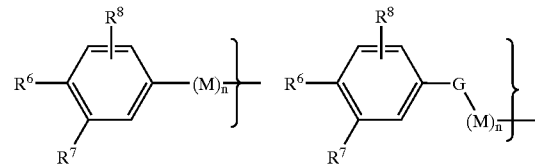

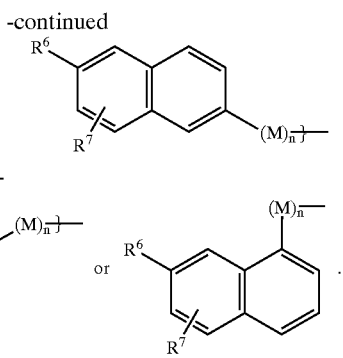

35. A compound of claim 34 wherein
R⁶ comprises —APO₃RR', —OPO₃RR', —ASO₃R, —OSO₃R, —ACO₂R, —A-tetrazole, —ASO₂NRR', —ACOCF₃, —C(R)(J)(K) or —C(Z)(J)(K); and
R⁷ and R⁸ are independently H, —CN, —NO₂, halogen, J, —A—(M)ₙaliphatic, —G—(M)ₙaliphatic, —(M)ₙ COCF₃, —(M)ₙOH, —(M)ₙCOOR, —A—(M)ₙNRR', —G—(M)ₙNRR', —(M)ₙCHO, —A—(M)ₙN(R)(CO) R', —G—(M)ₙN(R)(CO)R', —A—(M)ₙ—CO—NRR', or —G—(M)ₙ—CO—NRR', where the aliphatic groups may be substituted or unsubstituted; or R⁷ is a covalent bond to an R⁴ substituent of X to form an aliphatic, aryl or heterocyclic ring of 4 to 8 atoms.

36. A compound of claim 34 wherein
R⁶ comprises —APO₃RR', —OPO₃RR', —ACO₂R, —ACOCF₃ or —C(R)(J)(K);
A comprises —CH₂—, —OCH₂—, —CF₂—, —CHF—, —CHOH— or a covalent bond;
each R and R' is H, or substituted or unsubstituted lower alkyl or substituted or unsubstituted benzyl; and,
R⁷ and R⁸ are independently H, J, —A—(M)ₙsubstituted or unsubstituted aliphatic, —G—(M)ₙsubstituted or unsubstituted aliphatic, —(M)ₙCOCF₃, —(M)ₙOH, —(M)ₙCOOR, —A—(M)NRR', —(M)ₙCHO, —A—(M)ₙN(R)(CO)R' or —A—(M)ₙ—CO—NRR.

37. A compound of claim 34 wherein R⁶ comprises —PO₃RR', —OPO₃RR', —CH₂PO₃RR', —CF₂PO₃RR', —OCH₂CO₂R, —NHCH₂CO₂R, —CH₂CO₂R, —CF₂CO₂R, —CH₂SO₃R, —CF₂SO₃R, —CH₂COCF₃, —CF₂COCF₃, —CH(PO₃RR)₂, —CH(OH)(PO₃RR'), —CH(NH₂)(PO₃RR'), —CH(CO₂R)₂, —CF(CO₂R)₂, —CH(PO₃RR')(CO₂R"), —CH(PO₃RR')(SO₃R"), —CH (PO₃RR')(SO₂NH₂), —CH(SO₂NH₂)₂, or —CH(SO₃RR')₂.

38. A compound of claim 37 in which one or more of R, R' and R" in the —PO₃RR', —OPO₃RR', —CH₂PO₃RR', —CF₂PO₃RR', —OCH₂CO₂R, —NHCH₂CO₂R, —CH₂CO₂R, —CF₂CO₂R, —CH₂SO₃R, —CF₂SO₃R, —CH₂COCF₃, —CF₂COCF₃, —CH(PO₃RR')₂, —CH(OH)(PO₃RR'), —CH(NH₂)(PO₃RR'), —CH(CO₂R)₂, —CF(CO₂R)₂, —CH(PO₃RR')(CO₂R"), —CH(PO₃RR')(SO₃R"), —CH(PO₃RR')(SO₂NH₂), —CH(SO₂NH₂)₂, or —CH(SO₃RR')₂ moiety is H.

39. A compound of claim 37 in which one or more of R, R' and R" in the —PO₃RR', —OPO₃RR', —CH₂PO₃RR', —CF₂PO₃RR', —OCH₂CO₂R, —NHCH₂CO₂R, —CH₂CO₂R, —CF₂CO₂R, —CH₂SO₃R, —CF₂SO₃R, —CH₂COCF₃, —CF₂COCF₃, —CH(PO₃RR')₂, —CH(OH)(PO₃RR'), —CH(NH₂)(PO₃RR'), —CH(CO₂R)₂, —CH(PO₃RR')(CO₃R"), —CH(PO₃RR')(SO₃R"), —CH(PO₃RR')(SO₂NH₂), —CH(SO₂NH₂)₂, or —CH(SO₃RR')₂ moiety is —(M)ₘCH₂Z, —(M)ₘCHZ₂, —(M)ₘCZ₃, —R¹⁵, —M—O—R¹⁵ or —M—O—CO—OR¹⁵, where Z is halogen and R¹⁵ is substituted or unsubstituted lower aliphatic, aryl or heterocyclic.

40. A compound of claim 39 in which R¹⁵ is methyl, ethyl, n-propyl, i-propyl, n-butyl, isobutyl, t-butyl, n-amyl, sec-amyl, benzyl or substituted benzyl.

41. A compound of any of claims 37–40 wherein R⁷ and R⁸ are H.

42. A compound of any of claims 37–40 wherein R⁷ is J, —A—(M)ₙ(substituted or unsubstituted aliphatic, aryl or heterocyclic), —G—(M)ₙ(substituted or unsubstituted aliphatic, aryl or heterocyclic), —(M)ₙCOCF₃, —(M)ₙOH, —(M)ₙCOOR, —A—(M)ₙNRR",—(M)ₙCHO, —A—(M)ₙN(R)(CO)R', —A—(M)ₙ—NRR' or —A—(M)ₙ—CO—NRR'; and R⁸ is H.

43. A compound of any of claims 37–40 wherein R⁷ is lower alkyl, lower alkenyl, —OH, —NH₂, —NO₂, —CN, —NHR, —NHCOR, —CHO, —CH₂CHO, —PO₃RR', —OPO₃RR', —CH₂PO₃RR', —CF₂PO₃RR', —OCH₂CO₂R, —NHCH₂CO₂R, —CH₂CO₂R, —CF₂CO₂R, —SO₃R, —CH₂SO₃R, —CF₂SO₃R, —COCF₃, —COCH₂F, —COCF₂H, —CF₂COCF₃ or —SO₂NH₂.

44. A compound of claim 43 in which one or both of R and R' in —PO₃RR', —OPO₃RR, —CH₂PO₃RR, —CF₂PO₃RR', —OCH₂CO₂R, —NHCH₂CO₂R, —CH₂CO₂R, —CF₂CO₂R, —SO₃R, —CH₂SO₃R, or —CF₂SO₃R is H.

45. A compound of claim 43 in which one or both of R and R' in —PO₃RR', —OPO₃RR', —CH₂PO₃RR', —CF₂PO₃RR', —OCH₂CO₂R, —NHCH₂CO₂R, —CH₂CO₂R, —CF₂CO₂R, —SO₃R, —CH₂SO₃R, or —CF₂SO₃R is —(M)ₘ—CH₂Z, —(M)ₘ—CHZ₂, —(M)ₘ—CZ₃, —R¹⁵, —M—O—CO—OR¹⁵ or —M—O—CO—OR¹⁵, where Z is halogen and R¹⁵ is substituted or unsubstituted lower aliphatic, aryl or heterocyclic.

46. A compound of claim 45 in which R¹⁵ is methyl, ethyl, n-propyl, i-propyl, n-butyl, isobutyl, t-butyl, n-amyl, sec-amyl, benzyl or substituted benzyl.

47. A compound of claim 34 wherein R⁶ comprises —APO₃RR' or —OPO₃RR' and R⁷ is —A—(M)ₙ-aliphatic or —G—(M)ₙ-aliphatic, where the aliphatic moiety is substituted or unsubstituted.

48. A compound of claim 41 or 47 wherein R⁶ comprises —OPO₃H₂.

49. A compound of claim 34 wherein R⁶ and R⁷ are independently selected from J and K.

50. A compound of claim 34 wherein R⁶ is —C(R)(J)(K).

51. A compound of claim 50 wherein R is H.

52. A compound of claim 50 or 51 wherein J is —PO₃RR'.

53. A compound of claim 52 in which one or both of R and R' are H.

54. A compound of claim 52 in which one or both of R and R' are R¹⁵, —(M)ₘ——CH₂Z, —(M)ₘCHZ₂, —(M)ₘCZ₃, —M—O—CO—OR¹⁵ or —M—O—CO—OR¹⁵, where Z is halogen and R¹⁵ is substituted or unsubstituted lower aliphatic, aryl or heterocyclic.

55. A compound of claim 54 in which R¹⁵ is methyl, ethyl, n-propyl, i-propyl, n-butyl, isobutyl, t-butyl, n-amyl, sec-amyl, benzyl or substituted benzyl.

56. A compound of any of claims 21–6, comprising a moiety B of the formula

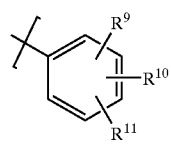

where $R^9$ $R^{10}$ and $R^{11}$ are independently selected from —$(M)_nR$, —$G(M_n)R$, —$(M)_nZ$, —$(M)_nCN$, —$(M)_nGR$, —$(M)_nNRWR$, —$(M)_nNRW$—GR, —$(M)_nW$—R, —G—$(M)_nW$—R, and —$(M)_nW$—GR.

57. A compound of claim 56 comprising a moiety B of the formula

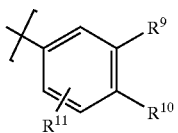

58. A compound of claim 57 in which $R^9$ is H or —WGR and $R^{10}$ is —$G'M_nR'$.

59. A compound of claim 56 in which $R^{11}$ is H.

60. A compound of claim 57 in which $R^{11}$ is H.

61. A compound of claim 58 in which $R^{11}$ is H.

62. A compound of claim 59 in which $R^9$ is H or —C(O)NH$_2$ and $R^{10}$ is —O(CH$_2$)$_n$(aliphatic or cycloaliphatic).

63. A compound of claim 62 in which the aliphatic or cycloaliphatic group in $R^{10}$ is a substituted or unsubstituted methyl, ethyl, n-propyl, n-butyl, t-butyl, n-pentyl, or benzyl moiety or comprises the formula —CHR$^{16}$R$^{17}$ where $R^{16}$ and $R^{17}$ are independently selected lower aliphatic groups or are covalently linked together forming a cycloaliphatic ring.

64. A compound of claim 62 in which n is 1 or 2.

65. A compound of claim 63 or 64 in which $R^{10}$ is —OCH$_2$CHMe$_2$, —OCH$_2$CH(Me)(Et), —OCH$_2$CH(Et)$_2$, —OCH$_2$CH(Me)(Propyl), —OCH$_2$CH(Et)(Propyl), —OCH$_2$CH(Et)(Propyl), —OCH$_2$CH(propyl)$_2$, OCH$_2$cyclopentyl, OCH$_2$cyclohexyl or OCH$_2$cycloheptyl.

66. A compound of claim 56 wherein one or more of the R groups of $R^9$, $R^{10}$ and $R^{11}$ contain at least one substituent selected from halo, hydroxy, aliphatic, amino, amido and sulfonamido moieties.

67. A compound of any of claims 1'21 and 6 in which B is —C(O)NR$^{12}$R$^{13}$.

68. A compound of claim 67 in which $R^{12}$ is lower alkyl and $R^{13}$ is aliphatic, —$M_n$-cycloaliphatic, —$M_n$-aryl, —$M_n$-heteroaryl, or —$M_n$CO$_2$R, where the aliphatic, cycloaliphatic, aryl or heteroaryl moiety(ies) is(are) substituted or unsubstituted).

69. A compound of claim 68 in which $R^{13}$ is —(CH$_2$)-aliphatic —(CH$_2$)$_n$-cycloaliphatic.

70. A compound of claim 69 in which n in $R^{13}$ is 2–4.

71. A compound of any of claims 1–21 and 6 of the formula

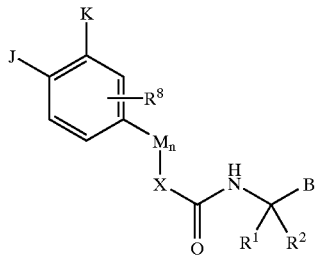

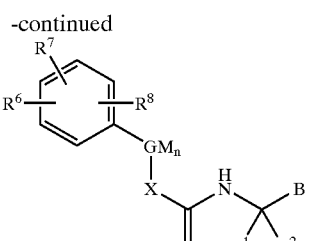

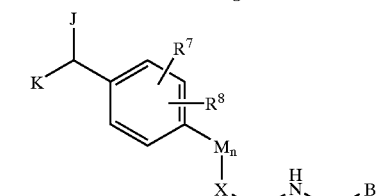

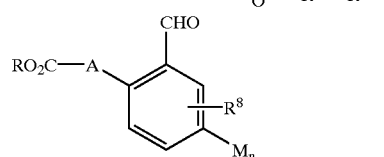

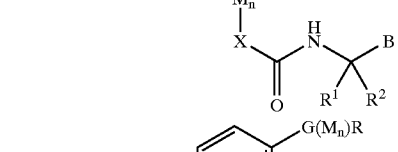

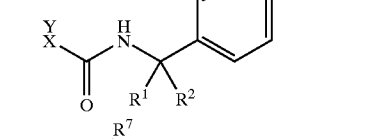

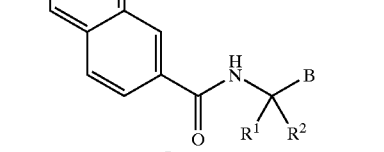

or

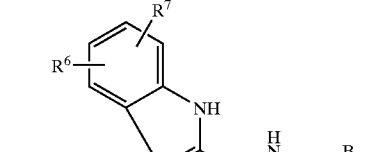

72. A compound of claim 71 of the formula

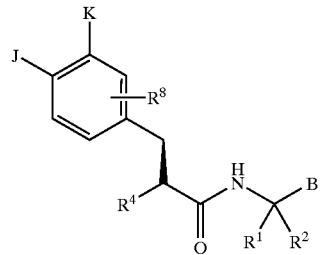

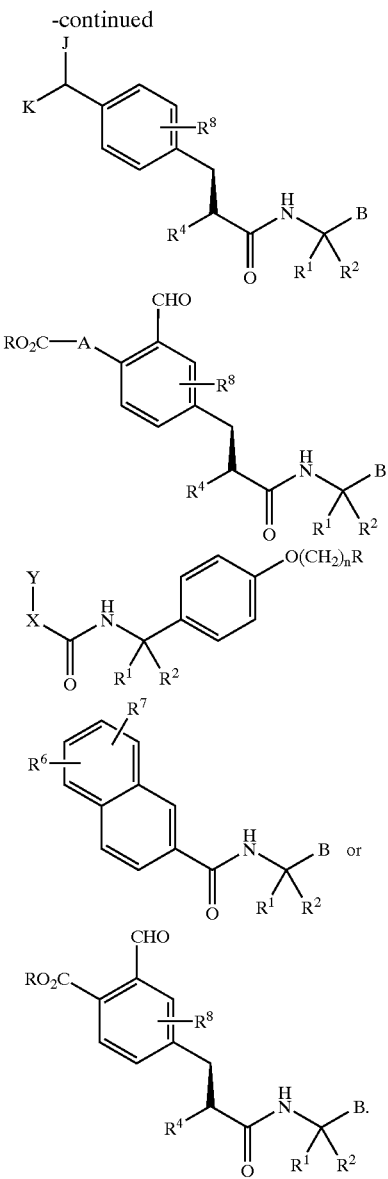

73. A compound of the formula

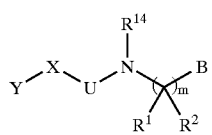

wherein
Y is

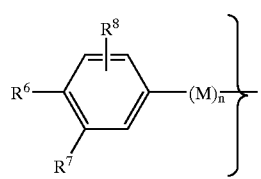

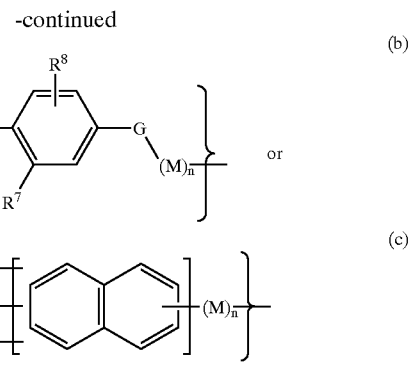

G is —O—, —S— or —NR—;

R⁶ comprises —C(R)(J)(K) or —C(Z)(J)(K);

where each occurrence of A is independently a covalent bond, —G—M— or —(M)$_m$—;

each occurrence of M is an independently selected, substituted or unsubstituted, methylene moiety, and any M—M' moiety may be electronically saturated or unsaturated;

each n is independently 0, 1, 2, 3, 4 or 5;

each m is independently 0, 1 or 2;

J and K are independently —APO₃RR', —OPO₃RR', —ASO₃R, —OSO₃R, —ACO₂R, —A-tetrazole, —ASO₂NRR', —(M)$_n$—NRR' or —(M)$_n$—OR;

Z is a halogen;

R⁷ and R⁸ are independently R, —CN, —NO₂, Z, J, —A(M)$_n$aliphatic, —G(M)$_n$aliphatic, —(M)$_n$COR) —(M)$_n$OR, —(M)$_n$COOR, —A—(M)$_n$NRR', —G(M)$_q$NRR', —(M)$_n$CHO, —A(M)$_n$N(R)(CO)R', —A(M)$_n$N(R)(CO)GR', —G(M)$_n$N(R)(CO)R', —G—(M)$_n$N(R)(CO)G'R', —A—(M)$_n$—CO—NRR', or —G(M)$_n$—CO—NRR, where the aliphatic groups may be substituted or unsubstituted; or R⁸ is a covalent bond to an R⁴ substituent of X to form an aliphatic, aryl or heterocyclic ring of 4 to 8 atoms which may be saturated or unsaturated;

each occurrence of R (unnumbered) represents hydrogen or an aliphatic, heteroaliphatic, aryl, heteroaryl, (aryl)aliphatic-, or (heteroaryl)aliphatic-moiety, each of which (other than hydrogen) may be substituted or unsubstituted;

q is an integer from 1 to 8;

R¹ is hydrogen, aliphatic, —(M)$_n$-cycloaliphatic, —(M)$_n$-aryl, or —(M)$_n$-heterocyclic, each of which, other than H, may be substituted or unsubstituted; and R² is hydrogen or substituted or unsubstituted aliphatic;

or R¹ and R² are covalently linked together to form a ring;

or R¹ or R² are covalently linked to B or a substituent of B to form a 4–0-membered ring (which may be saturated or unsaturated);

X is: —(CR³R⁴)$_m$— or —NR⁴—;

R³ is hydrogen, R(CO)NR'—, RR'N(CO)NR"—, R'SO₂NR—, R'C(S)NR—, RR'NCSNR"—, RR'NSO₂NR"—, R'OCONR—, RR'N—, or

$R^4$ is hydrogen, aliphatic, cycloaliphatic-$(M)_n$—, aryl-$(M)_n$—, heterocyclic-$(M)_n$—, R—$SO_2M_n$—, (RO—CO)$(M)_n$— or (RR'N—CO)$(M)_n$—, where the aliphatic, cycloaliphatic, aryl or heterocyclic moiety is substituted or unsubstituted;

B is

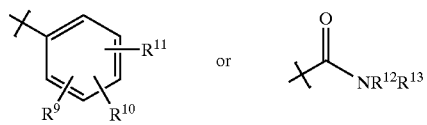

where $R^9$, $R^{10}$ and $R^{11}$ are independently selected from —$(M)_n$R, —G$(M_n)$R, —$(M)_n$Z, —$(M)_n$CN, —$(M)_n$GR, —$(M)_n$NRWR, —$(M)_n$NRW—GR, —$(M)_n$W—R, —G—$(M)_n$W—R, and —$(M)_n$W—GR, or $R^{10}$ and $R^{11}$ are covalently linked together to form an aliphatic, hetercyclic or aryl fused ring;

$R^{12}$ and $R^{13}$ are independently selected from the group consisting of hydrogen, aliphatic, heteroaliphatic, aryl, heteroaryl, (aryl)aliphatic-, or (heteroaryl)aliphatic, each of which (other than hydrogen) may be substituted or unsubstituted; or $R^{12}$ and $R^{13}$ are covalently linked together to form a heterocyclic moiety;

$R^{14}$ is R; and,

U and W are independently —CO—, —CS—, —M—, —SO—, or —$SO_2$—;

or a pharmaceutically acceptable derivative thereof.

\* \* \* \* \*